(12) United States Patent
Furuland

(10) Patent No.: US 10,163,321 B2
(45) Date of Patent: Dec. 25, 2018

(54) MONITORING SYSTEM

(71) Applicant: Enfant Terrible Design AB, Norrtälje (SE)

(72) Inventor: Lisa Furuland, Norrtälje (SE)

(73) Assignee: Enfant Terrible Design AB, Norrtälje (SE)

( * ) Notice: Subject to any disclaimer, the term of this patent is extended or adjusted under 35 U.S.C. 154(b) by 0 days.

(21) Appl. No.: 15/729,738

(22) Filed: Oct. 11, 2017

(65) Prior Publication Data

US 2018/0102039 A1    Apr. 12, 2018

Related U.S. Application Data

(60) Provisional application No. 62/406,705, filed on Oct. 11, 2016, provisional application No. 62/413,593, filed on Oct. 27, 2016.

(51) Int. Cl.
*G08B 13/00* (2006.01)
*G08B 21/04* (2006.01)
(Continued)

(52) U.S. Cl.
CPC ........ *G08B 21/0461* (2013.01); *A61B 5/0022* (2013.01); *A61B 5/1113* (2013.01);
(Continued)

(58) Field of Classification Search
CPC ..... A61B 5/002; A61B 5/0205; A61B 5/0816; A61B 2562/0228; A61B 2562/046;
(Continued)

(56) References Cited

U.S. PATENT DOCUMENTS 2,626,407 A    1/1953    Kurry
2,633,898 A    4/1953    Worgan
(Continued)

FOREIGN PATENT DOCUMENTS

CN    205107063 U    3/2016
CN    205458603 U    8/2016
(Continued)

OTHER PUBLICATIONS

PCT International Search Report and Written Opinion issued in PCT/IB2012/003999 dated Aug. 2, 2013.
(Continued)

*Primary Examiner* — Daniel Previl
(74) *Attorney, Agent, or Firm* — Ward and Smith, P.A.; Ryan K. Simmons

(57) ABSTRACT

A monitoring system has sensors for monitoring a comfort of a user. For example, a motion sensor may detect movements as the user lies or plays in the monitoring system. The motion sensor is sensitive to detect expansion and contraction of a chest cavity, thus monitoring the user's breathing status. Other sensors may detect other environmental data, such as temperature, humidity, and even the user's voice. Collectively, the sensors may be used to infer the user's status/comfort. The monitoring system may collect the data and then infer the user's comfort. The monitoring system may also send the data to another device for analysis, such as a computer, smartphone, or even a server providing a cloud-based service.

40 Claims, 76 Drawing Sheets

(51) Int. Cl.
| | |
|---|---|
| *H04L 29/08* | (2006.01) |
| *G08B 21/02* | (2006.01) |
| *A61B 5/00* | (2006.01) |
| *A61B 5/11* | (2006.01) |
| *G16H 10/60* | (2018.01) |
| *G06F 19/00* | (2018.01) |

(52) U.S. Cl.
CPC .......... *A61B 5/1118* (2013.01); *A61B 5/6892* (2013.01); *A61B 5/746* (2013.01); *G08B 21/0211* (2013.01); *H04L 67/1097* (2013.01); *H04L 67/125* (2013.01); *A61B 2503/04* (2013.01); *G06F 19/3418* (2013.01); *G16H 10/60* (2018.01)

(58) Field of Classification Search
CPC .............. A61B 2562/166; A61B 5/024; A61B 5/02444; A61B 5/05; A61B 5/08; A61B 5/103; A61B 5/1113; A61B 5/1115; A61B 5/1117
USPC .............. 340/539.22, 573.1, 539.26, 539.15, 340/539.12, 539.1, 539.11, 691.7, 5.52, 340/5.64, 5.82, 825.36, 286.07
See application file for complete search history.

(56) References Cited

U.S. PATENT DOCUMENTS

| | | | |
|---|---|---|---|
| 3,583,765 A | 6/1971 | Wallis | |
| 3,761,975 A | 10/1973 | Personett | |
| 4,066,072 A | 1/1978 | Cummins | |
| 4,146,885 A * | 3/1979 | Lawson, Jr. | G08B 21/22 340/573.1 |
| D263,192 S | 3/1982 | LeVan | |
| 4,383,713 A | 5/1983 | Roston | |
| 4,438,771 A | 3/1984 | Friesen et al. | |
| 4,607,402 A | 8/1986 | Pollard | |
| 4,788,726 A | 12/1988 | Rafalko | |
| 4,802,244 A | 2/1989 | McGrath-Saleh | |
| 4,972,864 A | 11/1990 | Almond | |
| D317,232 S | 6/1991 | Vogtherr et al. | |
| 5,035,013 A | 7/1991 | Bloom | |
| 5,088,139 A | 2/1992 | Bloom | |
| 5,137,333 A | 8/1992 | Chee | |
| D330,139 S | 10/1992 | Bloom | |
| 5,165,130 A | 11/1992 | Wendling | |
| D333,389 S | 2/1993 | Saito et al. | |
| 5,242,338 A | 9/1993 | Hatdegen, III et al. | |
| 5,299,883 A | 4/1994 | Arth, Jr. | |
| 5,392,785 A | 2/1995 | Donahue | |
| 5,448,790 A | 9/1995 | Saro et al. | |
| 5,519,906 A | 5/1996 | Fanto-Chan | |
| 5,551,109 A | 9/1996 | Tingley et al. | |
| 5,586,351 A | 12/1996 | Ive | |
| D380,274 S | 6/1997 | Stamets | |
| D393,772 S | 4/1998 | Vingino | |
| 5,796,340 A | 8/1998 | Miller | |
| 5,813,066 A | 9/1998 | Geghard et al. | |
| D415,919 S | 11/1999 | Porter | |
| 6,047,420 A | 4/2000 | Priester, III et al. | |
| D465,585 S | 11/2002 | Venegas, Jr. | |
| 6,505,366 B1 | 1/2003 | Lied | |
| 6,536,058 B1 | 3/2003 | Chang | |
| 6,588,036 B1 | 7/2003 | Hort | |
| 7,234,199 B2 | 6/2007 | Bushey | |
| 7,302,724 B2 | 12/2007 | Solomon et al. | |
| 7,404,219 B2 | 7/2008 | Berkey | |
| 7,588,291 B2 | 9/2009 | Gold et al. | |
| 7,676,871 B1 | 3/2010 | Leach | |
| 7,766,367 B2 | 8/2010 | Dotsey et al. | |
| 7,926,135 B1 | 4/2011 | Leach | |
| 8,024,829 B2 | 9/2011 | Carr et al. | |
| D652,712 S | 1/2012 | Bushey | |
| 8,169,329 B2 | 5/2012 | Koblasz et al. | |
| D666,843 S | 9/2012 | Furuland | |
| D673,789 S | 1/2013 | Furuland | |
| D673,790 S | 1/2013 | Furuland | |
| D673,791 S | 1/2013 | Furuland | |
| 8,419,128 B1 | 4/2013 | Leach | |
| 8,458,830 B1 | 6/2013 | Pierce et al. | |
| 8,555,429 B2 | 10/2013 | Leach | |
| D716,896 S | 11/2014 | Blackwood | |
| 9,464,646 B2 | 10/2016 | Burns et al. | |
| D774,879 S | 12/2016 | Martinson | |
| 9,788,663 B2 | 10/2017 | Furuland | |
| 2004/0064887 A1 | 4/2004 | Cheng | |
| 2005/0076444 A2* | 4/2005 | Houghteling | A47D 13/08 5/655 |
| 2005/0124864 A1* | 6/2005 | Mack | A61B 5/024 600/300 |
| 2005/0155155 A1 | 7/2005 | Kassai et al. | |
| 2005/0172408 A1 | 8/2005 | Temple | |
| 2005/0210591 A1 | 9/2005 | Mead et al. | |
| 2006/0026766 A1 | 2/2006 | Brewin et al. | |
| 2007/0245494 A1 | 10/2007 | Dockendorf | |
| 2007/0256242 A1 | 11/2007 | Warnock | |
| 2008/0040854 A1 | 2/2008 | Lorentz | |
| 2008/0068182 A1* | 3/2008 | Watson | A61B 5/053 340/573.1 |
| 2008/0182477 A1 | 7/2008 | Catelli | |
| 2008/0213039 A1 | 9/2008 | Chen et al. | |
| 2009/0083908 A1 | 4/2009 | Fry | |
| 2009/0151080 A1 | 6/2009 | Lord | |
| 2009/0193589 A1* | 8/2009 | Carr | A47D 13/08 5/655 |
| 2009/0222993 A1 | 9/2009 | Villanueva et al. | |
| 2011/0119833 A1 | 5/2011 | Clark | |
| 2011/0191956 A1 | 8/2011 | Rabess et al. | |
| 2011/0277210 A1 | 11/2011 | Hardesty | |
| 2013/0111661 A1 | 5/2013 | Furuland | |
| 2013/0165809 A1 | 6/2013 | Abir | |
| 2015/0164238 A1 | 6/2015 | Benson et al. | |
| 2015/0330549 A1 | 11/2015 | Drane | |
| 2016/0174728 A1 | 6/2016 | Karp et al. | |
| 2016/0235306 A1 | 8/2016 | Atallah et al. | |
| 2016/0248598 A1* | 8/2016 | Lin | H04L 12/2803 |
| 2016/0364617 A1* | 12/2016 | Silberschatz | G06K 9/00771 |

FOREIGN PATENT DOCUMENTS

| | | |
|---|---|---|
| DE | 3617012 A1 | 11/1986 |
| DE | 20007258 U1 | 10/2000 |
| DE | 20203973 U1 | 7/2002 |
| DE | 102009049019 A1 | 4/2011 |
| EP | 2775886 A2 | 9/2014 |
| FR | 2911776 A1 | 8/2008 |
| SE | 20080586 | 8/2009 |
| WO | 2013068849 A2 | 5/2013 |
| WO | 2015143430 A1 | 9/2015 |

OTHER PUBLICATIONS

PCT International Search Report and Written Opinion issued in PCT/IB2017/056292 dated Mar. 19, 2018.

* cited by examiner

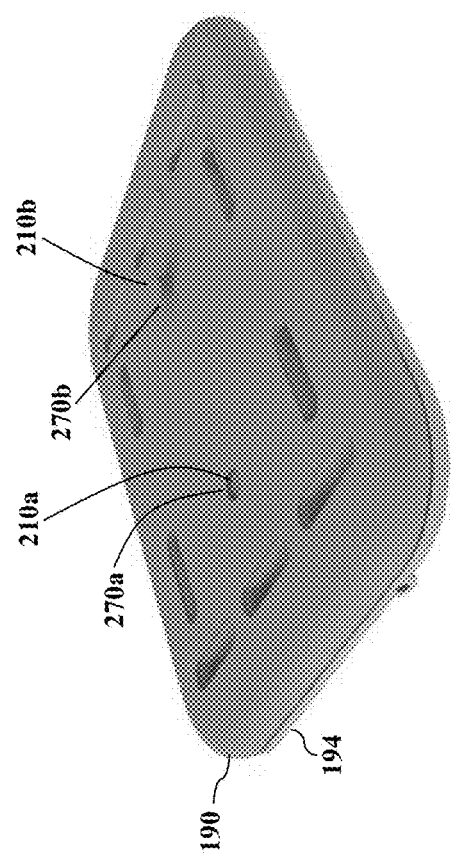
FIG. 19B
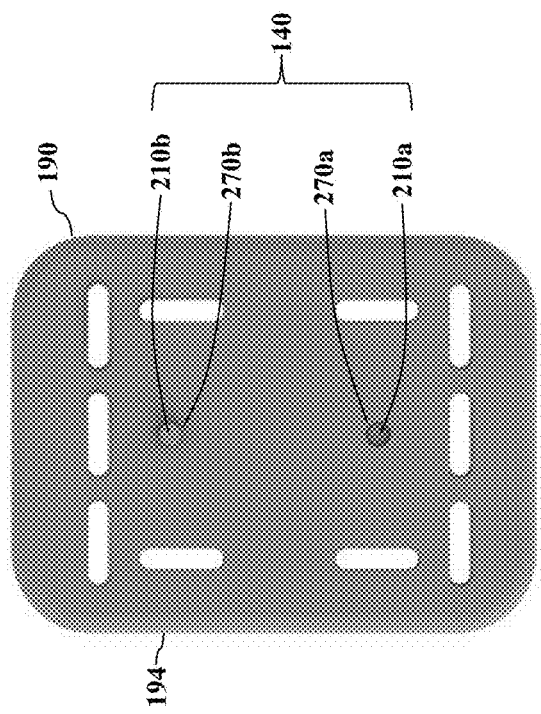
FIG. 19
FIG. 19A

MONITORING SYSTEM

RELATED APPLICATIONS

This application claims priority and is related to U.S. Provisional Patent Application Ser. No. 62/406,705 entitled "Monitoring Pen," filed Oct. 11, 2016, and 62/413,593 entitled "Monitoring Pen," filed Oct. 27, 2016, with the contents of each incorporated herein by reference in their entireties.

BACKGROUND OF THE INVENTION

Monitoring is important in child care. Parents monitor their children to provide better care. Day care providers also wish to monitor children in their care to provide better care.

SUMMARY OF THE INVENTION

Exemplary embodiments include a baby monitoring system having one or more sensors. When a user lies on or within the monitoring system, the sensors collect data to infer the user's status and/or comfort. For example, the monitoring system may have a motion sensor to infer if an infant is breathing. Moreover, other sensors may detect other environmental and/or physiological data, such as ambient temperature, humidity, and even the infant's voice. The monitoring system may collect any data to infer the infant is comfortably playing or resting. The monitoring system, however, may also send the data to another device for analysis and diagnosis.

Exemplary embodiments may even jolt or nudge the user. As the reader may understand, sleep apnea is a common occurrence in adults and infants. Any of the sensors may thus be used to determine when the user pauses or stops breathing. If the monitoring system detects a lack of motion associated with a user's breathing outside of a predetermined threshold, the monitoring system may activate a contact mechanism. The contact mechanism initiates a force input to the monitoring system, such as a nudge or poke, to a pad and/or a mattress, and thus jolts or nudges the user. The contact mechanism may promote the user to resume breathing.

Exemplary embodiments may also include remote monitoring. Any data collected by the monitoring system may be sent or uploaded to a remote device. Suppose, for example, that the monitoring system monitors the infant. That is, as the infant lies or plays within the monitoring system, exemplary embodiments may monitor movements, ambient temperature, humidity, the infant's voice, and any other data. The monitoring system may then wirelessly send the data to the parent's smartphone or other device, thus allowing the parent to remotely monitor the infant's comfort. Should the parent be in another room, at work, or even traveling, exemplary embodiments keep the parent informed of the infant's status and/or comfort.

Exemplary embodiments may also include a cloud-based service. Whenever the monitoring system collects any data, the monitoring system may upload the data to a remote server via a communications network. The server may thus perform a service that infers the infant's comfort based on the data. A service provider, in other words, may provide an Internet-based service that performs an analysis in response to client requests.

In one embodiment, a monitoring system is provided. The system may include a hardware processor; and a memory device, the memory device storing code, the code when executed causing the hardware processor to perform operations, the operations may include receiving an output signal generated by a sensor, the sensor generating the output signal in response to a user lying on a cushioned pad; comparing the output signal to a threshold value; and activating a contact mechanism that imparts a force to the cushioned pad, the contact mechanism activated in response to the output signal satisfying the threshold value, the force being to provoke a movement of the user lying on the cushioned pad to alter the output signal generated by the sensor. The contact mechanism may include at least one peg. The contact mechanism may slide the at least one peg into contact with the cushioned pad to impart the force. The operations may further include identifying a motor command in response to the output signal, the motor command commanding a motor to cause the at least one peg to slide into contact with the cushioned pad. The contact mechanism may slide the at least one peg to impart the force to propagate through the cushioned pad. The operations may further include receiving a motor command that commands a motor to cause the at least one peg to impart the force to propagate through the cushioned pad. The operations may further include querying an electronic database for a value associated with the output signal generated by the sensor, the electronic database electronically associating motor commands to values including the value associated with the output signal generated by the sensor. The operations may further include identifying a motor command of the motor commands in the electronic database that is electronically associated with the value associated with the output signal generated by the sensor. The operations may further include sending the motor command to a motor to cause the force imparted to the cushioned pad. The operations may further include inferring a comfort associated with the user lying on the cushioned pad, the comfort based on the output signal generated by the sensor. The operations may further include inferring the user rests on the cushioned pad based on the output signal generated by the sensor. The operations may further include determining an apneatic condition based on the output signal generated by the sensor, the apneatic condition indicating the user lying on the cushioned pad has suspended breathing, and wherein the contact mechanism may impart the force to promote a resumption of the breathing of the user. The operations may further include determining a humidity based on the output signal generated by a humidity sensor, the humidity sensor generating the output signal in response to the user lying on the cushioned pad. The operations may further include determining a humidity based on the output signal generated by a humidity sensor, the humidity sensor comprising at least one conductive strand incorporated into a textile covering the cushioned pad, the humidity sensor generating the output signal in response to the user lying on the cushioned pad above the at least one conductive strand.

In another embodiment, a monitoring system is provided. The system may include a cushioned pad; a motion sensor; a contact mechanism; a hardware processor; and a memory device, the memory device storing code, the code when executed causing the hardware processor to perform operations, the operations may include receiving an output signal generated by the motion sensor, the motion sensor generating the output signal in response to a user lying on the cushioned pad; comparing the output signal to a threshold value; determining a status associated with the user in response to the output signal satisfying the threshold value; and activating the contact mechanism to impart a force through the cushioned pad in response to the status, the contact mechanism for provoking a movement of the user lying on the cushioned pad to alter the output signal generated by the motion sensor. The contact mechanism may include at least one peg. The contact mechanism may slide the at least one peg to impart the force through the cushioned pad. The contact mechanism reciprocates the at least one peg into contact with an upper region of the cushioned pad. The operations may further include determining an apneatic condition indicating the user has suspended breathing, and wherein the contact mechanism activates to promote a resumption of the breathing of the user lying on the cushioned pad. The operations may further include generating a motor command in response to the output signal generated by the motion sensor, the motor command commanding the contact mechanism to impart the force through the cushioned pad. The operations may further include receiving a motor command that commands the contact mechanism to impart the force through the cushioned pad. The operations may further include wirelessly sending an indication of the output signal to a mobile device. The operations may further include wirelessly sending an indication of the output signal to a server. The operations may further include determining a humidity based on an output signal generated by a humidity sensor, the humidity sensor generating the output signal in response to the user lying on the cushioned pad. The operations may further include determining a humidity based on an output signal generated by a humidity sensor, the humidity sensor comprising at least one conductive strand incorporated into a textile covering the cushioned pad, the humidity sensor generating the output signal in response to the user lying on the cushioned pad above the at least one conductive strand.

In yet another embodiment, a method is provided. The method may include receiving, by a server, a service request sent via the Internet from a client device, the service request requesting a cloud-based monitoring service performed on behalf of the client device, the service request specifying a value associated with an output signal generated by a motion sensor in response to a user lying on a cushioned pad; querying, by the server, an electronic database for the value associated with the output signal generated by the motion sensor, the electronic database electronically associating motor commands to values including the value associated with the output signal generated by the motion sensor; identifying, by the server, a motor command of the motor commands in the electronic database that is electronically associated to the value associated with the output signal generated by the motion sensor; and sending, by the server, the motor command via the Internet to the client device, the motor command sent in response to the service request requesting the cloud-based monitoring service, the motor command causing the client device to activate a contact mechanism in response to the value associated with the output signal generated by the motion sensor, the contact mechanism activated to impart a force through the cushioned pad to provoke a movement of the user lying on the cushioned pad to alter the value associated with the output signal generated by the motion sensor. The method may further include retrieving a notification address associated with the client device sending the service request. The method may further include sending an electronic notification to the notification address associated with the client device sending the service request, the electronic notification notifying of the status. The method may further include initiating a short message service text message to the notification address associated with the client device sending the service request, the short message service text message notifying of the status. The method may further include identifying an apneatic condition that is electronically associated to the value associated with the output signal generated by the motion sensor, the apneatic condition indicating the user has suspended breathing. The method may further include sending an electronic notification to a notification address associated with the client device sending the service request, the electronic notification notifying of the apneatic condition indicating the user has suspended the breathing. The method may further include initiating a short message service text message to a notification address associated with the client device sending the service request, the short message service text message notifying of the apneatic condition indicating the user has suspended the breathing.

In still yet another embodiment, a monitoring system is provided. The system may include a contact mechanism having at least one peg; a cushioned pad overlaying the contact mechanism having the peg; a motion sensor; a hardware processor; and a memory device, the memory device storing code, the code when executed causing the hardware processor to perform operations, including: receiving an output signal generated by the motion sensor, the motion sensor generating the output signal in response to a user lying on the cushioned pad; comparing the output signal to a threshold value; determining a status associated with the user lying on the cushioned pad, the status determined in response to the output signal satisfying the threshold value; activating the contact mechanism in response to the status; and reciprocating the peg to impart a force through the cushioned pad overlaying the contact mechanism; wherein the force is for provoking a movement in the user lying on the cushioned pad to alter the output signal generated by the motion sensor. The operations may further include determining an apneatic condition indicating the user has suspended breathing, and wherein the reciprocating of the peg promotes a resumption of the breathing, and wherein the resumption of the breathing changes the output signal generated by the motion sensor. The operations may further include identifying a motor command in response to the output signal generated by the motion sensor, the motor command causing an activation of the contact mechanism to reciprocate the peg. The monitoring system may further include a humidity sensor for sensing a humidity associated with the user lying on the cushioned pad. The humidity sensor may include a conductive textile for sensing the humidity associated with the user lying on the cushioned pad. The humidity sensor may include conductive strands disposed between the cushioned pad and the contact mechanism. The humidity sensor may include conductive strands integrated into a covering of the cushioned pad. The humidity sensor may include conductive strands disposed between an upper surface of the cushioned pad and the contact mechanism.

BRIEF DESCRIPTION OF THE DRAWINGS

Figure 14:
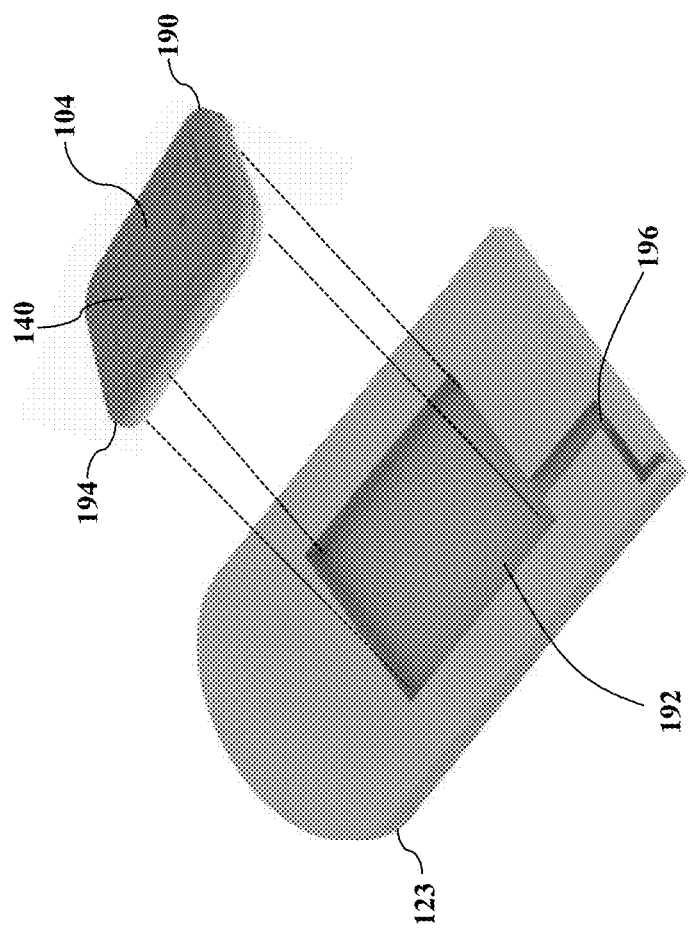
Figure 15:
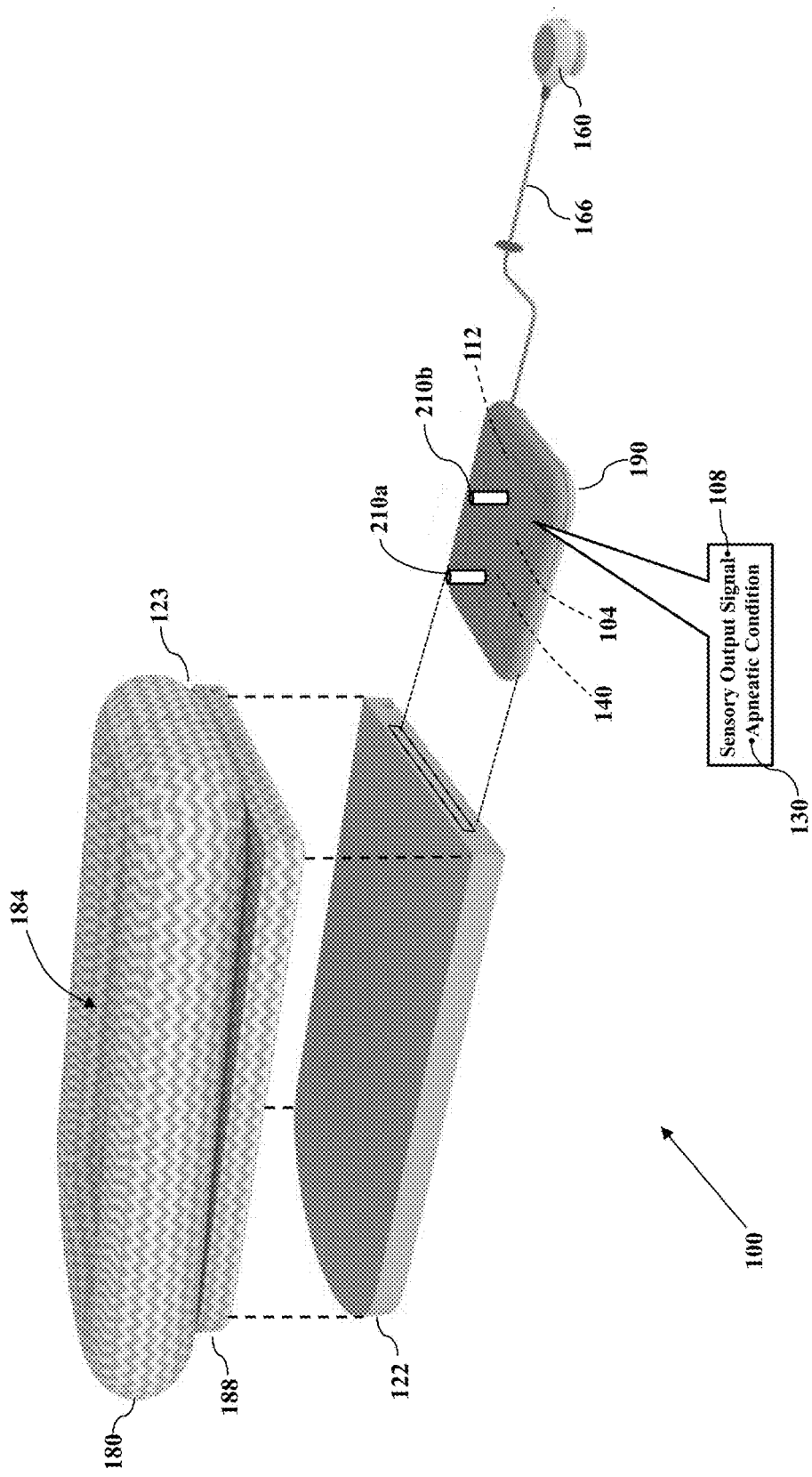
Figure 16:
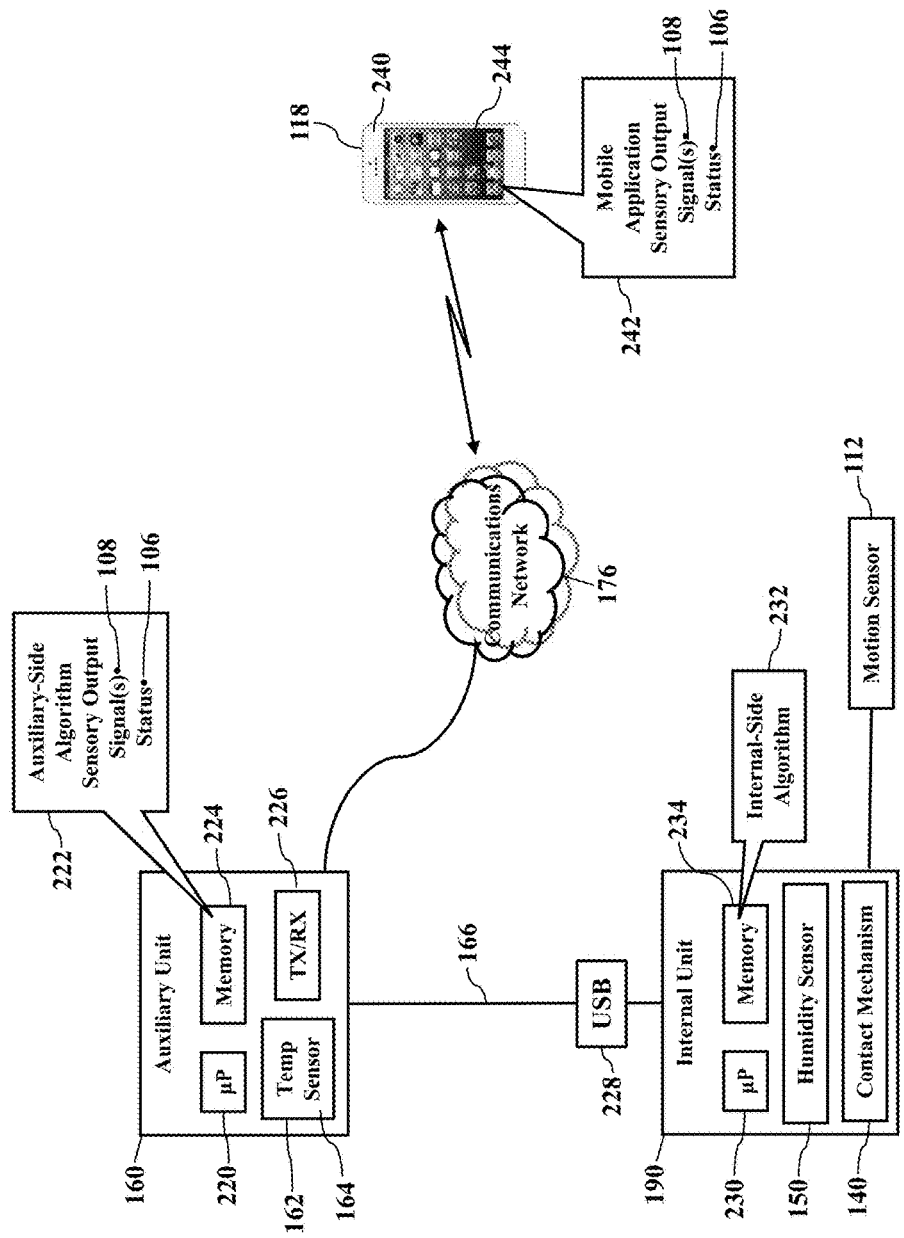
Figure 21:
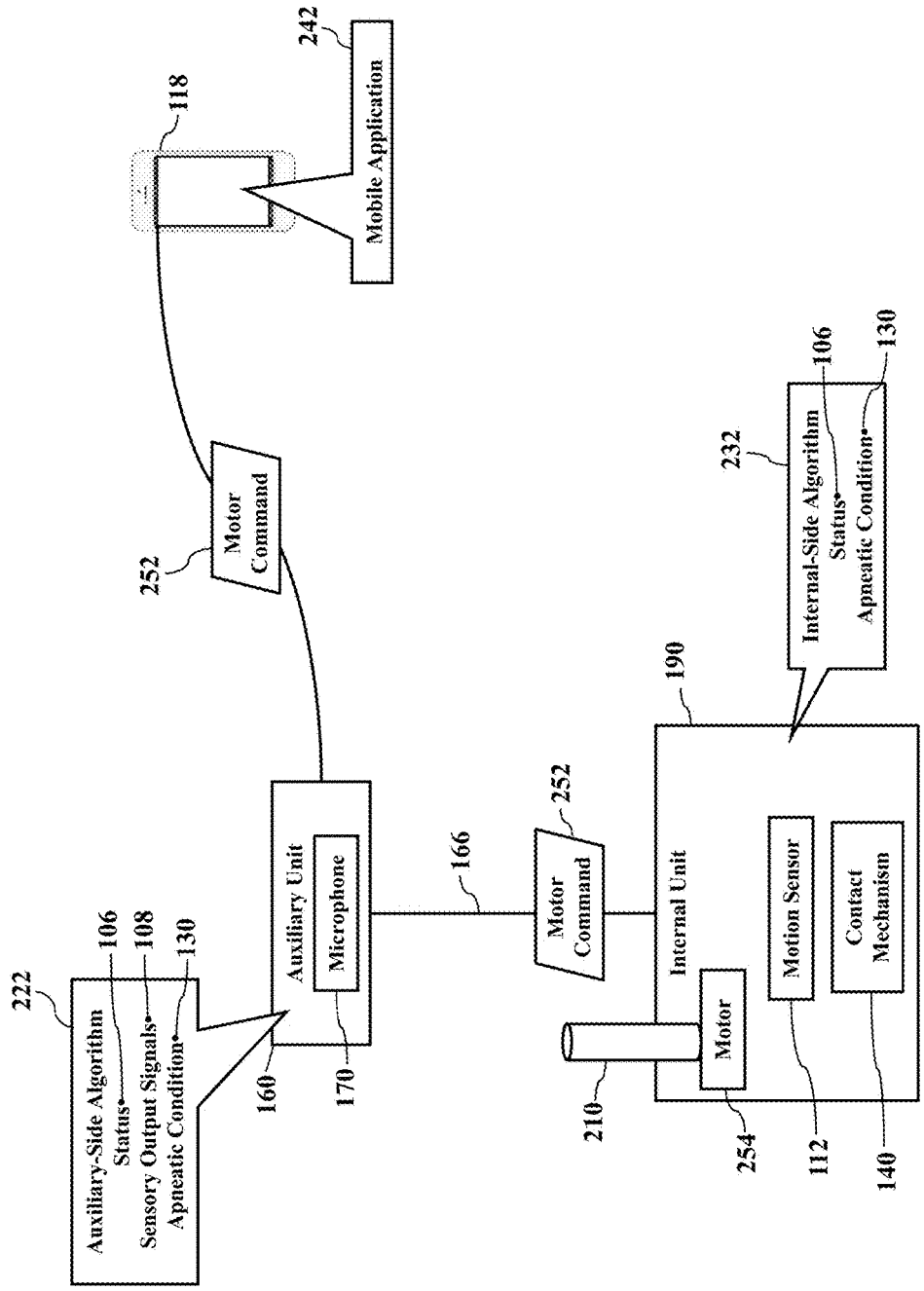
Figure 22:
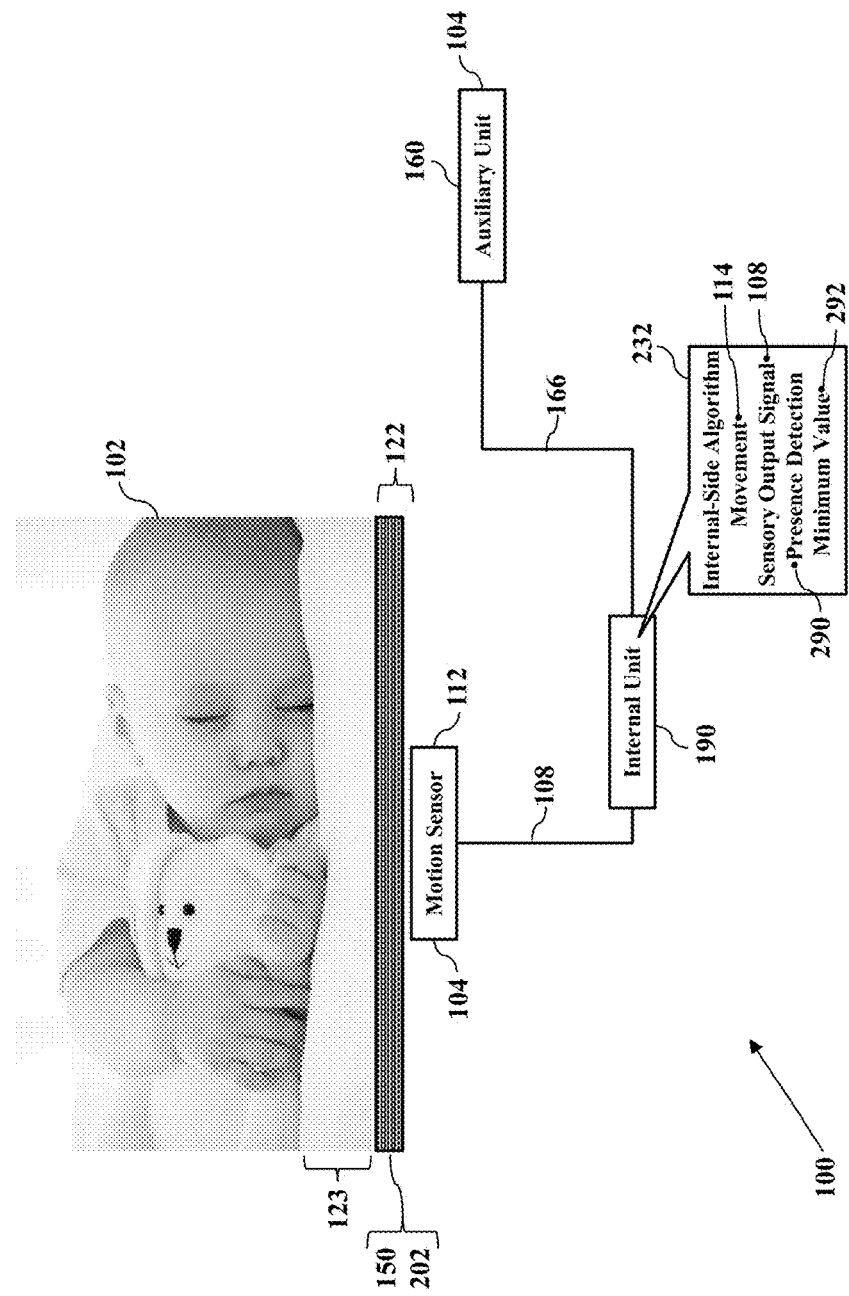
Figure 23:
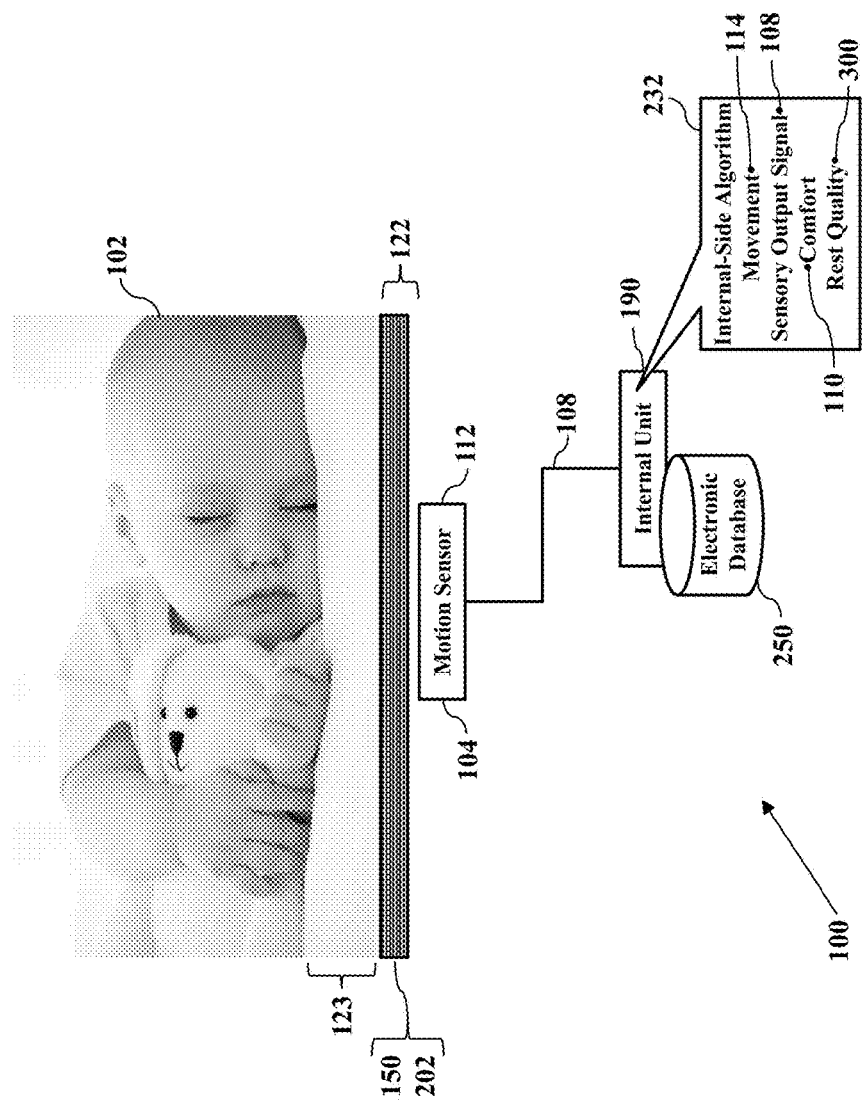
Figure 24:
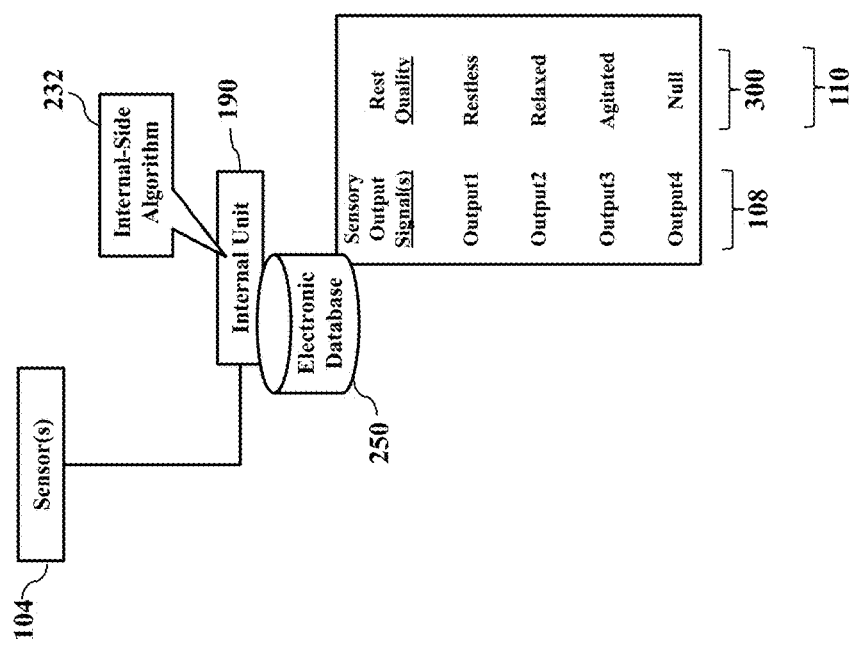
Figure 25:
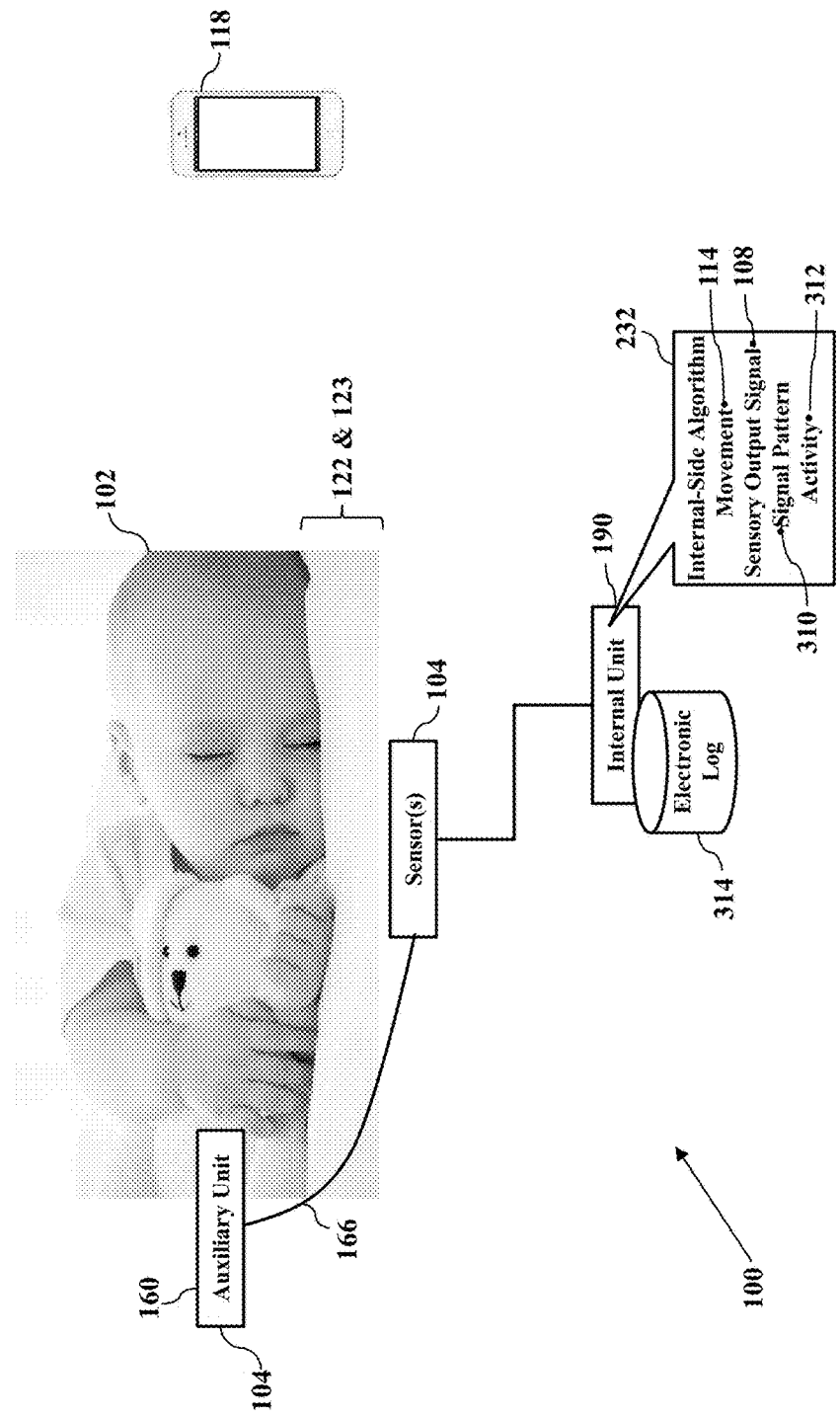
Figure 26:
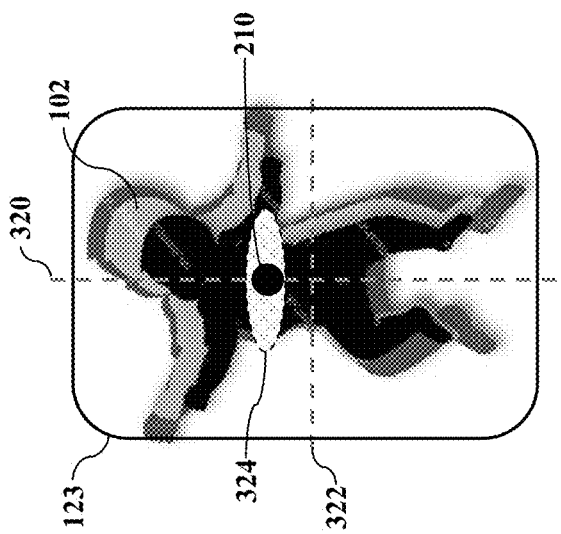
Figure 31:
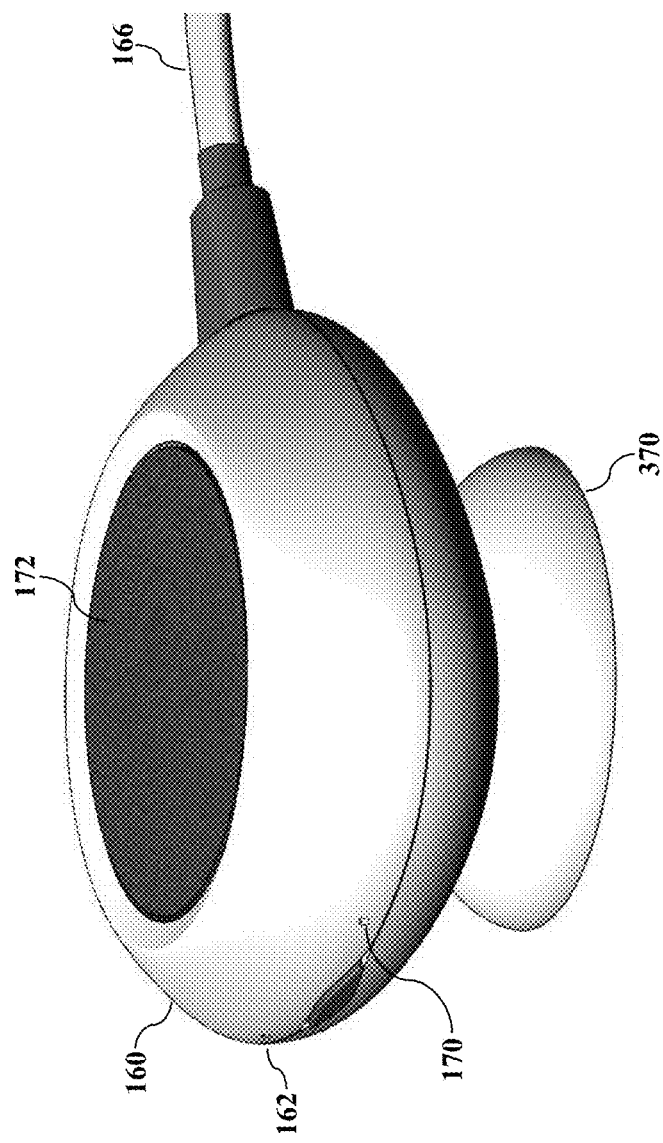
Figure 32:
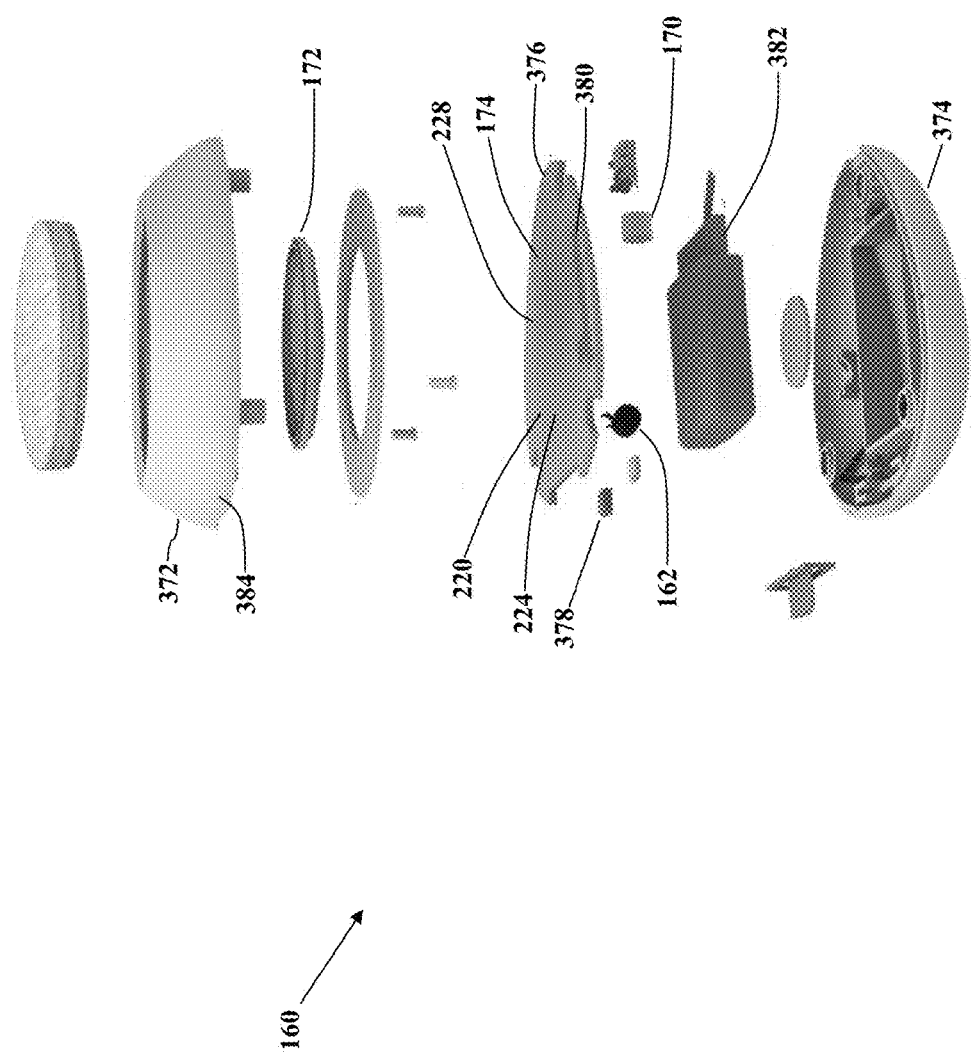
Figure 33:
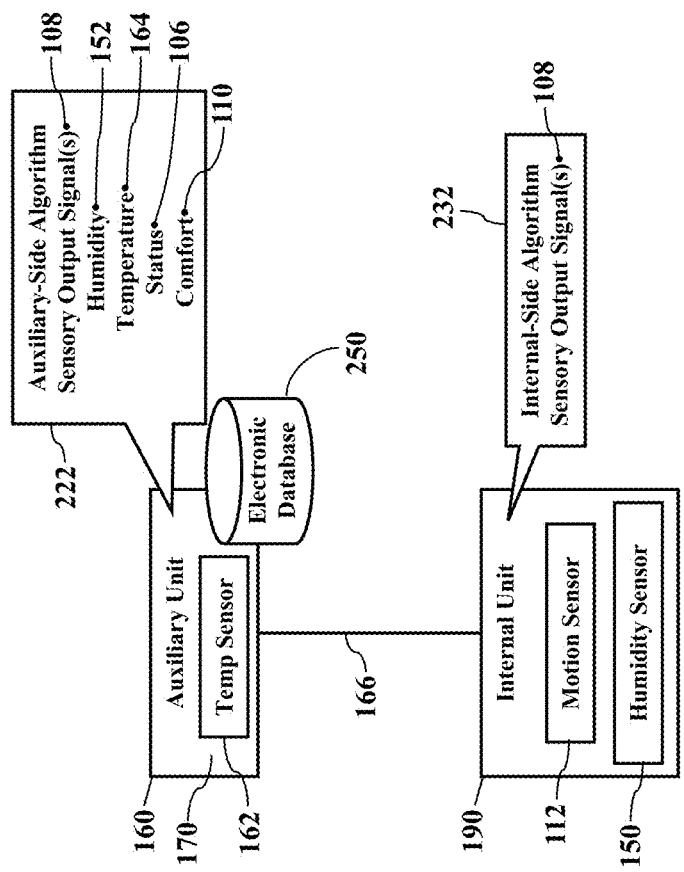
Figure 34:
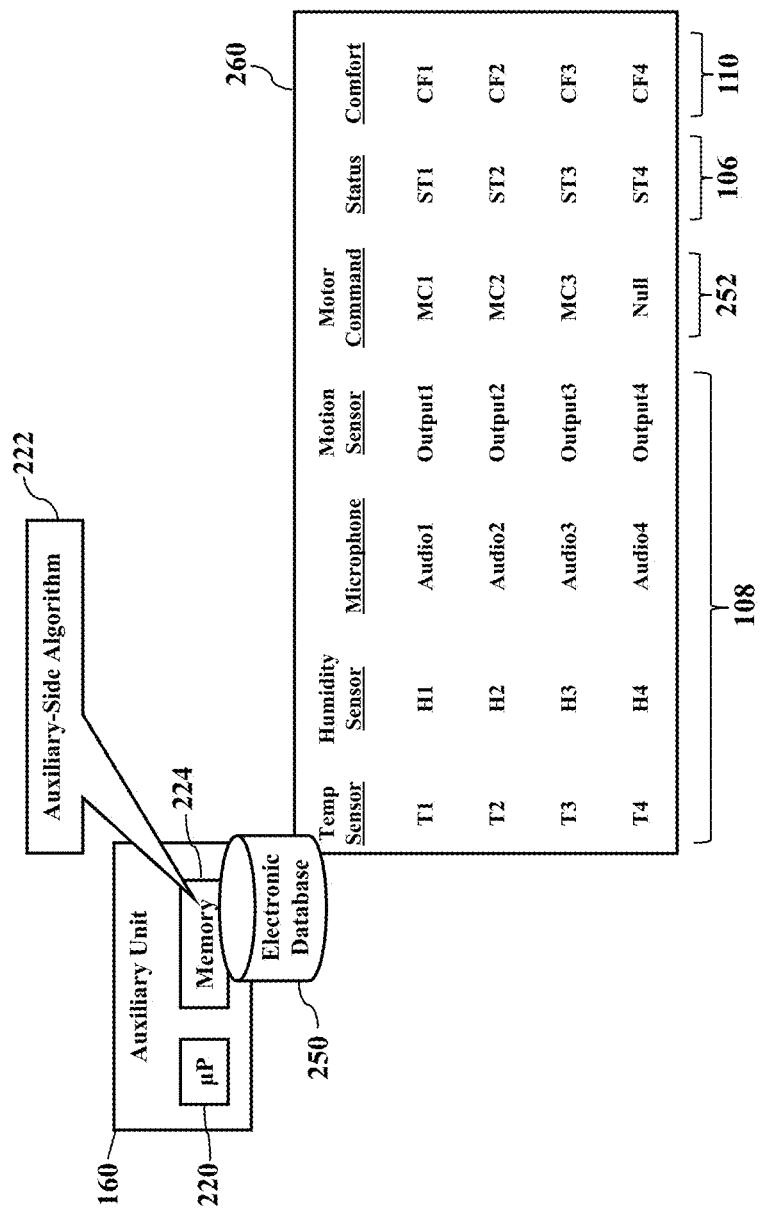
Figure 35:
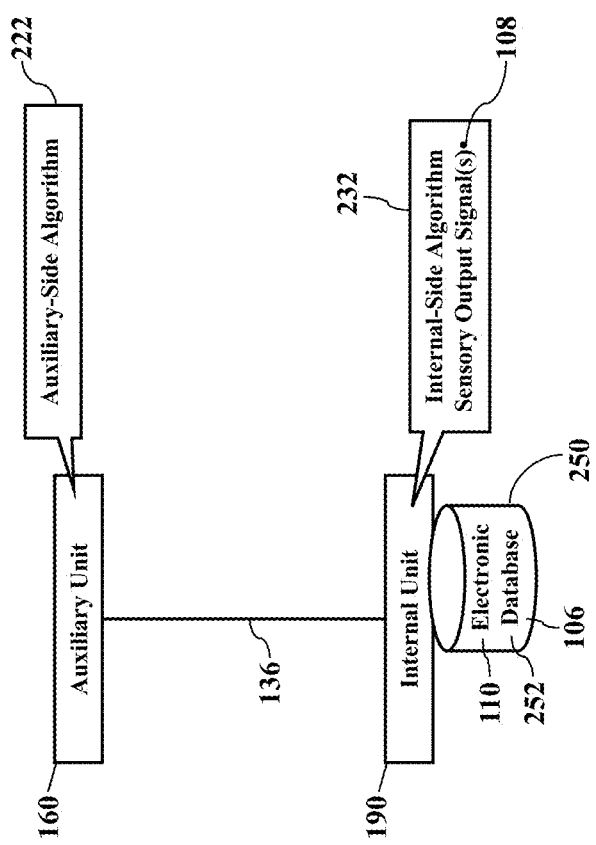
Figure 40:
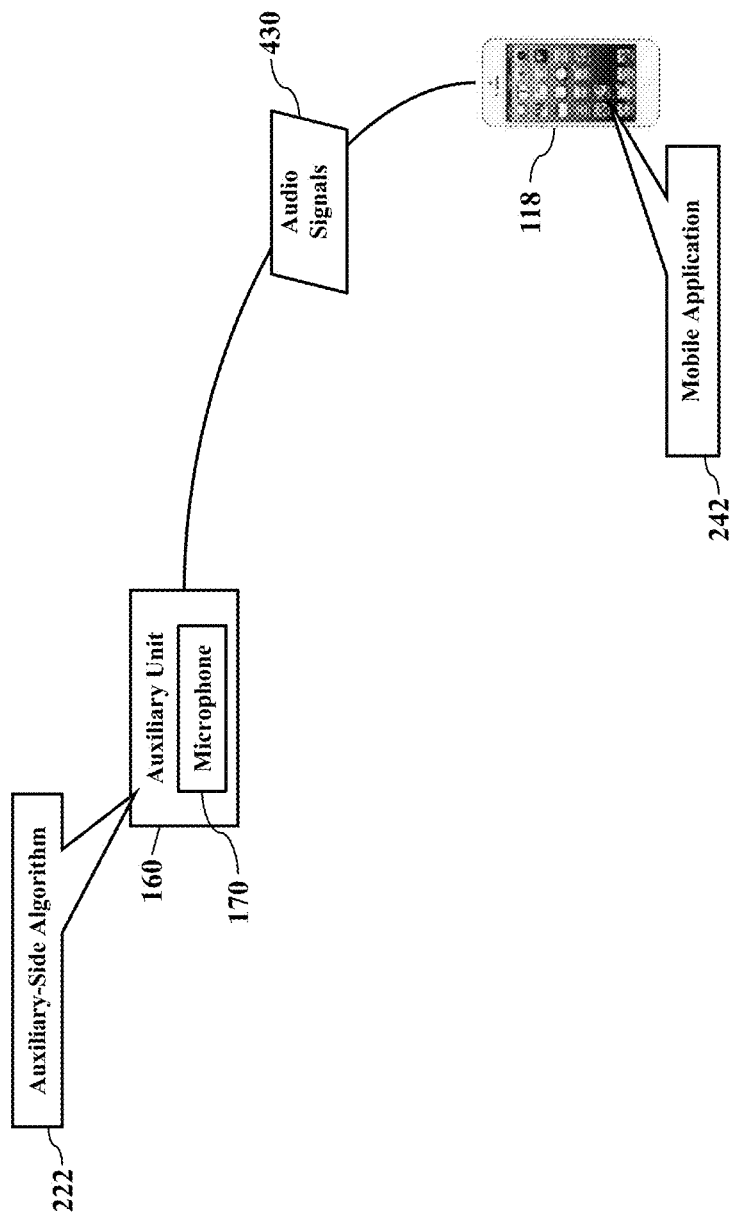
Figure 41:
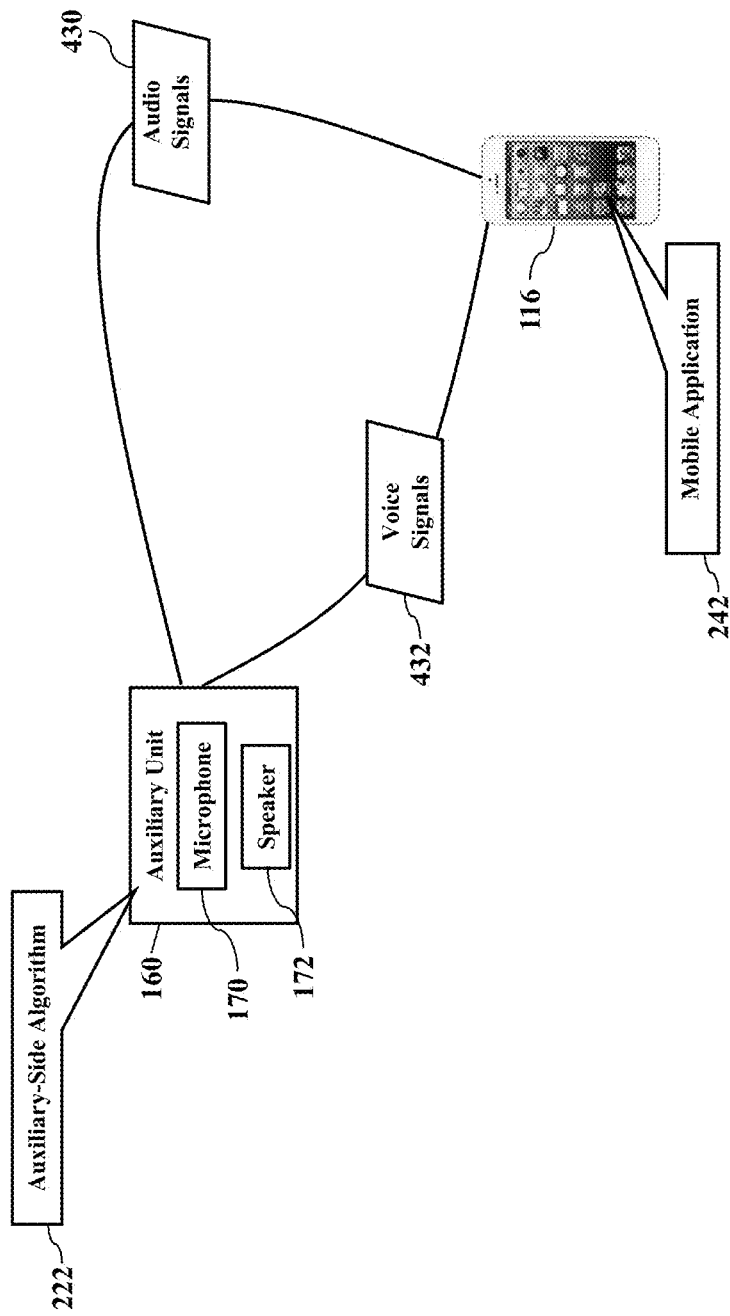
Figure 42:
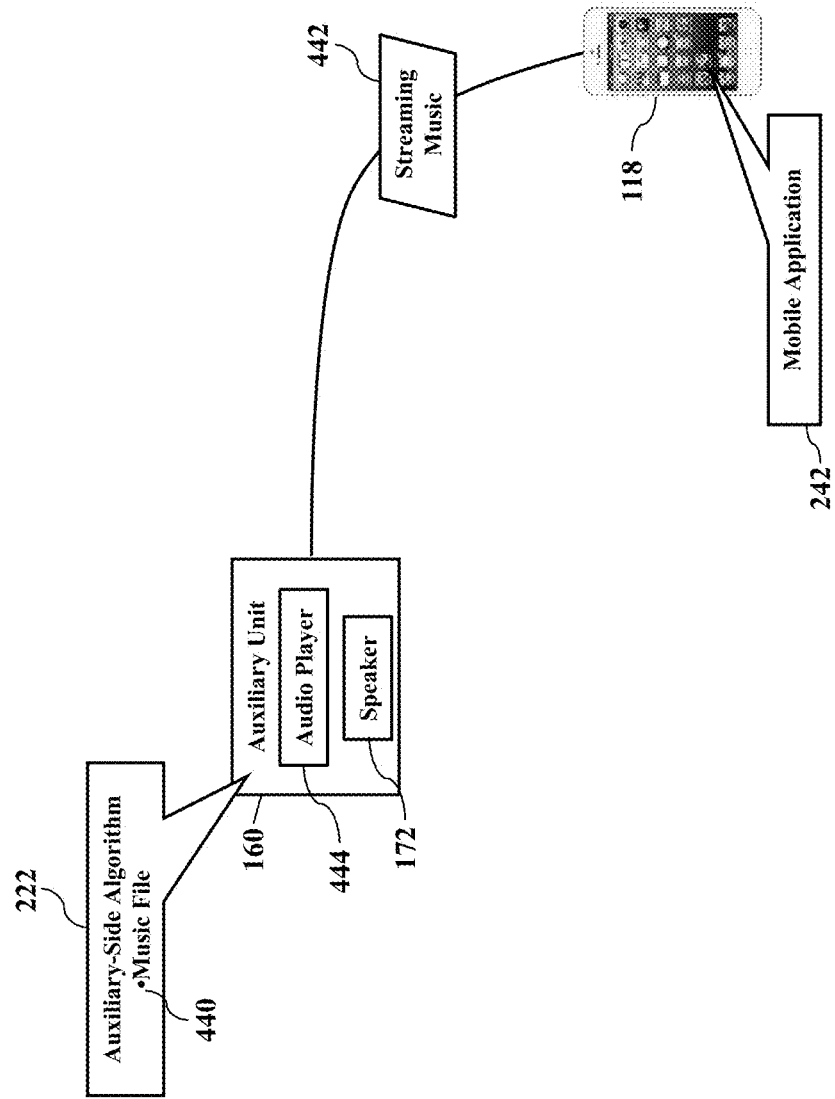
Figure 43:
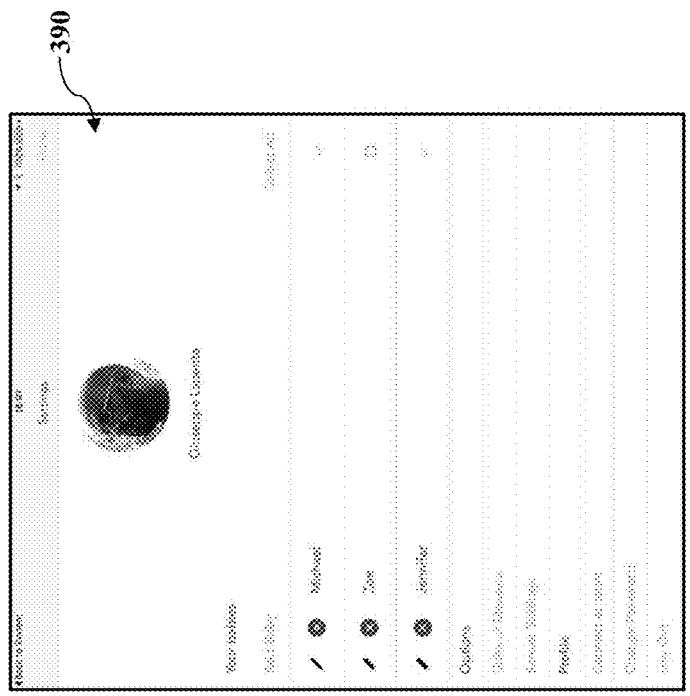
Figure 44:
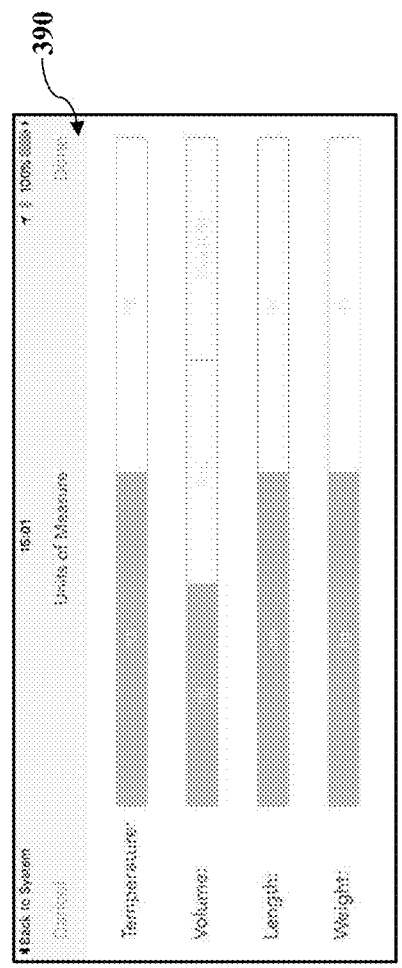
Figure 45:
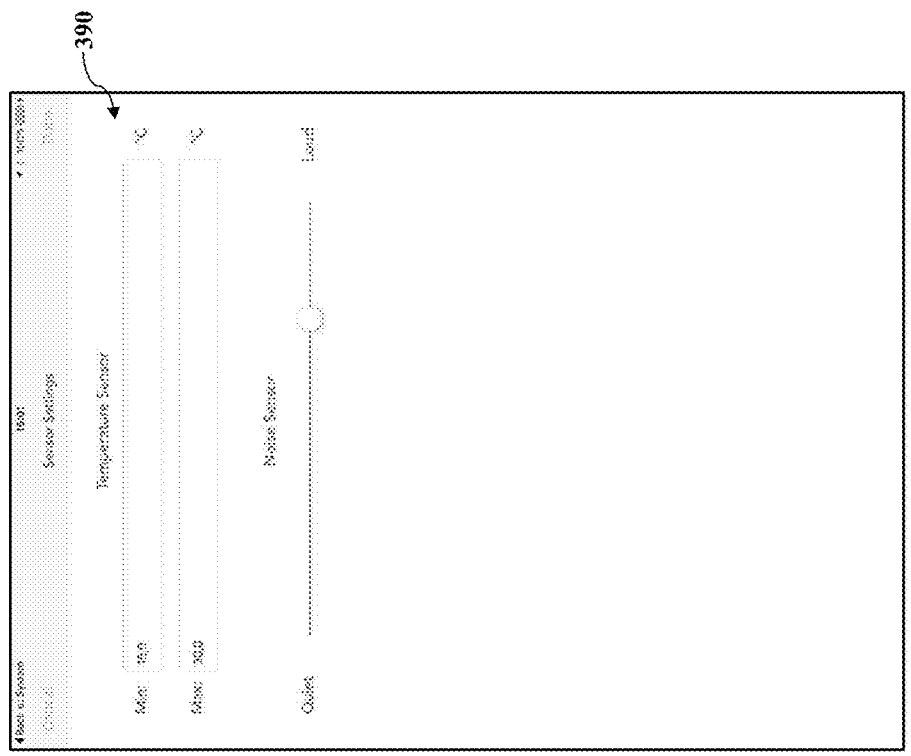
Figure 46:
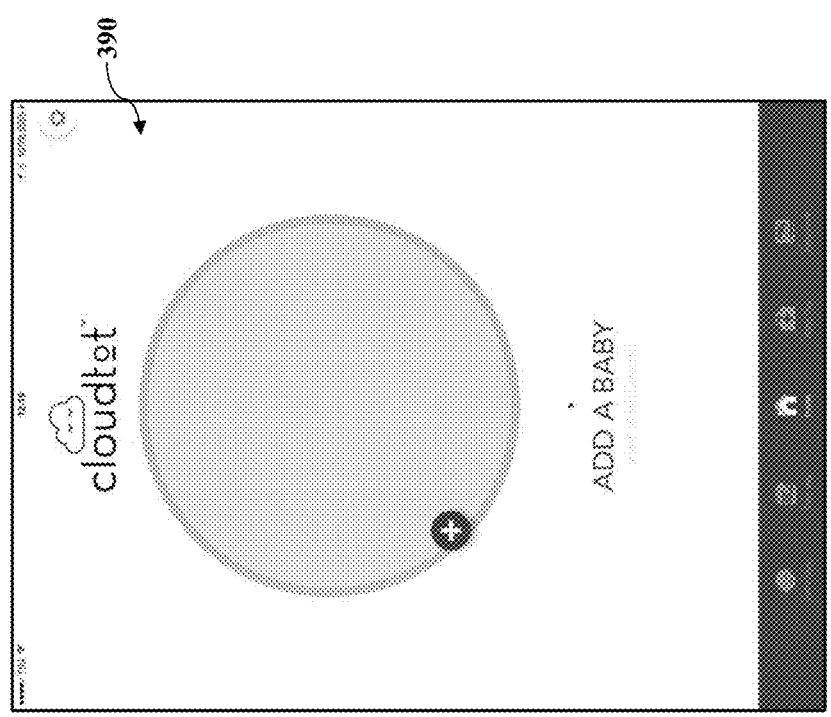
Figure 55:
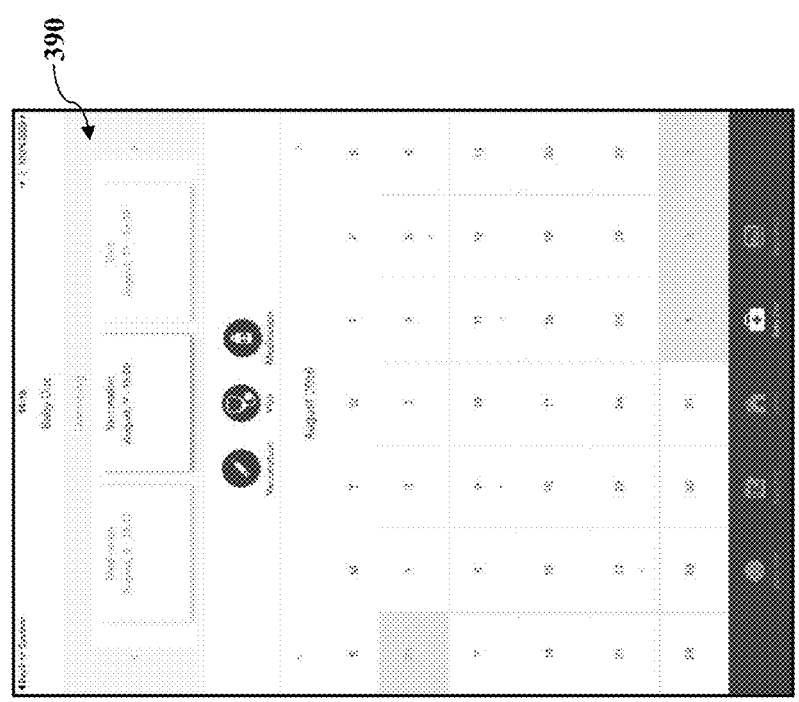
Figure 56:
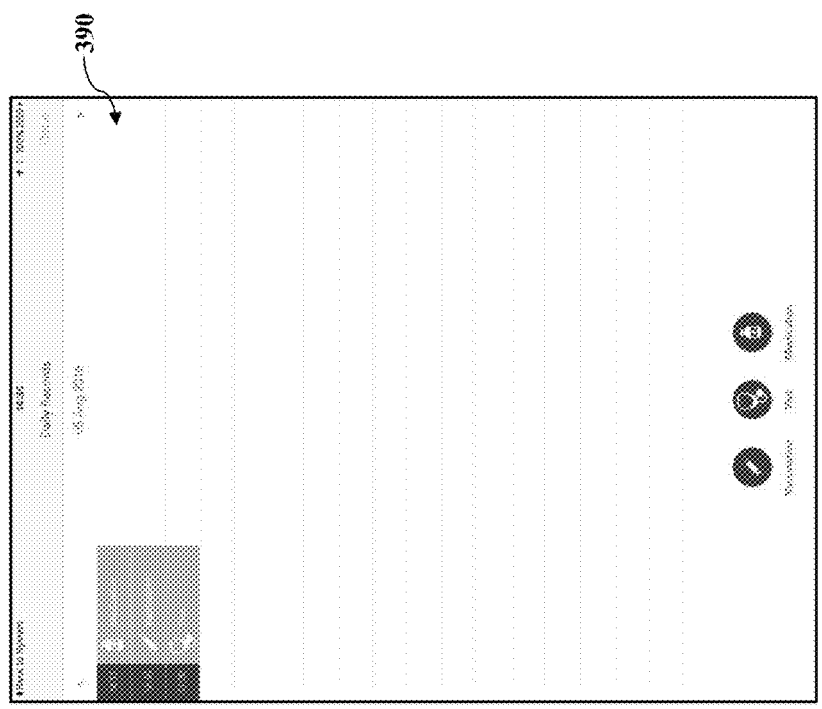
Figure 57:
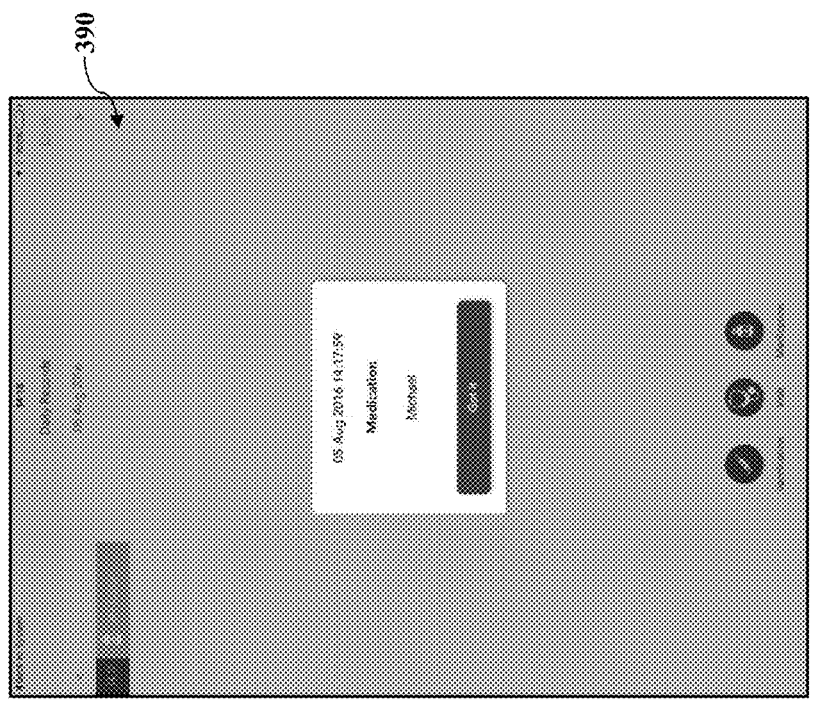
Figure 58:
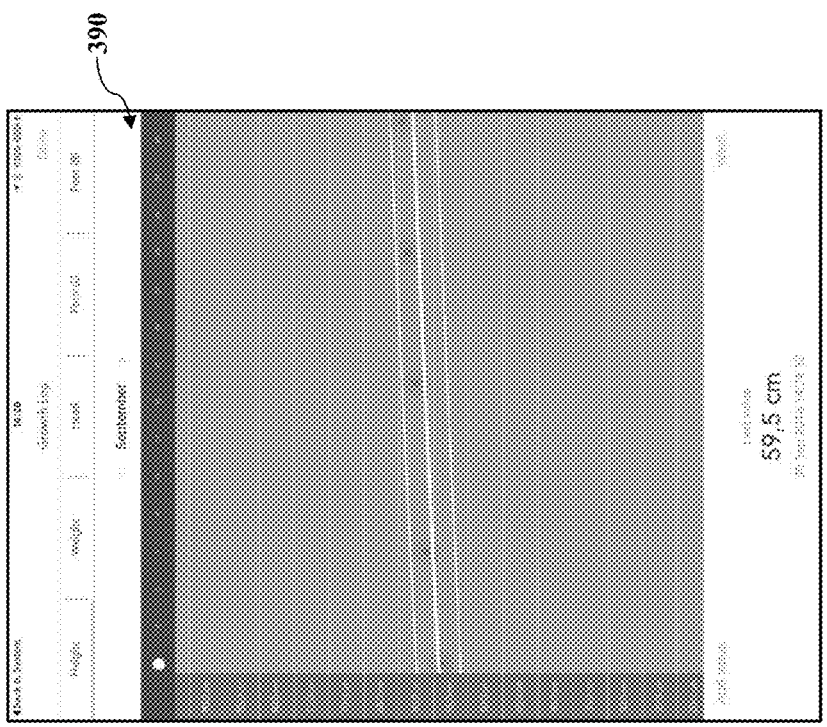
Figure 65:
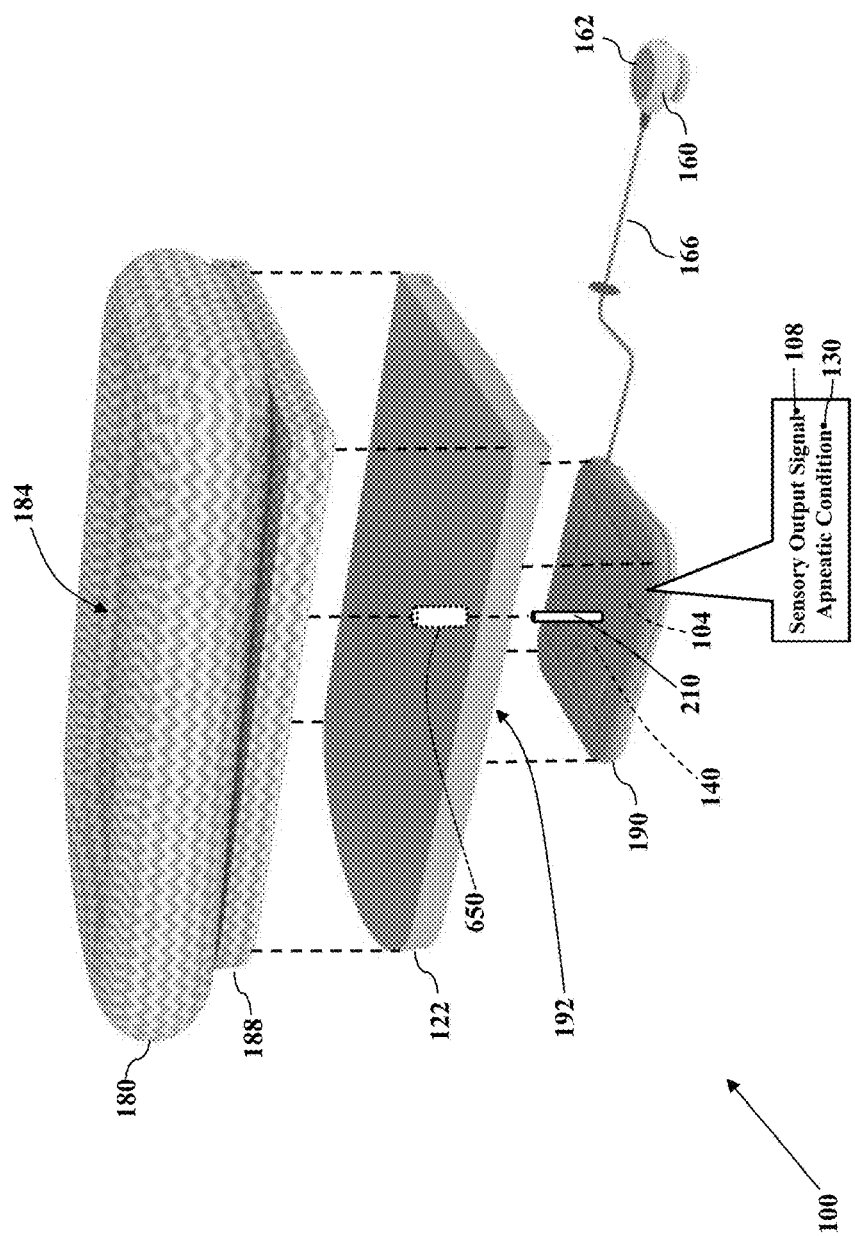
Figure 66:
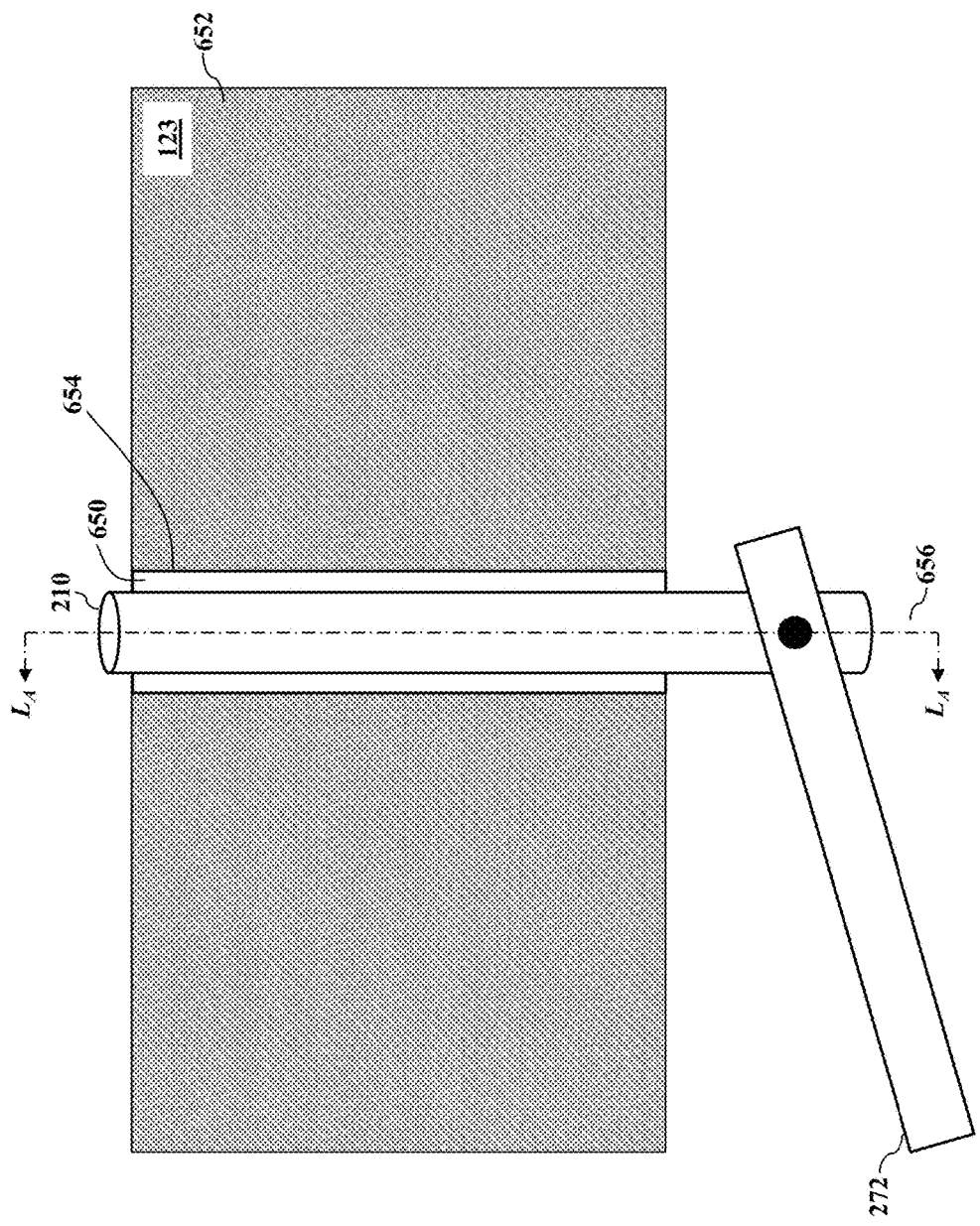
Figure 67:
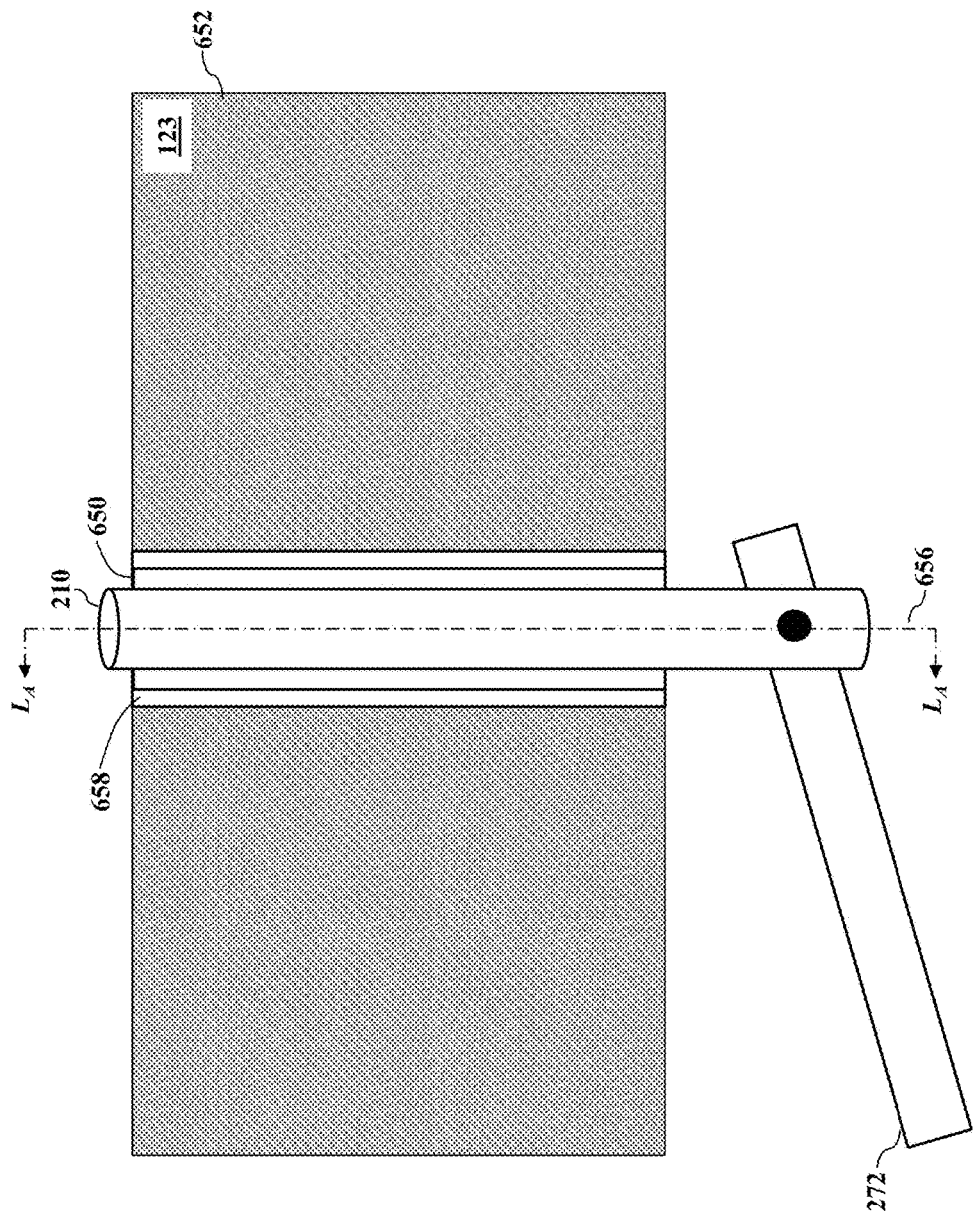
Figure 68:
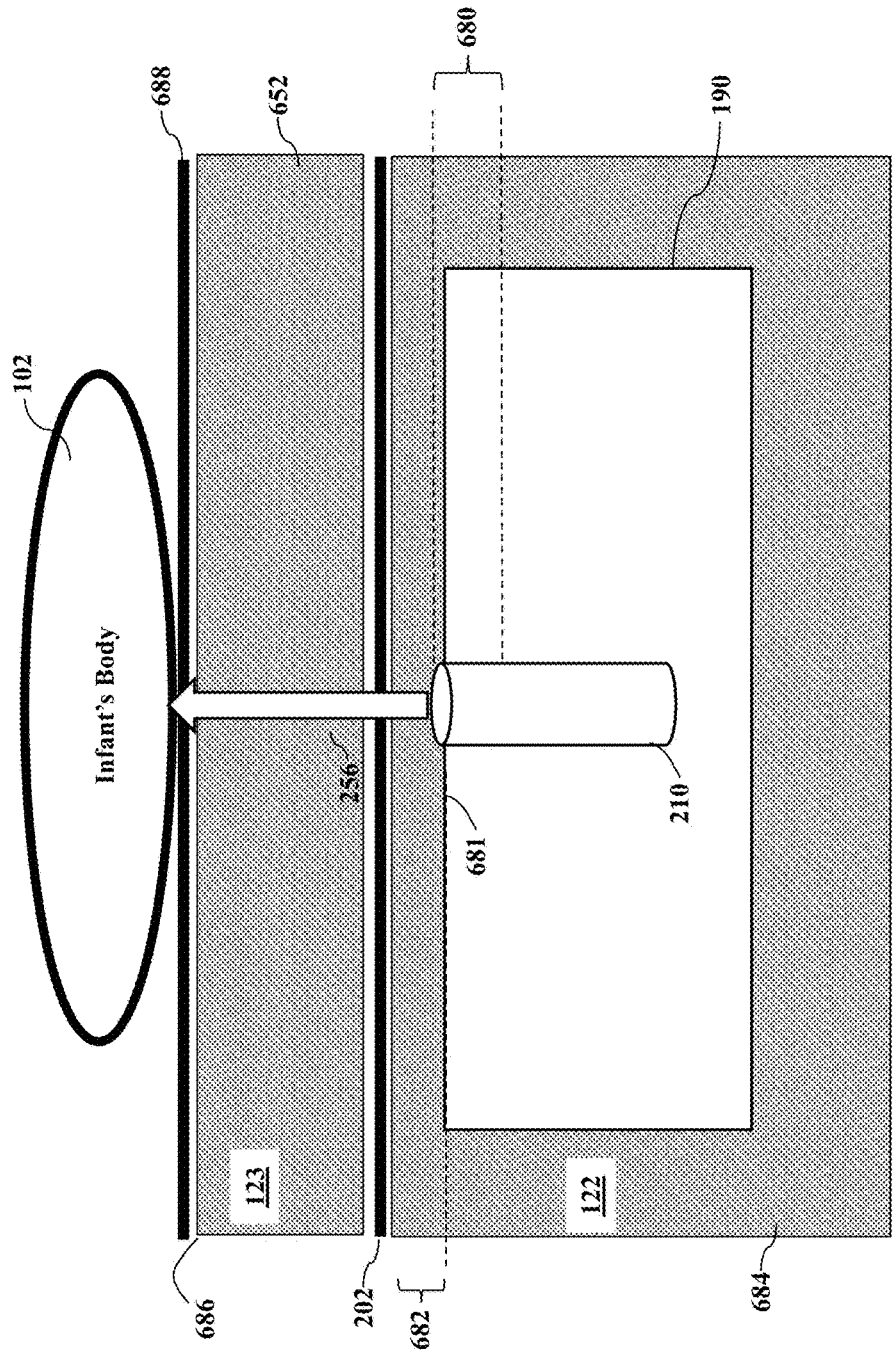
Figure 69:
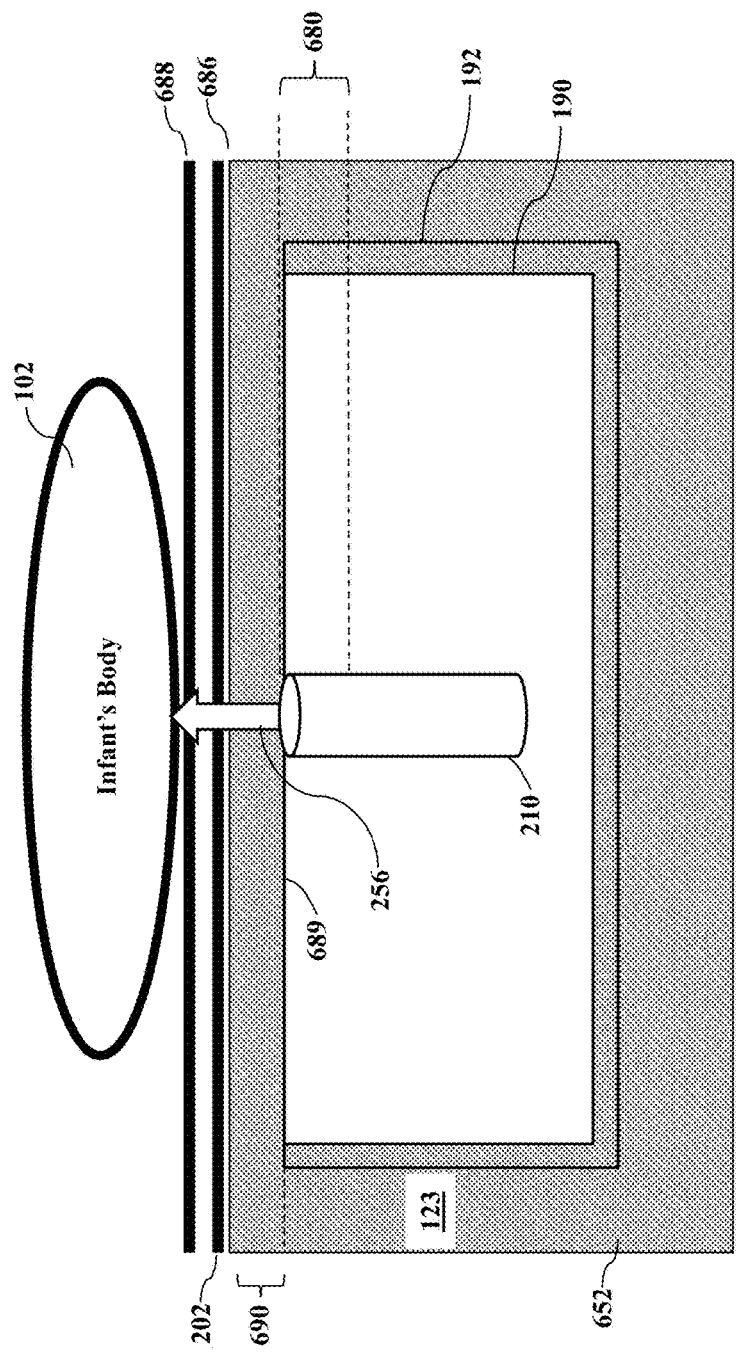

Having thus described the presently disclosed subject matter in general terms, reference will now be made to the accompanying Drawings, which are not necessarily drawn to scale, and wherein:

FIGS. 1-4 are simplified illustrations of a monitoring system, according to exemplary embodiments;

FIGS. 5-9 are more detailed illustrations of the monitoring system, according to exemplary embodiments;

FIGS. 10-13 illustrate conductive capabilities, according to exemplary embodiments;

FIG. 14 illustrates a mattress, according to exemplary embodiments;

FIG. 15 is a simple illustration of a contact mechanism, according to exemplary embodiments;

FIG. 16 is a detailed block diagram illustrating an operating environment, according to exemplary embodiments;

FIGS. 17-20 are more detailed illustrations of the contact mechanism, according to exemplary embodiments;

FIG. 21 illustrates remote activation, according to exemplary embodiments;

FIG. 22 illustrates an optional presence detection, according to exemplary embodiments;

FIGS. 23-24 illustrate a rest quality, according to exemplary embodiments;

FIG. 25 illustrates rest monitoring, according to exemplary embodiments;

FIG. 26 illustrates peg positioning, according to exemplary embodiments;

FIGS. 27-30 illustrate packaging considerations, according to exemplary embodiments;

FIGS. 31-32 are detailed illustrations of an auxiliary unit, according to exemplary embodiments;

FIGS. 33-35 illustrate local interpretation, according to exemplary embodiments;

FIGS. 36-39 illustrate remote interpretation, according to exemplary embodiments;

FIGS. 40-41 illustrate streaming audio, according to exemplary embodiments;

FIG. 42 illustrates musical capabilities, according to exemplary embodiments;

FIGS. 43-45 are screenshots illustrating parameter settings, according to exemplary embodiments;

FIGS. 46-50 are screenshots for manually adding infant users, according to exemplary embodiments;

FIGS. 51-54 are screenshots for establishing a baby book, according to exemplary embodiments;

FIGS. 55-57 are screenshots for calendric recordings, according to exemplary embodiments;

FIG. 58 is a screenshot illustrating logging capabilities, according to exemplary embodiments;

FIGS. 59-64 are screenshots illustrating electronic logs, according to exemplary embodiments;

FIGS. 65-67 are alternative configurations of the contact mechanism, according to exemplary embodiments;

FIGS. 68-69 illustrate linear translation, according to exemplary embodiments;

FIGS. 70-73 illustrate a suspension arch, according to exemplary embodiments; and FIGS. 74-77 are schematics further illustrating operating environments for additional aspects of the exemplary embodiments.

DETAILED DESCRIPTION

The exemplary embodiments will now be described more fully hereinafter with reference to the accompanying drawings. The exemplary embodiments may, however, be embodied in many different forms and should not be construed as limited to the embodiments set forth herein. These embodiments are provided so that this disclosure will be thorough and complete and will fully convey the exemplary embodiments to those of ordinary skill in the art. Moreover, all statements herein reciting embodiments, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure).

Thus, for example, it will be appreciated by those of ordinary skill in the art that the diagrams, schematics, illustrations, and the like represent conceptual views or processes illustrating the exemplary embodiments. The functions of the various elements shown in the figures may be provided through the use of dedicated hardware as well as hardware capable of executing associated software. Those of ordinary skill in the art further understand that the exemplary hardware, software, processes, methods, and/or operating systems described herein are for illustrative purposes and, thus, are not intended to be limited to any particular named manufacturer.

As used herein, the singular forms "a," "an," and "the" are intended to include the plural forms as well, unless expressly stated otherwise. It will be further understood that the terms "includes," "comprises," "including," and/or "comprising," when used in this specification, specify the presence of stated features, integers, steps, operations, elements, and/or components, but do not preclude the presence or addition of one or more other features, integers, steps, operations, elements, components, and/or groups thereof. It will be understood that when an element is referred to as being "connected" or "coupled" to another element, it can be directly connected or coupled to the other element or intervening elements may be present. Furthermore, "connected" or "coupled" as used herein may include wirelessly connected or coupled. As used herein, the term "and/or" includes any and all combinations of one or more of the associated listed items.

It will also be understood that, although the terms first, second, etc. may be used herein to describe various elements, these elements should not be limited by these terms. These terms are only used to distinguish one element from another. For example, a first device could be termed a second device, and, similarly, a second device could be termed a first device without departing from the teachings of the disclosure.

Figure 1:
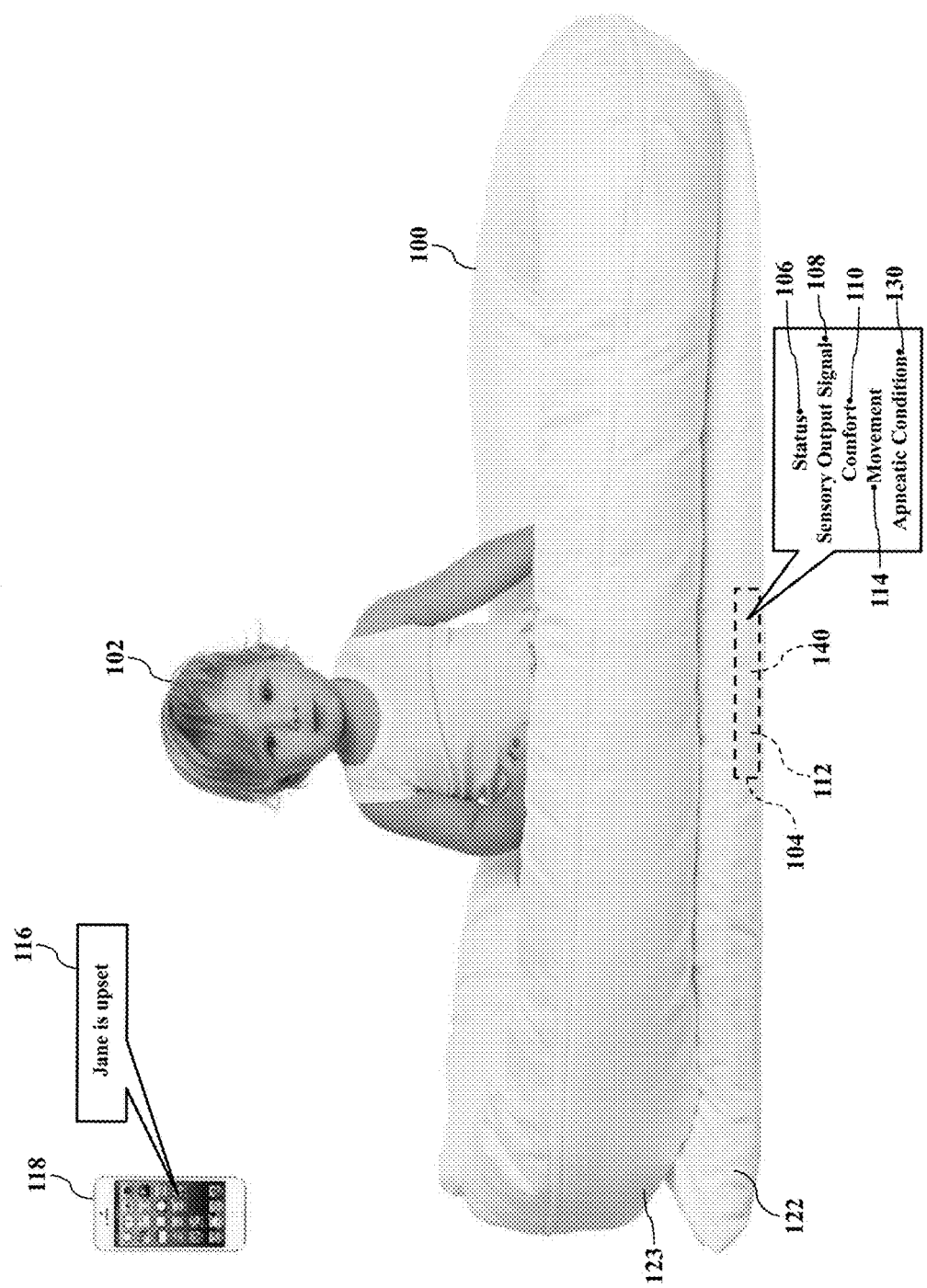

FIGS. 1-4 are simplified illustrations of a monitoring system 100, according to exemplary embodiments. While the monitoring system 100 may be adapted to any size of user (whether human or animal), FIG. 1 illustrates an infant 102 seated within the monitoring system 100. As the infant 102 moves, plays, and rests within the monitoring system 100, the monitoring system 100 has various sensors 104 and programming logic that monitor the infant's status 106. The sensors 104 may generate sensory output signals 108 that are used to infer the infant's status 106, such as his or her comfort 110. While the monitoring system 100 may have many different sensors 104 that monitor the infant 102, for simplicity FIG. 1 only illustrates a motion sensor 112. The motion sensor 112 generates the sensory output signal 108 representing a movement 114 associated with the infant 102. Exemplary embodiments may even recommend parental action in response to the movement 114, such as generating a notification 116 at the parent's smartphone 118 (as later paragraphs will explain).

Exemplary embodiments may even detect the infant's breathing. The motion sensor 112 may detect the infant's respiratory movements within the monitoring system 100. That is, as the infant 102 sits or lies within the monitoring system 100, the motion sensor 112 may detect expansion and contraction of the infant's chest cavity. As the infant inhales and exhales, a padded surface (such as a cushioned pad 122 and/or a mattress 123) slightly expands and contracts. Because the motion sensor 112 is proximally located to the infant 122, the motion sensor 112 responds to movements 114 and generates its corresponding sensory output signal 108. For example, the motion sensor 112 may be housed in a housing, such as housed between two thin layers (e.g., about 1.5 mm in thickness) of rigid or semi-rigid material, such as polypropylene or the like, and placed within, or under, the cushioned pad 122 or mattress 123, or within a cavity formed therein. In another example, motion sensor 112 may physically touch or contact the cushioned pad 122 and/or mattress 123. When the infant 102 moves, the motion sensor 112 responds to any physical property or manifestation induced within, or propagated through, the cushioned pad 122 and/or the mattress 123. Exemplary embodiments may then infer the infant's comfort 110 based on the sensory output signal 108. For example, if the sensory output signal 108 exhibits small, repetitive values, then perhaps the infant's respiration indicates calm rest. However, if the sensory output signal 108 has quickly changing values, the infant 102 may be nervously panting. Exemplary embodiments may thus infer the infant's comfort 110 based on the sensory output signal 108 generated by the motion sensor 112. Exemplary embodiments may even report the comfort 110 to a remote location, such as the parent's smartphone 118.

Exemplary embodiments may also infer an apneatic condition 130. As the reader may understand, sleep apnea is a common occurrence in adults. Apnea is also unfortunately common in infants and may even cause asphyxiation. Here, then, exemplary embodiments may alarm and notify when the infant 102 pauses or stops breathing for some period of time outside of a threshold value. If the infant 102 ceases breathing, even momentarily, the sensory output signal 108 may fall below a threshold value at which the apneatic condition 130 is assumed. Exemplary embodiments may thus send the notification 116 to the parent's smartphone 114, to emergency personnel, and/or to any other address. Exemplary embodiments may even activate a contact mechanism 140 to jolt or nudge the cushioned pad 122, the mattress 123, or even the infant 102 to promote a resumption of breathing (as later paragraphs will explain). In one example, the threshold value may be a time period of twelve (12) seconds. The threshold value may alternatively be a time period greater or less than (12) seconds.

The motion sensor 112 may utilize any sensing technology. There are many schemes and techniques for sensing the movements 114 of the user lying within the monitoring system 100, and exemplary embodiments are agnostic and may use any of the schemes and techniques. Exemplary embodiments, though, may preferably use the piezoelectric effect to sense the user's movements 114. The motion sensor 112, in other words, may have a piezoelectric material, film, or mass that generates or changes electrical charge or voltage in response to the user's movements 114 (e.g., pressure, acceleration, strain, and/or force). The motion sensor 112, in particular, may utilize a piezoelectric disk that deflects, deforms, or compresses in response to the infant's movements 114. The piezoelectric disk, for example, may be incorporated within the cushioned pad 122 and/or within the mattress 123 (as later paragraphs will explain). Because the piezoelectric disk is preferably oriented or arranged underneath the infant 102, the infant's movements 114 propagate along and/or through the cushioned pad 122 and/or the mattress 123 to deflect the piezoelectric disk. The motion sensor 112 thus detects the resulting electrical charge or voltage in the piezoelectric disk and generates the sensory output signal 108. The motion sensor 112 may also utilize a mass accelerometer that detects the infant's movements in relation to gravity. Regardless, the piezoelectric effect and motion sensing is generally well known and need not be further explained.

Figure 2:
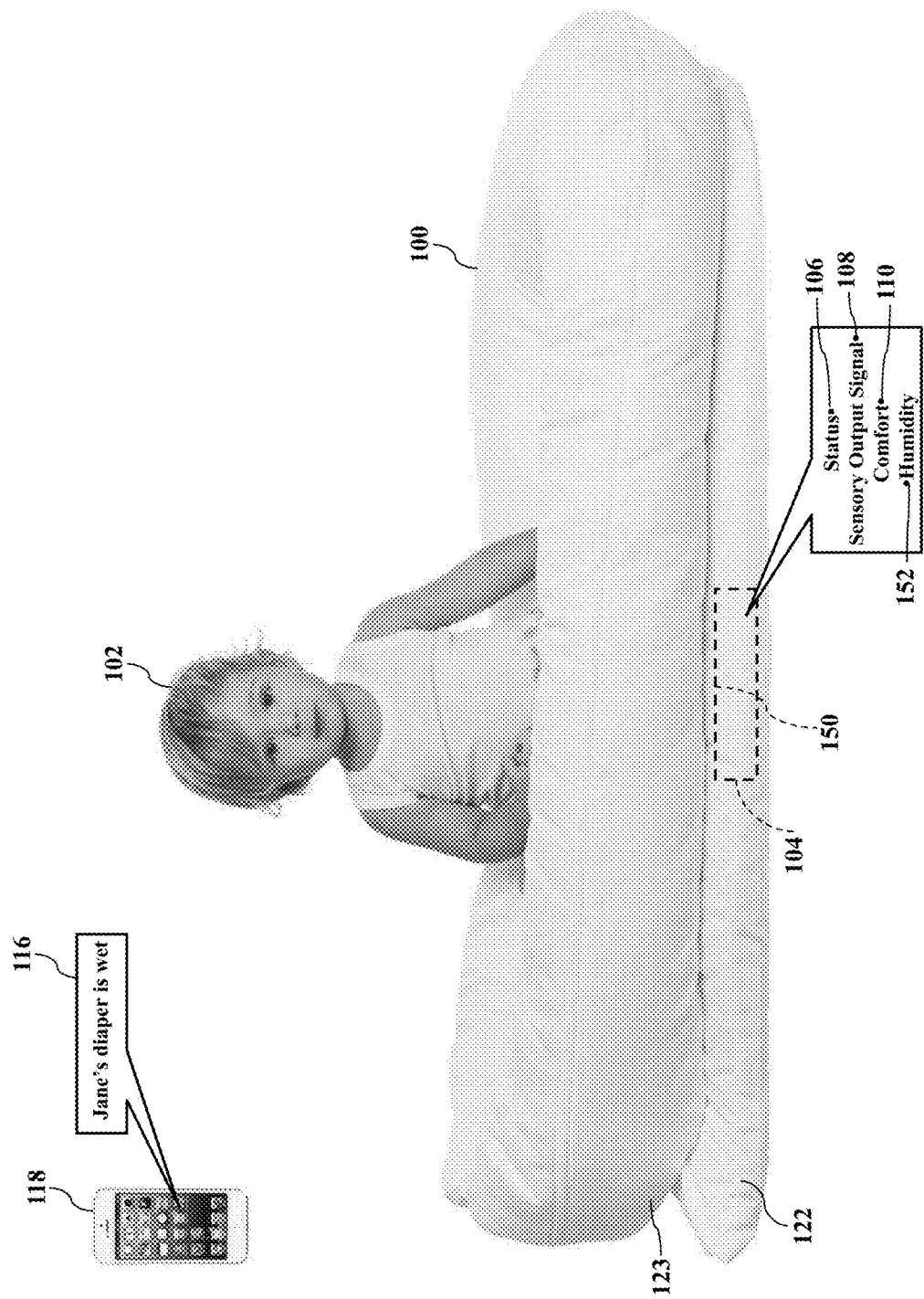

FIG. 2 illustrates a humidity sensor 150. The humidity sensor 150 may be another one of the sensors 104 that monitors the infant 102 sitting or lying within the monitoring system 100. While the humidity sensor 150 may be positioned anywhere within the monitoring system 100, FIG. 2 illustrates a proximal location beneath the infant 102. For example, the humidity sensor 150 may be located between a top surface of the cushioned pad 122 or mattress 123 and an outer cover of thereof, may be integrated with a top surface of the cushioned pad 122 or mattress 123, or may be integrated with a top surface of the outer cover of the cushioned pad 122 or mattress 123. The humidity sensor 150 generates the sensory output signal 108 representing a humidity 152 associated with the infant 102. Exemplary embodiments may thus use the sensory output signal 108 (representing the humidity 152) to infer that the infant 102 is sweaty, nervous, emotionally upset, and/or has a wet/soiled diaper. Indeed, should the humidity 152 exceed a threshold value, exemplary embodiments may infer that the infant has vomited, sweated, urinated, or soiled his or her clothing. Exemplary embodiments may thus recommend parental action in response to the humidity 152, such as generating the notification 116 at the parent's smartphone 118 for diaper replacement (again as later paragraphs will explain). While the humidity sensor 150 may utilize any sensor technology, exemplary embodiments may preferably use a conductive fabric, which later paragraphs will explain.

Figure 3:
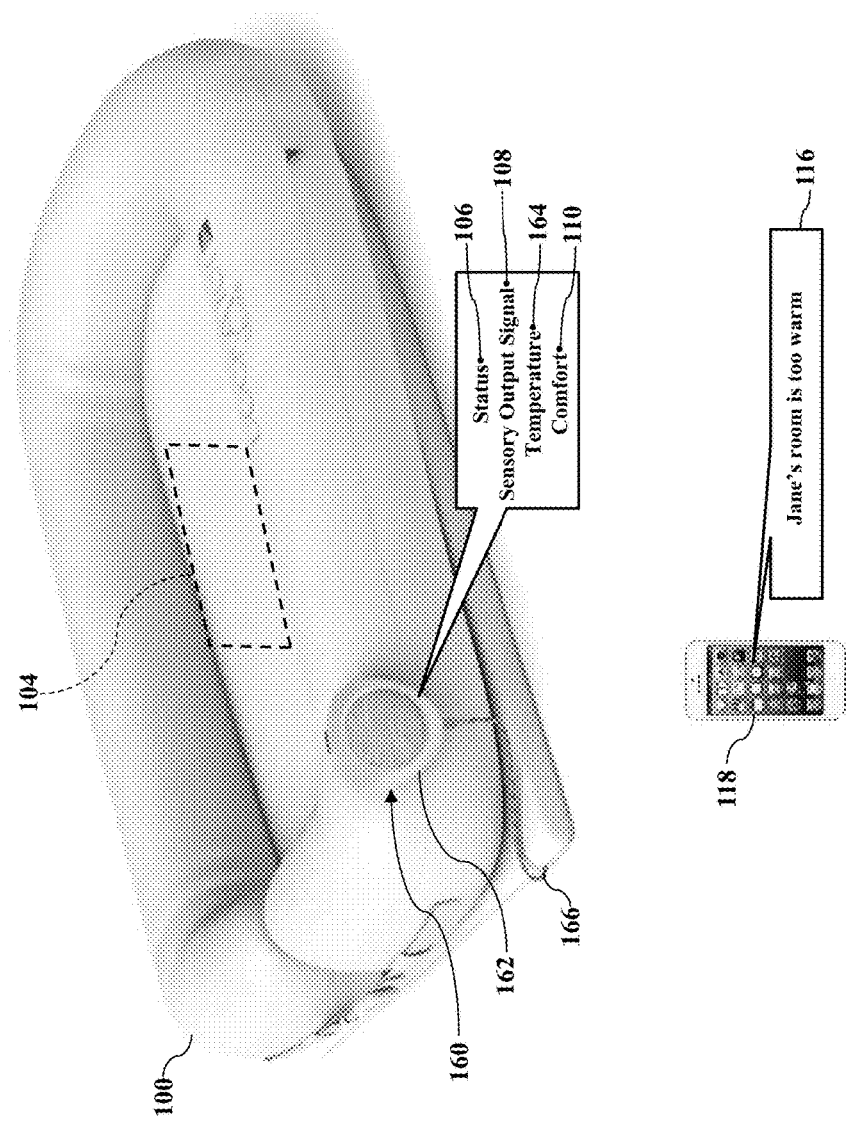

FIG. 3 illustrates an isometric view of the monitoring system 100. Here the monitoring system 100 may include an auxiliary unit 160. The auxiliary unit 160 interfaces with the sensor(s) 104 to provide still more monitoring capabilities. For example, the auxiliary unit 160 may include a temperature sensor 162. The temperature sensor 162 may generate the sensory output signal 108 representing an ambient temperature 164 associated with the environment of the infant 102 (illustrated in FIGS. 1-2). The auxiliary unit 160 may thus be placed in proximity to the infant 102 to measure the ambient temperature 164. The temperature sensor 162 has a sensory element (such as a transducer, not shown for simplicity) that generates one of the sensory output signals 108 representing the ambient temperature 164 associated with the infant's environment. FIG. 3 illustrates a corded embodiment, in which the auxiliary unit 160 connects via a physical cable 166 to the internal sensors 104. While the auxiliary unit 160 may wirelessly interface with the sensors 104, the physical cable 166 may prevent or help to prevent the auxiliary unit 160 from being lost or separated from the monitoring system 100. Alternatively, the physical cable 166 may not be required and auxiliary unit 160 may interface with the sensor(s) 104 completely wirelessly. Regardless, the temperature sensor 162 may be used to infer the infant's comfort 110 (such as too warm or too cold), which may be remotely reported to the parent's smartphone 118.

Figure 4:
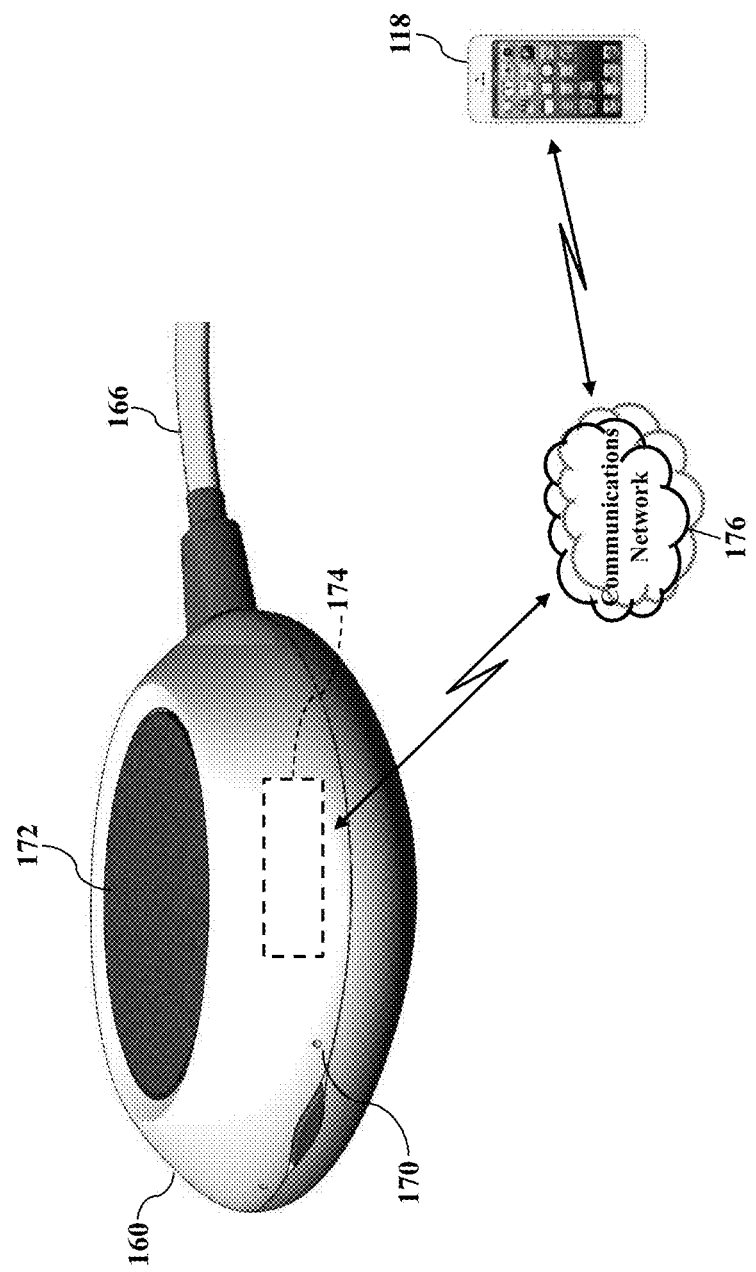

FIG. 4 illustrates additional monitoring capabilities. Here the auxiliary unit 160 may include a microphone 170, a speaker 172, and/or a network interface 174 to a communications network 176. The microphone 170 senses audible sounds in the vicinity of the user (such as the infant 102 illustrated in FIGS. 1-2), including the user's own voice. The speaker 172 audibly reproduces sounds in the vicinity of the infant 102. The network interface 174 allows the auxiliary unit 160 to communicate with any remote device, such as the smartphone 118. The auxiliary unit 160 may thus wirelessly transmit speech signals (associated with the microphone 170) via the communications network 176 to any destination (such as the parent's or caregiver's smartphone 118). The auxiliary unit 160 may also wirelessly receive voice signals sent via the communications network 176 from the smartphone 118 for reproduction by the speaker 172. The parent or caregiver may thus remotely converse with the infant lying within the monitoring system (illustrated as reference numeral 100 in FIGS. 1-3). The speaker 172 also allows the auxiliary unit 160 to receive and/or to play a music file, thus allowing exemplary embodiments to sooth and comfort the user.

Figure 5:
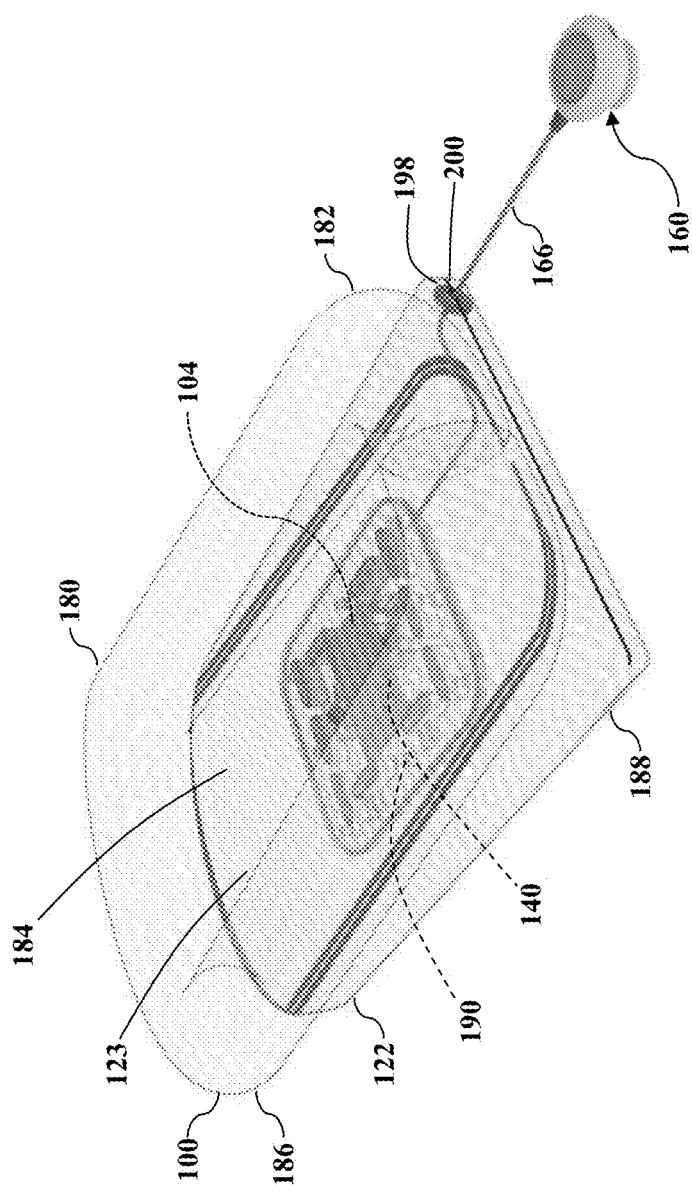

FIGS. 5-9 are more detailed illustrations of the monitoring system 100, according to exemplary embodiments. FIG. 5, for example, illustrates a transparent, assembled view of the monitoring system 100. The monitoring system 100 has an upper textile product 180 with a generally rectangular or oval shape. The textile product 180 has one or more sidewalls 182 substantially defining an interior portion 184 in which the user (such as the infant 102 illustrated in FIGS. 1-2) sits, plays, and rests. The sidewalls 182 have a height above a floor chosen to safely confine the infant 102. The textile product 180 may have an outer shell 186 filled with a soft, comfortable material (such as foam, cotton, or other fiber). The textile product 180 may have a pocket 188 (which may be zipperable), into which the cushioned pad 122 inserts. The mattress 123, if desired or included, may have a material thickness that provides additional bottom cushioning.

Figure 6:
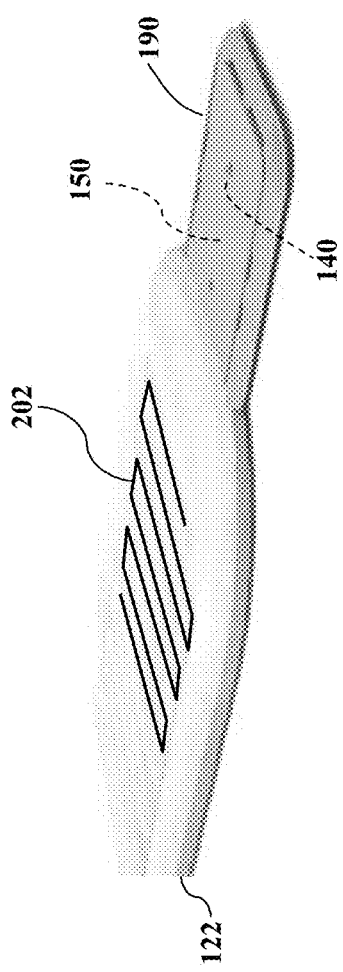

Exemplary embodiments may include an internal unit 190. The internal unit 190 may contain the contact mechanism 140. FIG. 6 illustrates the internal unit 190 sliding into the cushioned pad 122. The cushioned pad 122 may thus be a sleeve having a closable or zippered access or aperture that allows insertion and removal of the internal unit 190. The cushioned pad 122 may also include the humidity sensor 150. Again, while the humidity sensor 150 may utilize any sensor technology, FIG. 6 illustrates conductive strands 202 that electrically conduct current and voltage. The conductive strands 202 may be integrated into an upper surface or covering of the cushioned pad 122. The cushioned pad 122 may thus be a conductive sleeve that encases the internal unit 190. Later paragraphs will further explain the humidity sensor 150 and the conductive strands 202.

Figure 7:
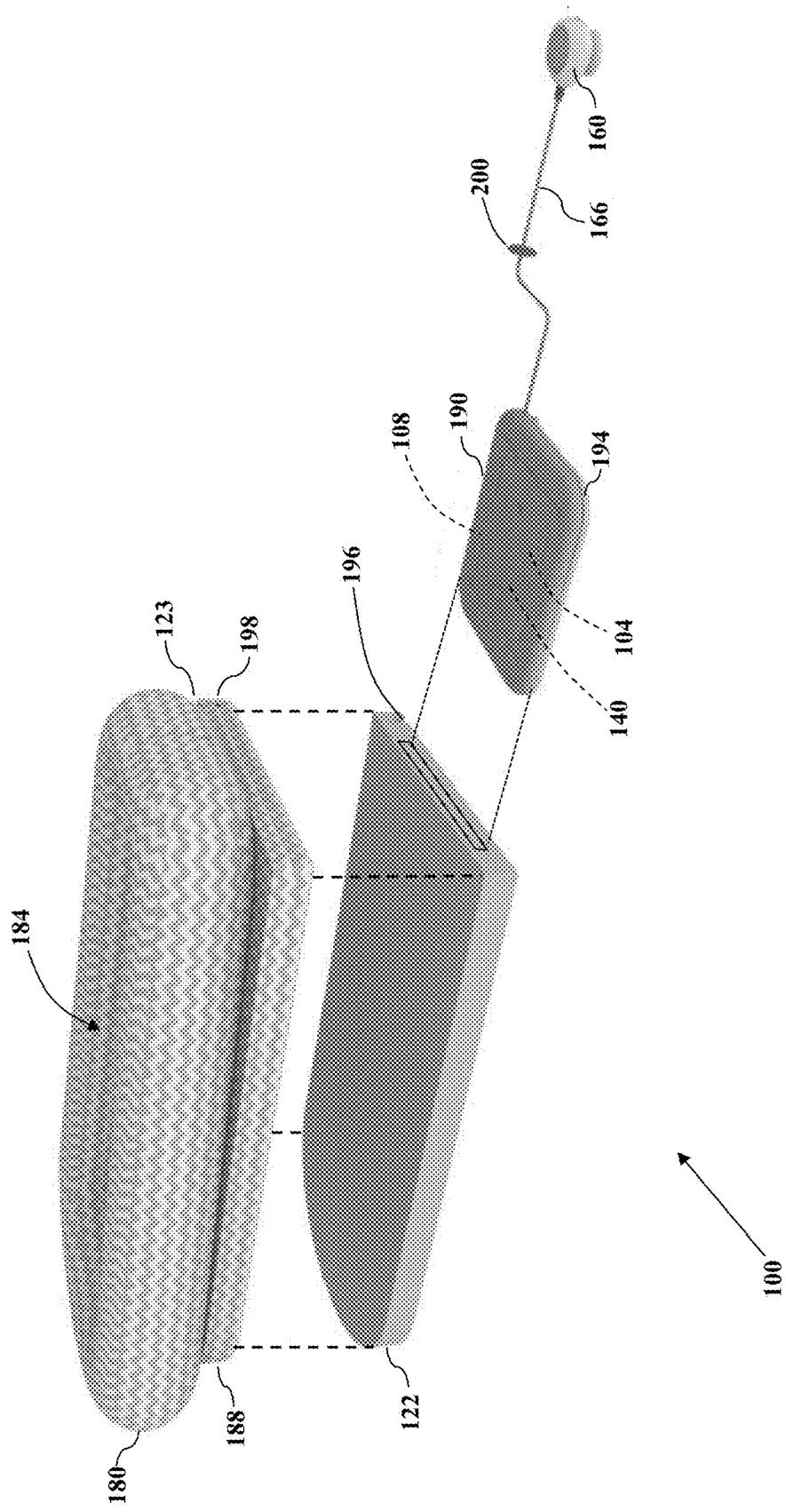

FIG. 7 illustrates an exploded view of some componentry. The internal unit 190 has an outer enclosure 194 and slides into the cushioned pad 122 or mattress 123. The cushioned pad 122 or mattress 123 (having the internal unit 190) may then insert into the pocket 188. When the user (such as the infant 102 illustrated in FIGS. 1-2) sits, plays, and rests within the interior portion 184, the internal unit 190 is thus aligned or arranged underneath the user for optimum sensory perception and performance. Because the internal unit 190 may contain any of the sensors 104 (such as the motion sensor 112 and/or the humidity sensor 150 illustrated in FIGS. 1-2), the internal unit 190 is able to monitor the user's movements and wetness. Exemplary embodiments may even activate the contact mechanism 140, in response to the sensory output signals 108 generated by the motion sensor 112 and/or the humidity sensor 150.

Figure 8:
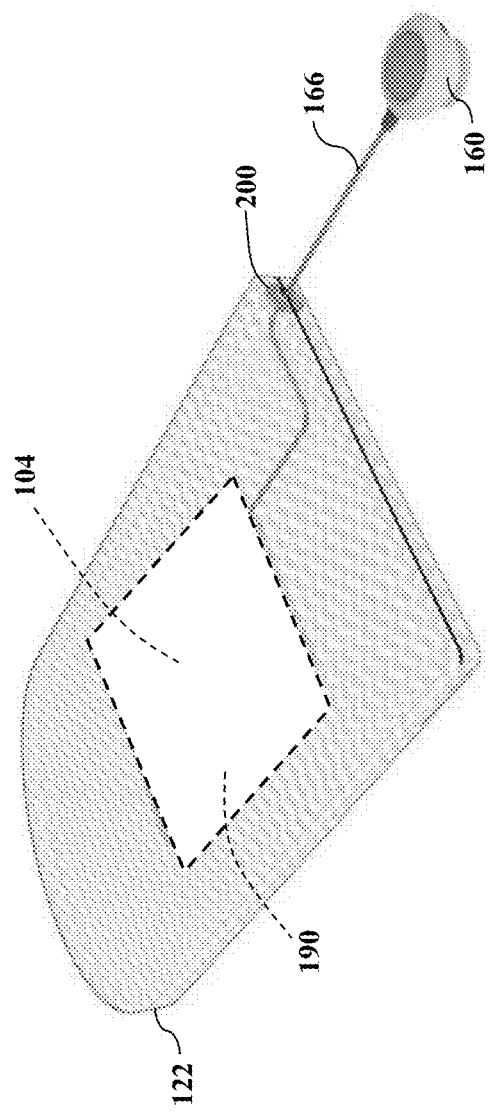

FIGS. 7-8 illustrate other features. The cushioned pad 122 or mattress 123 may have an internal channel 196 through which the physical cable 166 to the auxiliary unit 160 is routed or inserted. The outer shell 186 and/or the pocket 188 may also have a corresponding aperture 198 through which the physical cable 166 passes. The cushioned pad 122 or mattress 123 may thus internally contain at least some of the sensors 104 that help infer the infant's status 106. A stopper or plug 200 inserts into the internal channel 196 in the cushioned pad 122 or mattress 123, and the stopper or plug 200 is sized and shaped to help prevent the physical cable 166 from being over extended or tugged and thus damaging the internal unit 190. Alternatively, the internal unit 190 houses only the motion sensor 112.

Figure 9:
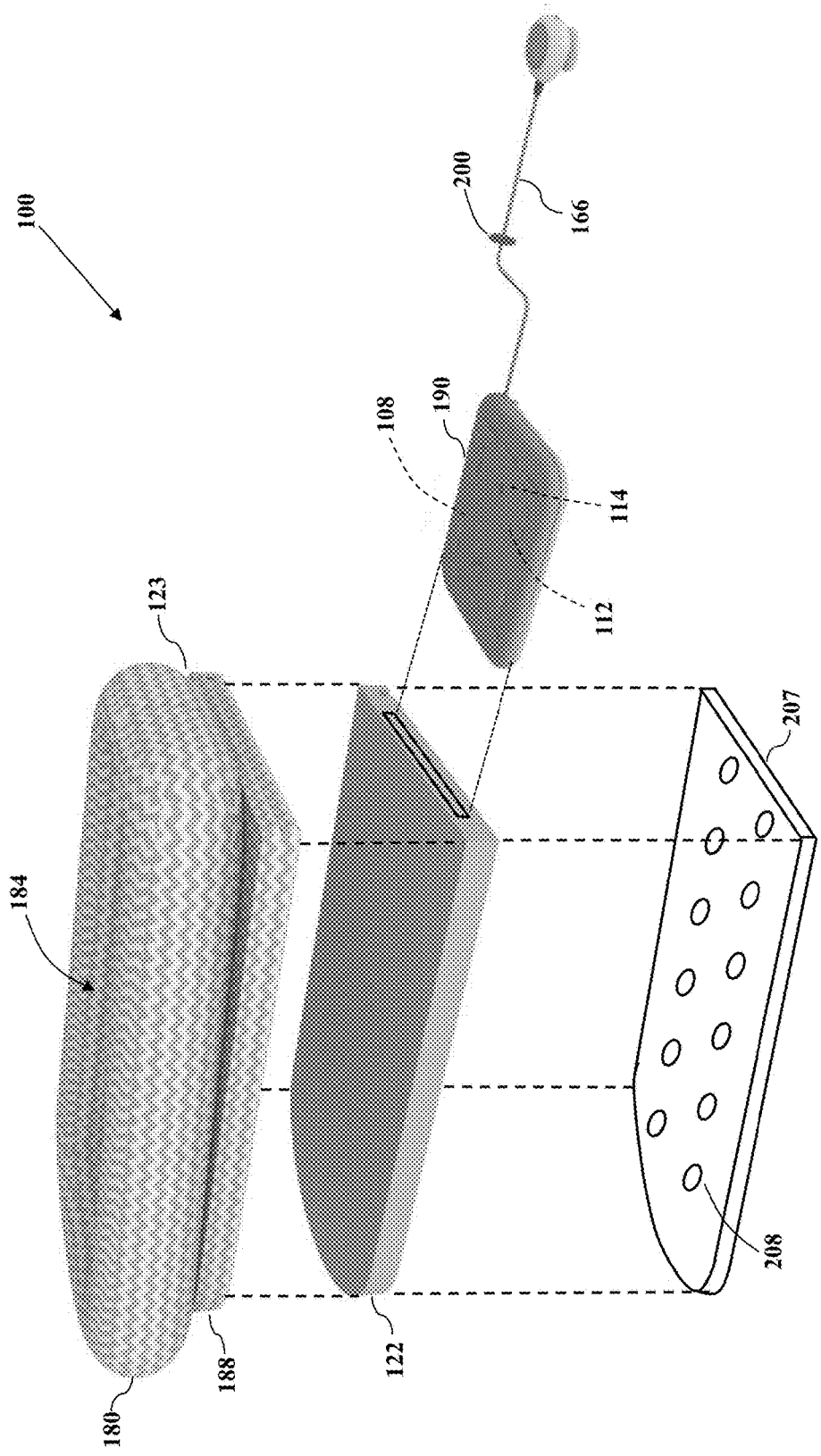

FIG. 9 illustrates an optional stabilizer 207. The stabilizer 207 may aid the motion sensor 112 in detecting the movements 114 of the user sitting or lying within the interior portion 184 of the monitoring system 100. As this disclosure above explained, the monitoring system 100 may include the motion sensor 112 that generates the sensory output signal 108 representing the movement 114 associated with the infant 102. However, testing has shown that motion sensitivity may be reduced on soft surfaces. That is, when the monitoring system 100 sits on carpet, a bed, or other relatively soft surface, the infant's movements 114 may be dampened and possibly not sufficiently detected by the motion sensor 112. The stabilizer 207 is thus a relatively rigid component that helps provide consistent detection of the infant's movements 114. While the stabilizer 207 may have any shape, FIG. 9 illustrates the stabilizer 207 as a flat, longitudinal plate that is placed or arranged below the cushioned pad 122. The stabilizer 207 thus lies below the internal unit 190 but atop a soft or irregular surface (again, such as carpet flooring or a bed). The stabilizer 207 thus provides a rigid bearing surface that promotes more constant values of the sensory output signal 108 generated by the motion sensor 112. The stabilizer 207 may thus be an optional component for improved performance in some situations.

As FIG. 9 also illustrates, the stabilizer 207 may have additional features. As the reader may envision, the stabilizer 207 may have a size and shape that is too cumbersome for some people. The stabilizer 207 may thus be molded from a lightweight plastic or polymer material to aid manual handling. Moreover, the stabilizer 207 may have holes, voids, or apertures 208 molded or drilled through its material thickness. These holes, voids, or apertures 208 also reduce material weight (and cost), thus making the stabilizer 207 easier to insert and to remove. The size (width and length) and material thickness may be chosen for best signal stabilization and ease of use. The stabilizer 207 may also have alignment features that insert into, or align with, the cushioned pad 122 or mattress 123.

Figure 10:
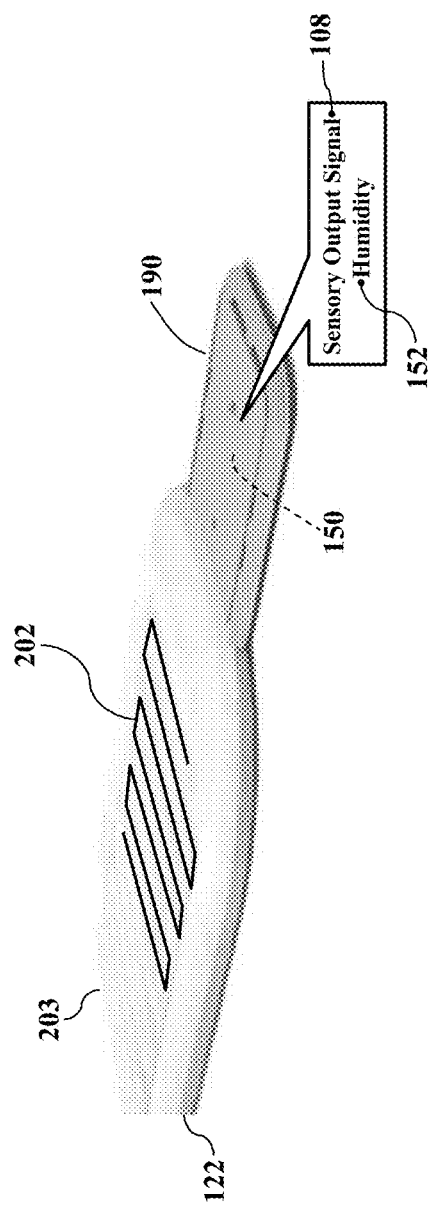

FIGS. 10-13 illustrate conductive capabilities, according to exemplary embodiments. As this disclosure earlier explained, exemplary embodiments may incorporate one or more of the conductive strands 202 that electrically conduct electrical power (e.g., current and voltage). These conductive strands 202 may aid the humidity sensor 150 in determining the humidity 152 associated with the infant 102 (illustrated in FIGS. 1-2) lying or sitting within the monitoring system 100. FIG. 10, for example, illustrates the conductive strands 202 woven or embroidered into the cushioned pad 122 (or mattress 123). Because the humidity sensor 150 may electrically conduct current and voltage, the cushioned pad 122 or mattress 123 may include a conductive textile 203 having one or more of the conductive strands 202 to aid sensory capabilities. For example, the humidity sensor 150 may apply or convey electrical voltage and/or current via the conductive strands 202 to determine the humidity 152. The conductive strands 202 may electrically connect to the internal unit 190 (perhaps via a cable with male/female connectors, not shown for simplicity), thus allowing the humidity sensor 150 to read or measure current, voltage, capacitance, and/or resistance conveyed by the conductive strands 202. The humidity sensor 150 thus receives or generates the sensory output signals 108 conveyed via, or determined from, the conductive strands 202 to infer the humidity 152 associated with the infant 102. While the conductive strands 202 may be located at any location or position, FIG. 10 illustrates the conductive strands 202 integrated within an upper (perhaps quilted) surface of the cushioned pad 122 (or mattress 123). That is, the conductive strands 202 may need to be only woven or embroidered within a central region of the cushioned pad 122 or mattress 123. Exemplary embodiments may thus include the conductive strands 202 as the smart conductive textile 203 for inferring or measuring the humidity 152 associated with the user.

Figure 11:
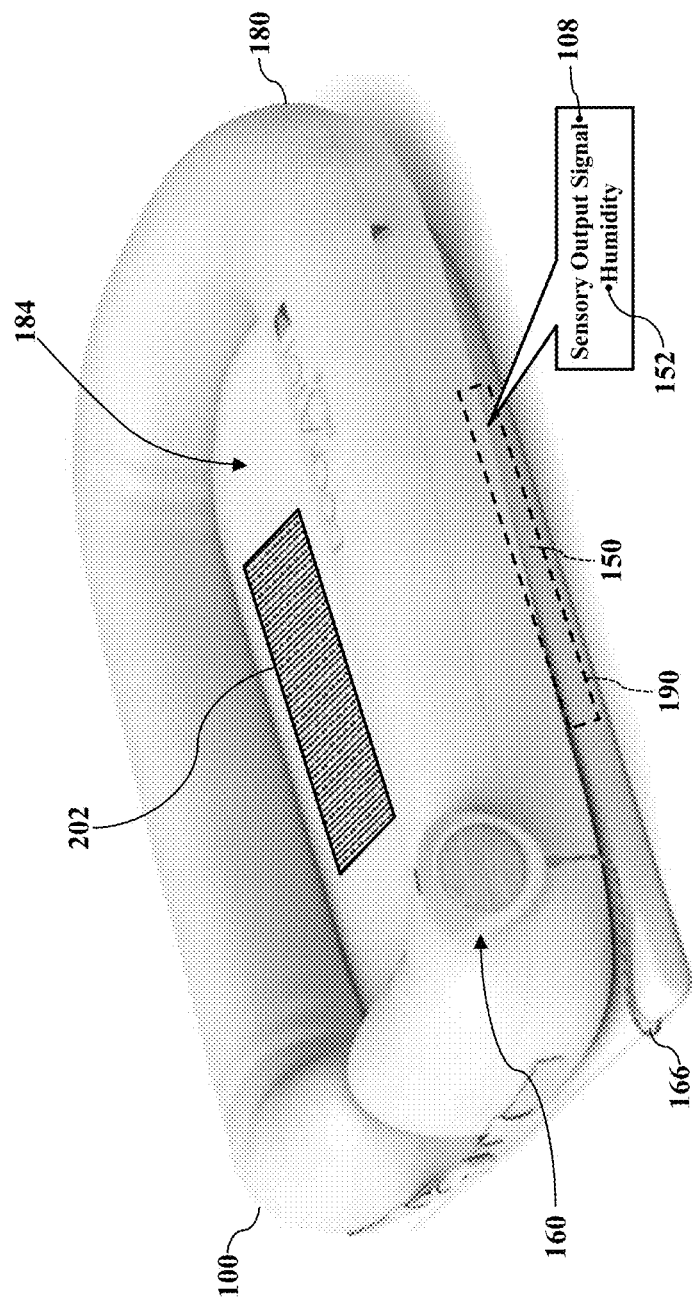

FIG. 11 illustrates an optional sensory installation. Here the conductive strands 202 may be integrated into at least a portion of a floor of the upper textile product 180. When the user (such as the infant 102 illustrated in FIGS. 1-2) sits, plays, or rests within the interior portion 184, the user may sit directly above the conductive strands 202. The conductive strands 202 may thus convey current, voltage, capacitance, and/or resistance that may represent the humidity 152. There are many schemes and techniques for using the conductive strands 202 to determine the humidity 152, and exemplary embodiments are agnostic and may use any of the schemes and techniques. The humidity sensor 150 generates the sensory output signal 108 representing the infant 102 is dry, sweaty, nervous, emotionally upset, and/or has a wet/soiled diaper (as this disclosure above explained).

Figure 12:
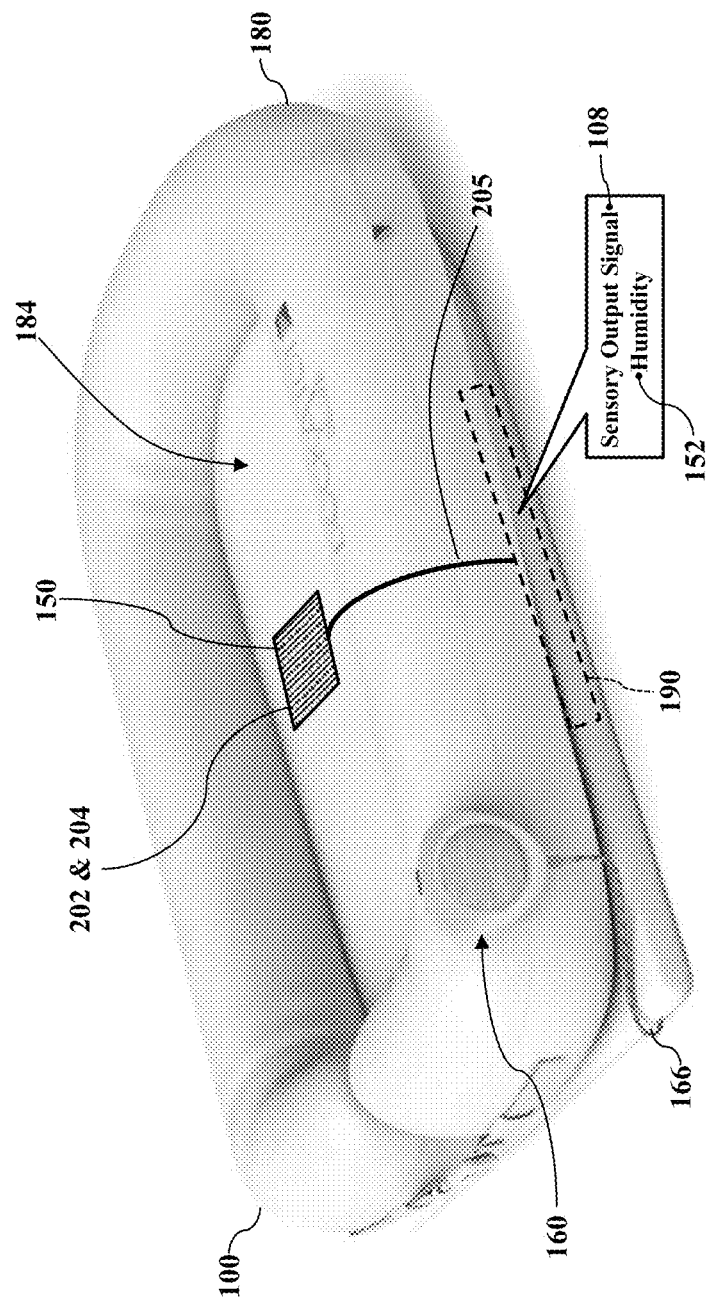

FIG. 12 illustrates yet another placement and configuration of the conductive strands 202. While the conductive strands 202 may be woven, embroidered, or otherwise integrated anywhere in the upper textile product 180, FIG. 12 illustrates a movable patch 204. The patch 204 contains the conductive strands 202 and may be placed, arranged, or located for cost-efficient results. For example, the patch 204 may be a separate and/or purchasable component that adds the humidity sensor 150 to the monitoring system 100. Because the patch 204 integrates the conductive strands 202, the patch 204 may be placed below the infant 102 to best sense the humidity 152. While exemplary embodiments may establish wireless communication between the patch 204 and the internal unit 190, FIG. 12 illustrates an electrical cable 205. The electrical cable 205 electrically connects to the internal unit 190 for data/signal transmission. The electrical cable 205 may thus convey the sensory output signals 108 to the internal unit 190 for processing and analysis. The electrical cable 205 may alternatively or additionally connect to the auxiliary unit 160 for processing and analysis.

Figure 13:
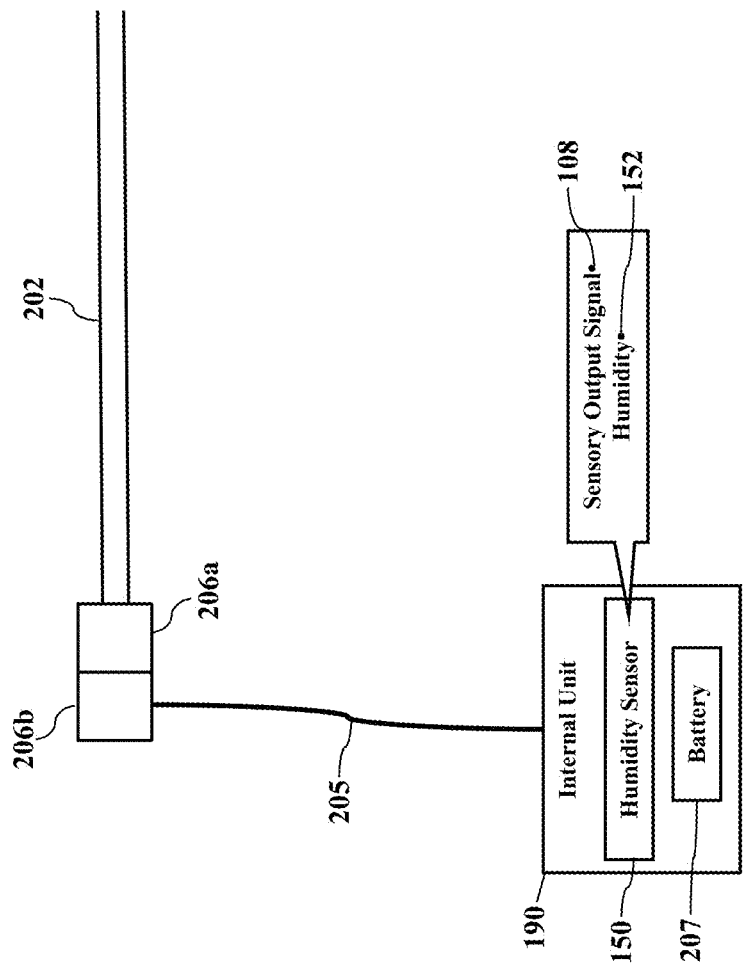

FIG. 13 illustrates a general schematic or architecture for the conductive strands 202. Male and female electrical connectors 206a and 206b establish an electrical connection (via the electrical cable 205) between the conductive strands 202 and the humidity sensor 150 (perhaps in the internal unit 190). The internal unit 190 receives electrical power (current and voltage) from a power source 207. FIG. 13 illustrates the power source 207 as an internal DC battery, but the power source 207 may be based on a connection to the AC electrical grid (and perhaps AC/DC conversion, if needed). Regardless, either AC or DC electrical power is applied to the conductive strands 202, and the humidity sensor 150 generates the sensory output signal 108. Exemplary embodiments may then process the sensory output signal 108 to determine the humidity 152.

FIG. 14 further illustrates the cushioned pad 122 or mattress 123, according to exemplary embodiments. Here the cushioned pad 122 or mattress 123 may have an internal cavity 192 into which the internal unit 190 inserts. (Recall that the cushioned pad 122 or mattress 123 may sit below the upper textile product 180, as FIG. 7 best illustrates). The internal unit 190 may have the outer enclosure 194 that houses internal mechanical and/or electronic componentry (such as one or more of the sensors 104 and perhaps the contact mechanism 140). The cushioned pad 122 or mattress 123 may further have the internal channel 196 through which the physical cable 166 (illustrated in FIG. 7) to the auxiliary unit 160 is routed or inserted. The cushioned pad 122 or mattress 123 may thus internally contain at least some of the sensors 104 that help infer the user's humidity 152 and/or overall status 106.

Exemplary embodiments may include different purchase packages. The monitoring system 100 may be marketed and offered for sale using different combinations of components. For example, a purchaser may purchase the textile product 180 with the mattress 123 (with or without internal cavity 192 and/or internal channel 196), as a less costly package without monitoring capabilities. Should the purchaser later desire monitoring capabilities, the auxiliary unit 160, the internal unit 190, and optionally the stabilizer 207 (and, if needed, the cushioned pad 122 and/or mattress 123) may be purchased together as a monitoring kit, including for example, the humidity sensor 150 (e.g., the conductive textile 203), the motion sensor 112, and the contact mechanism 140. The purchaser, in other words, may separately purchase the auxiliary unit 160 and the internal unit 190 (and, if needed, the cushioned pad 122 and/or mattress 123) as a retrofit option that adds monitoring capabilities. Exemplary embodiments, though, may be offered as a complete package. That is, the textile product 180, the cushioned pad 122 and/or mattress 123, the auxiliary unit 160, and the internal unit 190 may be purchased together for immediate monitoring capabilities.

FIG. 15 is a simple illustration of the contact mechanism 140, according to exemplary embodiments. Exemplary embodiments activate the contact mechanism 140 to provoke a response in the user (such as the infant 102 illustrated in FIGS. 1-2) sitting or lying within the interior portion 184. Should any sensor 104 indicate that the user has ceased breathing for a period of time outside of a threshold value, the contact mechanism 140 responds with a physical input. The physical input promotes the infant 102 to resume breathing. FIG. 15, for example, illustrates one or more movable pegs 210a and 210b. The pegs 210a and 210b, when activated, upwardly extend from the internal unit 190. Each peg 210 slides up into contact with the cushioned pad 122 or mattress 123. Each peg 210 may even slide through the cushioned pad 122 or mattress 123 (as later paragraphs will explain). Each peg 210 may impart a force that impacts the cushioned pad 122 and/or the mattress 123 beneath the infant 102. The peg 210 may alternatively slide partially or entirely through the mattress 123. Indeed, the peg 210 may slide entirely through the cushioned pad 122 and/or mattress 123 and directly poke a bottom surface of the interior portion 184 and thus infant 102. Regardless, the peg 210 imparts a force that may be tactilely felt by the infant 102 (even through fabric covers, bed sheets, clothing, and blankets). In plain words, the contact mechanism 140 jolts or nudges the infant 102 to promote breathing, thus restoring the sensory output signal 108 (generated by the motion sensor 112) above the apneatic condition 130.

FIG. 16 is a detailed block diagram illustrating the operating environment, according to exemplary embodiments. Here the auxiliary unit 160 establishes communication via the communications network 176 with any device, such as the parent's mobile smartphone 118. The auxiliary unit 160 may thus have a hardware processor 220 (e.g., "µP"), application specific integrated circuit (ASIC), or other component that executes an auxiliary-side algorithm 222 stored in a local memory device 224. The auxiliary-side algorithm 222 may instruct the hardware processor 220 to perform operations, such as receiving or determining the sensory output signal 108 representing the temperature 164 sensed by the temperature sensor 162. The auxiliary-side algorithm 222 may thus also instruct the hardware processor 220 to invoke a transceiver ("TX/RX") 226 for wireless transmission of signals via the communications network 176 (perhaps to the smartphone 118).

The auxiliary unit 160 may also communicate with the internal unit 190. FIG. 16 illustrates a USB interface 228 for high speed USB serial communication via the physical cable 166, but wireless communication may also be established via the communications network 176. Regardless, the internal unit 190 may also have a hardware processor 230 (e.g., "µP"), application specific integrated circuit (ASIC), or other component that executes an internal-side algorithm 232 stored in a local memory device 234. The internal-side algorithm 232 may instruct the hardware processor 230 to perform operations, such as sending the sensory output signal(s) 108 generated by the motion sensor 112 and/or the humidity sensor 150 to the auxiliary unit 160. The auxiliary unit 160 may thus use any of the sensory output signal(s) 108 to infer the status 106 of the user and to even activate the contact mechanism 140. In an alternate embodiment, internal unit 190 may establish communication via the communications network 176 directly with any device, such as the parent's mobile smartphone 118. Moreover, the internal-side algorithm 232 may instruct the hardware processor 230 to perform operations, such as receiving or determining the sensory output signal 108 (such as the movement 114 sensed by the motion sensor 112 and/or the humidity 152 sensed by the humidity sensor 150). The internal unit 190 may also incorporate the temperature sensor 162, thus generating or receiving sensory output signal 108 representing the temperature 164. The internal unit 190 may also include a transceiver for wireless transmission of signals via the communications network 176 (perhaps to the smartphone 118).

The smartphone 118 may also analyze the sensory output signal(s) 108. The auxiliary-side algorithm 222 may instruct the hardware processor 220 to send any of the sensory output signal(s) 108 to any destination, such as the smartphone 118. The internal-side algorithm 232 may instruct the hardware processor 230 to send any of the sensory output signal(s) 108 to any destination, such as the smartphone 118. When the smartphone 118 receives the sensory output signal(s) 108, the smartphone 118 may use its computing/processing resources to infer the user's status 106. As the reader likely understands, the smartphone 118 also has a hardware processor 240 that executes a mobile application 242 stored in a local memory device 244. The mobile application 242 may instruct the hardware processor 240 to infer the user's status 106 based on the sensory output signal(s) 108.

Exemplary embodiments may packetize information/data. Any information or data may be sent or received as packets of data according to a packet protocol (such as any of the Internet Protocols). The packets of data contain bits or bytes of data describing the contents, or payload, of a message. A header of each packet of data may contain routing information identifying an origination address and/or a destination address. Each hardware processor 220, 230, and 240 may be instructed to inspect any data packet for a network address (such as an Internet protocol address).

Exemplary embodiments may be applied regardless of networking environment. Exemplary embodiments may be easily adapted to stationary or mobile devices having cellular, WI-FI®, near field, BLUETOOTH®, or any other wireless capability. Exemplary embodiments may be applied to mobile devices utilizing any portion of the electromagnetic spectrum and any signaling standard (such as the IEEE 802 family of standards, GSM/CDMA/TDMA or any cellular standard, and/or the ISM band). Exemplary embodiments, however, may be applied to any processor-controlled device operating in the radio-frequency domain and/or the Internet Protocol (IP) domain. Exemplary embodiments may be applied to any processor-controlled device utilizing a distributed computing network, such as the Internet (sometimes alternatively known as the "World Wide Web"), an intranet, a local-area network (LAN), and/or a wide-area network (WAN). Exemplary embodiments may be applied to any processor-controlled device utilizing power line technologies, in which signals are communicated via electrical wiring. Indeed, exemplary embodiments may be applied regardless of physical componentry, physical configuration, or communications standard(s).

Exemplary embodiments may utilize any processing component, configuration, or system. Any hardware processor could be multiple processors, which could include distributed processors or parallel processors in a single machine or multiple machines. The processor can be used in supporting a virtual processing environment. The processor could include a state machine, application specific integrated circuit (ASIC), programmable gate array (PGA) including a Field PGA, or state machine. When any of the processors execute instructions to perform "operations", this could include the processor performing the operations directly and/or facilitating, directing, or cooperating with another device or component to perform the operations.

Figure 17:
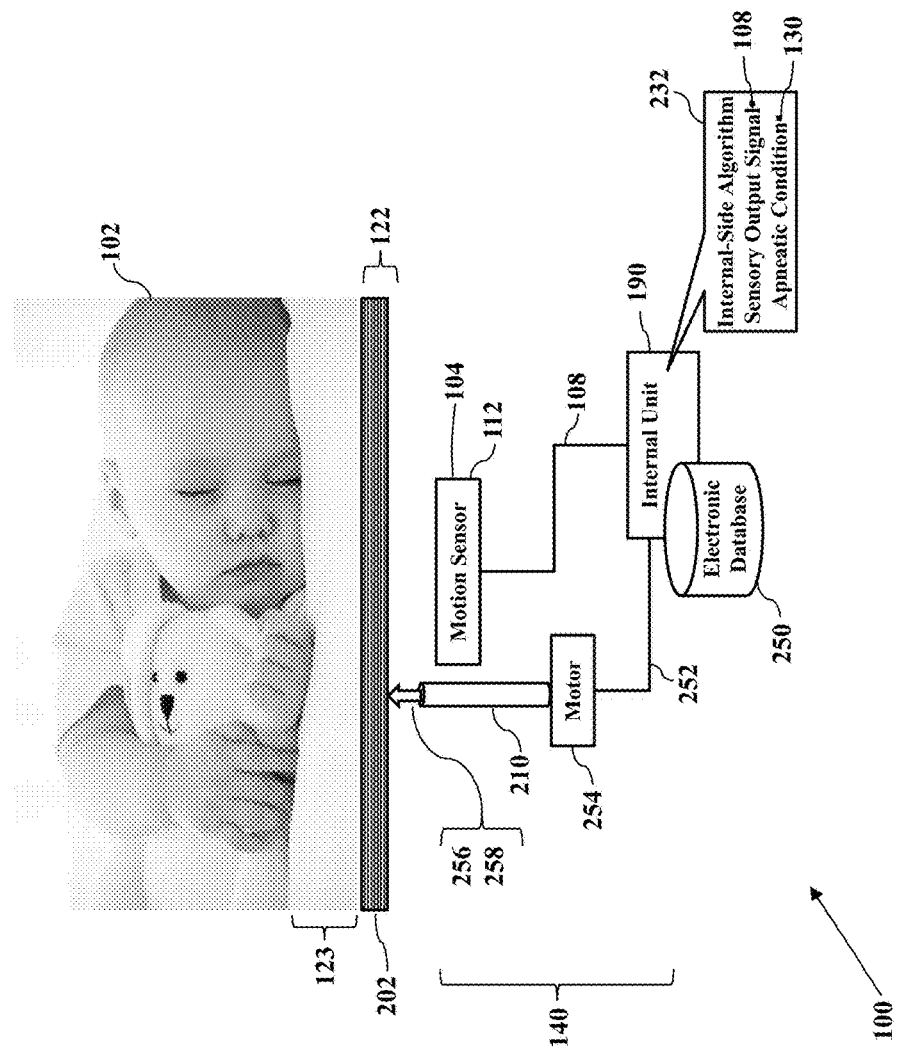
Figure 18:
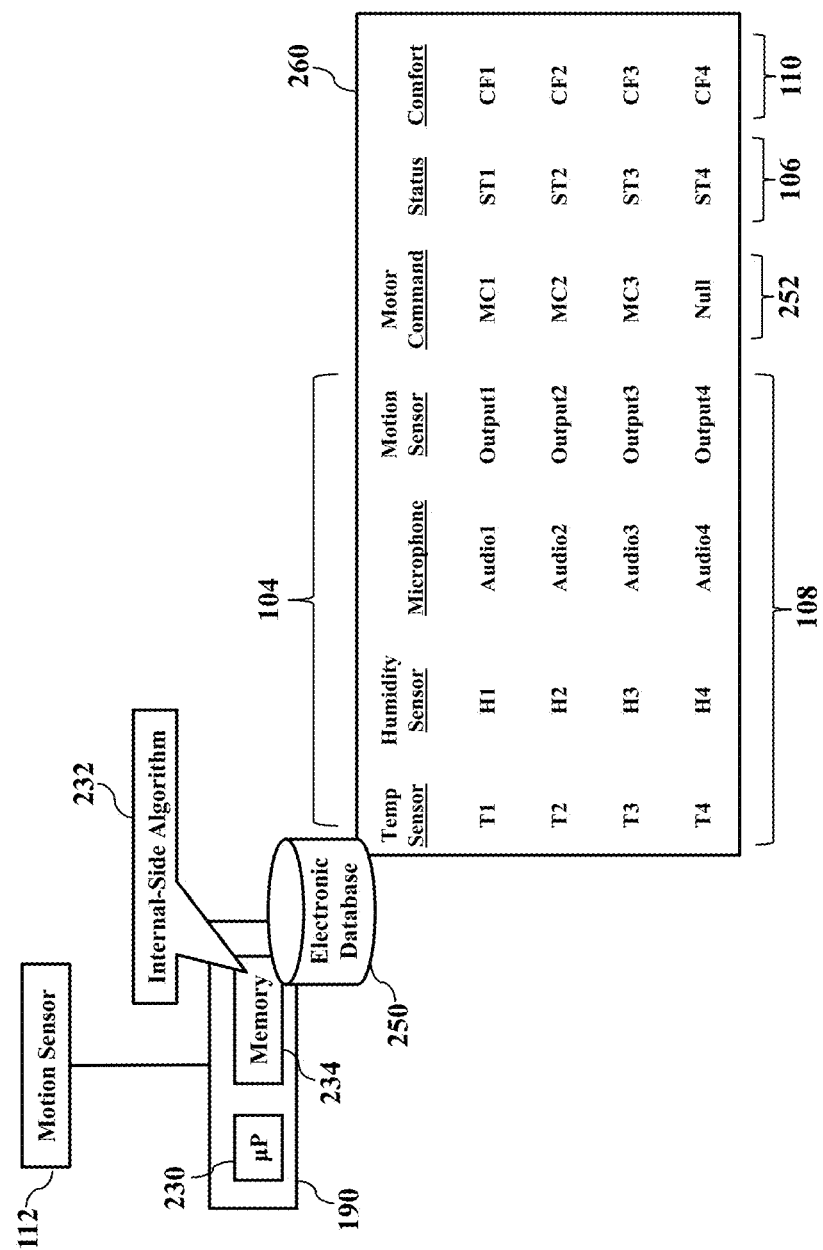

FIGS. 17-18 are more detailed illustrations of the contact mechanism 140, according to exemplary embodiments. The contact mechanism 140 may be activated in response to the sensory output signal 108 generated by any of the sensors 104 (such as the motion sensor 112). When the sensory output signal 108 generated by the motion sensor 112 (whether analog or digital) is received, the internal-side algorithm 232 may cause the sensory output signal 108 to be compared to entries in an electronic database 250. The electronic database 250 may be populated with values of the sensory output signal 108 that require activation of the contact mechanism 140. If the value or values associated with the sensory output signal 108 match or satisfy an entry in the electronic database 250, then exemplary embodiments may execute a corresponding action. For example, if the sensory output signal 108 indicates the apneatic condition 130, then perhaps the infant's breathing has stopped. The electronic database 250 may thus contain an instruction, command, or rule that causes the contact mechanism 140 to be activated, thereby propelling the peg 210 into contact with the cushioned pad 122 and/or mattress 123 beneath the infant 102. Exemplary embodiments may even prod or poke the infant 102, as later paragraphs will explain.

As FIG. 17 illustrates the contact mechanism 140 jolts the infant 102 to resume breathing. The electronic database 250 may identify, send or convey a corresponding motor command 252 to the contact mechanism 140. When the contact mechanism 140 activates, a motor 254 causes the peg 210 to move and impact the cushioned pad 122 and/or mattress 123 beneath the infant 102. That is, when the motor 254 receives electrical power (DC battery or AC grid), the motor 254 actuates, e.g., spins or rotates. The contact mechanism 140 converts rotational motion in the motor 254 into sliding, translational movement in the peg 210. The peg 210 thus upwardly moves and strikes the cushioned pad 122 and/or mattress 123 with a force 256 and a velocity 258. The peg 210, in plain words, jolts or nudges the infant 102 to promote resumption of breathing. Exemplary embodiments may thus singularly or repeatedly poke or nudge until the sensory output signal 108 indicates normal breathing has resumed.

FIG. 18 further illustrates the electronic database 250. The electronic database 250 may contain predefined levels of the status 106 (such as the comfort 110) for different combinations and values of the sensory output signals 108 generated by the various sensors 104. While the electronic database 250 may have any configuration, for simplicity FIG. 18 illustrates the electronic database 250 as a table 260 that electronically maps, relates, or identifies different values and combinations of the sensory output signals 108 to the user's corresponding status 106 and/or comfort 110. Indeed, the electronic database 250 may have entries that associate the sensory output signals 108 to their corresponding motor commands 252. FIG. 18 illustrates the electronic database 250 as being locally stored in the memory device 234 of the internal unit 190, but some or all of the electronic database entries may be remotely maintained at some other device or network location (as later paragraphs will explain). Alternatively, hardware processor 230 and/or memory device 234 may be maintained or housed at some other device or network location, separate from the internal unit 190. Although FIG. 18 only illustrates a few entries, in practice the electronic database 250 may contain many electronic database entries that richly define the status 106, the comfort 110 and/or the motor commands 252 for small increments in, and/or, detailed combinations of, the sensory output signals 108.

Exemplary embodiments may thus query the electronic database 250. Once any of the sensory output signals 108 is/are determined, the internal-side algorithm 232 may instruct the processor 230 to consult the electronic database 250 to determine the status 106, the comfort 110, and/or the motor commands 252. Exemplary embodiments may thus determine any numerical values associated with the sensory output signals 108 and then perform a database lookup to retrieve the corresponding entries. For example, each motor command 252 may define or specify values of the force 256 and/or the velocity 258 (illustrated in FIG. 17) that nudge or punch the cushioned pad 122 and/or mattress 123 to promote a resumption of breathing.

Returning back to FIG. 17, the motor command(s) 252 instruct(s) the motor 254. Once the motor command 252 is determined, the motor command 252 is sent to the motor 254, e.g., by the internal unit 190. The motor command 252 instructs the motor 254 to actuate, e.g., move or spin, thus causing the peg 210 to slide and to nudge or poke the cushioned pad 122 and/or mattress 123. The motor command 252, in particular, may specify a rotational speed, a torque, a duration, and/or a rotational angle at which the motor 254 should spin to create the force 256 at the velocity 256 that jolts or nudges the non-breathing infant 102. Exemplary embodiments may thus singularly or repeatedly reciprocate the peg 210 until the sensory output signal 108 indicates breathing has resumed.

Figure 20:
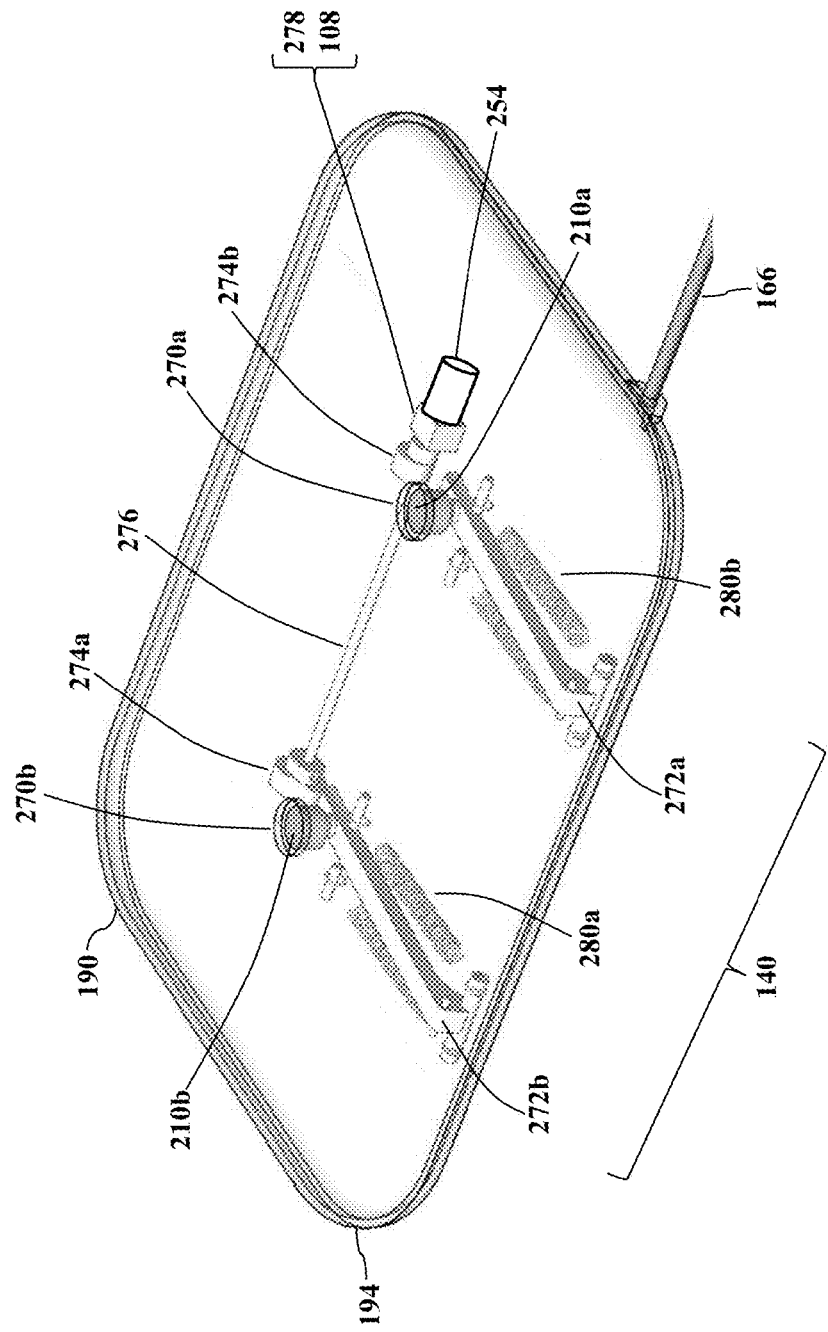

FIGS. 19-20 are still more detailed illustrations of the contact mechanism 140 and the internal unit 190, according to exemplary embodiments. FIG. 19A illustrates a top view, FIG. 19B illustrates an isometric view, and FIG. 20 illustrates a cut-away internal view. The outer enclosure 194 is preferably molded of a rigid material (such as plastic or other polymer) that substantially encloses and protects the contact mechanism 140. The contact mechanism 140 locally compresses at least a portion of the cushioned pad 122 and/or mattress 123 beneath the infant 102 (such as illustrated in FIGS. 1, 7, 15, and 17) in response to the user's status 106. For example, should exemplary embodiments assume or infer the apneatic condition 130, the contact mechanism 140 may be activated to jolt or nudge the infant to promote resumption of breathing. Recall that the motion sensor 112 may be used to detect the infant's inhaling, exhaling, and other respiratory events (as previously explained). If the infant 102 pauses or stops breathing, the contact mechanism 140 may be activated. The contact mechanism 140 may repeatedly poke or nudge the cushioned pad 122 and/or mattress 123, thus rocking or poking the infant. The contact mechanism 140, in other words, disturbs the infant to promote resumption of breathing by the infant.

FIG. 19 illustrates the contact mechanism 140. The contact mechanism 140 may convert rotational movement into translational, pistonal movement. The outer enclosure 194 may have a pair of open cylinders 270a and 270b exposing the pair of pegs 210a and 210b. Each cylinder 270a and 270b has a diameter bore and length sized to allow vertical, translational, sliding motion of the corresponding pegs 210a and 210b. Each peg 210a and 210b is respectively connected to a pivoting rocker arm 272a and 272b. The pivotal motion of the rocker arms 272a and 272b translates into downward and upward sliding motion of the pegs 210a and 210b. Each rocker arm 272a and 272b contacts and is driven by a respective cam 274a and 274b mounted to a camshaft 276. In one embodiment, a camshaft position sensor 278 may be mounted to the camshaft 276 to detect positional and/or rotational changes. The motor 254 is connected to the camshaft 276. The camshaft position sensor 278 may generate its sensory output signal 108 in response to rotational movements of the camshaft 276, whether back-and-forth or clockwise-counterclockwise. Each rocker arm 272a and 272b may have one or more springs 280a and 280b to ensure the corresponding peg 210a and 210b returns to a desired position (such as bottom dead center or rest position). Exemplary embodiments may thus convert rotational inputs from the motor 254 into linear travels of the pegs 210a and 210b.

Exemplary embodiments may thus drive the pegs 210a and 210b. Electrical power (whether AC or DC battery, not shown for simplicity) causes the motor 254 to rotate the camshaft 276. As the reader may envision, the pegs 210a and 210b slide up and down in response to rotational motion of the camshaft 276 (according to a profile of the respective cams 274a and 274b). As the camshaft 276 rotates (whether clockwise or counterclockwise), the cams 274a and 274b also rotate and pivot the rocker arms 272a and 272b at contact. Each rocker arm 272a and 272b thus forces its corresponding peg 210a and 210b to slide up or down within the corresponding cylinder 270a and 270b. Each reciprocating peg 210a and 210b locally compresses the cushioned pad 122 and/or mattress 123, thus imparting or causing vertical forces and vertical motion in the cushioned pad 122 and/or mattress 123. As the pegs 210a and 210b reciprocate, forces are imparted to, and propagate within, the cushioned pad 122 and/or mattress 123. The reciprocating pegs 210a and 210b may thus be felt by the user lying above the cushioned pad 122 and/or mattress 123.

Exemplary embodiments may thus respond to the apneatic condition 130. When the apneatic condition 130 is determined (such as illustrated with reference to FIG. 17), exemplary embodiments may activate the contact mechanism 140. The motor 254 causes the pegs 210a and 210b to reciprocate, thus jabbing and poking the cushioned pad 122 and/or mattress 123. The pegs 210a and 210b may impact the cushioned pad 122 and/or mattress 123 at a variable amplitude and frequency, depending on configurable parameters (such as a rotational speed and direction of the motor 254 and the profiles of the cams 274a and 274b). As the pegs 210a and 210b poke the cushioned pad 122 and/or mattress 123, material is compressed, thus transferring vertical motion and force to the infant lying above the cushioned pad 122 and/or mattress 123. The infant is thus gently rocked or even agitated, which may promote resumption of breathing. Exemplary embodiments may thus nudge, poke, or even jolt the infant 102 into an alert or awareness that may overcome the apneatic condition 130.

FIG. 21 illustrates remote activation, according to exemplary embodiments. Here the motor 254 may be commanded to power on and force the pegs 210a and 210b to move and nudge the user (such as the infant 102). Suppose, for example, that the parent merely wants to hear the infant's voice (perhaps as captured by the microphone 170). The parent may thus use his or her smartphone 118 to command the internal unit 190 to slide the pegs 210a and 210b. The mobile application 242, for example, may have a configuration or setting that causes the smartphone 118 to display a graphical control associated with the motor command 252. When the parent selects the graphical control (such as touching a button icon displayed by the smartphone 118), the mobile application 242 generates the motor command 252. The mobile application 242 causes the smartphone 118 to send the motor command 252 to the contact mechanism 140 (perhaps via the auxiliary unit 160 and/or to the internal unit 190). The motor command 252 is preferably wirelessly transmitted via the communications network 176 (illustrated in FIG. 16) to a network address (e.g., IP address) associated with the auxiliary unit 160 and/or the internal unit 190. The motor command 252, however, may be conveyed via the physical cable 166 or wirelessly) to the motor 254 operating in the internal unit 190. As the motor 254 spins, the peg 210 touches or impacts the cushioned pad 122 and/or mattress 123 (as illustrated in FIG. 17). The infant 102 will thus feel the up-and-down, reciprocating motion of the pegs 210, perhaps causing the infant 102 to giggle or whimper. The microphone 170 may even capture the infant's voice for transmission back to the smartphone 118, thus soothing the parent with the infant's responsive voice.

Exemplary embodiments may thus include remote signalization. Caregivers and parents may remotely issue the motor command 252 to cause responsive speech, movement, and/or promote breathing in the user/child. For example, should the infant's lack of movements become a concern, the parent may easily and gently nudge or rock the infant 102 (via the sliding peg 210) to invoke responsive movement or sounds. Indeed, the auxiliary-side algorithm 222, the internal-side algorithm 232, and/or the mobile application 242 may individually or cooperatively instruct the motor 254 to spin. The motor 254 may even be commanded to spin or rotate at different speeds for different responses. A slow rotational speed, for example, would slowly reciprocate the peg 210, while a fast, rotational speed would produce a quick agitation or kneading action. Exemplary embodiments may thus gently rouse or jar the user, depending on the situation. As exemplary embodiments evaluate the sensory output signals 108, exemplary embodiments may automatically generate the motor command 252 to affect movement and/or speech. The sensory output signals 108 may thus be compared to threshold values defining situations in which the motor 254 should spin at different speeds.

Exemplary embodiments may also autonomously drive the peg 210. This disclosure previously explained how the motion sensor 112 senses the infant's breathing. If the motion sensor 112 generates a null or low output signal, exemplary embodiments may infer that the infant has stopped breathing. Exemplary embodiments may then autonomously generate the motor command 252 to nearly immediately drive the peg 210. The auxiliary-side algorithm 222, for example, may be configured to immediately generate the motor command 252 in response to the null/low output signal unit from the motion sensor 112. The internal-side algorithm 232 and the mobile application 242 may also be configured to generate and send the motor command 252. These cumulative motor commands 252 ensure that the peg 210 reciprocates and jolts or nudges the infant to promote resumption of breathing.

FIG. 22 illustrates an optional presence detection 290, according to exemplary embodiments. Here exemplary embodiments may detect when the infant 102 sits or lies atop the cushioned pad 122 and/or the mattress 123. Any output generated by the sensors 104 may thus be used to determine whether a user (such as the infant 102) lies atop or sits within the monitoring system 100. For example, when the infant 102 rests, the motion sensor 112 detects the infant's breathing and other body movements 114 (as this disclosure above explains). However, if the motion sensor 112 has a zero (0) or baseline sensory output signal 108, then exemplary embodiments may be programmed or configured to assume that no user lies atop or within the monitoring system 100. That is, if the sensory output signal 108 is below perhaps a minimum value 292, then the internal-side algorithm 232 may infer that the monitoring system 100 is unused. Similarly, if the humidity sensor 150 (perhaps integrating the conductive strands 202) determines a zero (0) or baseline sensory output signal 108, then exemplary embodiments may again be programmed or configured to assume that no user lies atop or within the monitoring system 100. Exemplary embodiments may thus conserve battery/electrical power consumption when the infant's presence is undetected.

The presence detection 290 may also influence other componentry. For example, the internal unit 190 may idle when not in use. If the presence detection 290 infers that the monitoring system 100 is unused, then the internal unit 190 may enter an idle or shutdown state. That is, when the sensory output signal 108 is equal to or below the minimum value 292, the internal-side algorithm 232 may instruct the internal unit 190 to cease the processing of any tasks or instructions associated with monitoring. Similarly, the internal-side algorithm 232 may also instruct or inform the auxiliary unit 160 of the presence detection 290, thus also allowing the auxiliary unit 160 to cease the processing of any tasks or instructions associated with monitoring. However, when the sensory output signal 108 exceeds the minimum value 292, then processing may revive.

FIGS. 23-24 illustrate a rest quality 300, according to exemplary embodiments. Here exemplary embodiments may further define the infant's comfort 110 based on the sensory output signal(s) 108 generated by any of the sensor(s) 104. For example, exemplary embodiments may infer the infant's rest quality 300 based on her movements 114. As the reader likely understands, poor rest patterns may affect mood, mental performance, and physical energy. In plain words, the infant's rest quality 300 may assist in predicting his or her emotional behavior, attentiveness, physical capabilities, and routine. Exemplary embodiments may thus consult the electronic database 250 to predict the infant's rest quality 300.

FIG. 24 further illustrates the electronic database 250. Here the electronic database 250 may have entries that associate different sensory output signals 108 to their corresponding levels or measures of the rest quality 300. Any time the sensory output signal 108 is received or determined, exemplary embodiments may query the electronic database 250 for the corresponding rest quality 300 and/or the comfort 110. As the reader may understand, calm movements and quiet voices likely indicate a good or high level of the rest quality 300. However, transient or erratic movements and crying may likely indicate poor rest quality 300. The electronic database 250 may thus be populated with fine and/or gross associations between the sensory output signals 108 and their corresponding levels or measures of the rest quality 300. The internal-side algorithm 232 may instruct the internal unit 190 to identify or retrieve the rest quality 300 that matches or satisfies the instantaneous or average sensory output signal 108 generated by the sensors 104. Exemplary embodiments may then report the rest quality 300 to any destination (as later paragraphs will explain).

FIG. 25 illustrates rest monitoring, according to exemplary embodiments. Here exemplary embodiments may track and log the infant's daily activities. The sensory output signals 108 (generated by any of the sensors 104) may be characterized and categorized for analysis, reporting, and long-term monitoring. Some of the sensory output signals 108, for example, may be recognized as a rest moment, while other sensory output signals 108 may be recognized as play. Still other sensory output signals 108 may be recognized as crying moments, anger moments, and crawling moments. Any sensory output signal 108 (generated by any of the sensors 104) may be compared to known signal patterns 310 and assigned to a corresponding activity 312. An electronic log 314 may thus cumulatively store the infant's categorized activities 312 according to time. The electronic log 314, in other words, tracks the time spent resting, playing, and other activities 312. Exemplary embodiments may thus log and report the time the infant 102 falls asleep, the time the infant 102 awakes, daily times of urination, and/or other random and habitual activities. FIG. 25 illustrates the electronic log 314 locally stored within the internal unit 190. Some or all entries in the electronic log 314 may be stored in the auxiliary unit 160 and/or some other network location (such as the smartphone 118). The electronic log 314 may even be remotely maintained in a cloud-based server (as later paragraphs explain).

FIG. 26 illustrates positioning of the peg 210, according to exemplary embodiments. Here exemplary embodiments account for the different sizes and ages of infants that may lie within the monitoring system 100. As the monitoring system 100 may accommodate newborns to toddlers, the peg 210 may be placed or located at a position that is effective for most users. As the infant 102 grows, the peg 210 may be positioned to poke or nudge the general location of chest cavities from newborns to toddlers. FIG. 26 thus illustrates the peg 210 positioned along a longitudinal centerline 320 of the cushioned pad 122 or mattress 123 and above a midline 322 of the cushioned pad 122 or mattress 123. The peg 210 may thus be positioned below a chest cavity region 324 that is sized to statistically fit or correspond to the general population of newborns to toddlers.

Figure 27:
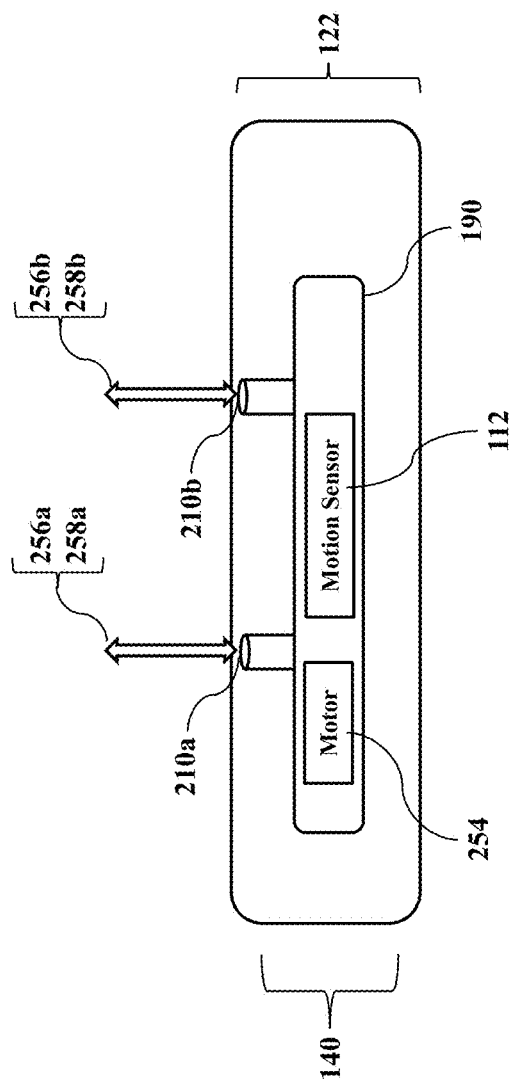
Figure 28:
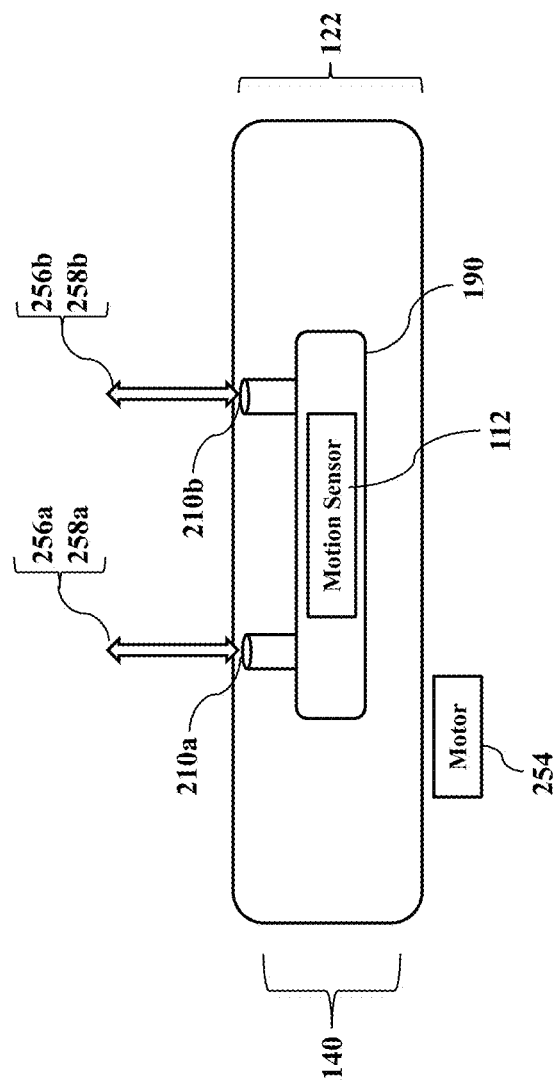
Figure 29:
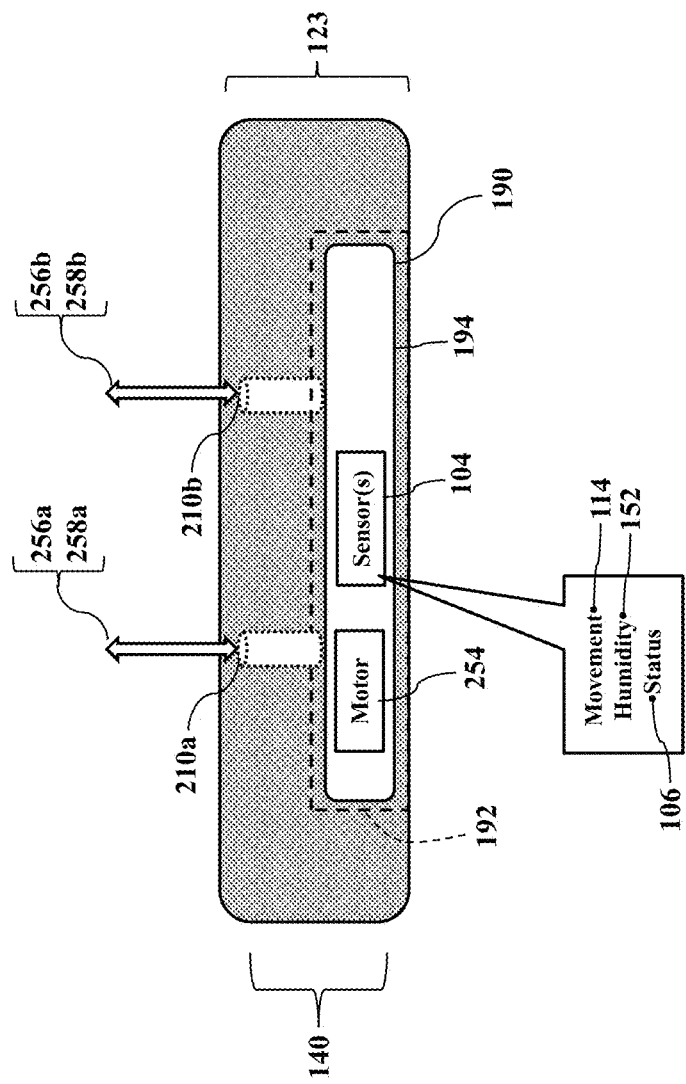

FIGS. 27-29 illustrate packaging considerations, according to exemplary embodiments. Here the componentry and complexity of the contact mechanism 140 may have differing configurations depending on design, size, weight, cost, and/or convenience. FIG. 27, for example, illustrates the internal unit 190 installed within the cushioned pad 122 or mattress 123. The internal unit 190 contains or houses the contact mechanism 140. The motor 254 and/or the motion sensor 112 may also be packaged within the internal unit 190 and, thus, within the cushioned pad 122 or mattress 123. When the contact mechanism 140 is activated, the pegs 210*a* and 210*b* locally punch an upper surface of the cushioned pad 122 or mattress 123, thus rousing the user lying above (as earlier paragraphs explained).

FIG. 28, though, illustrates an alternate package. Here at least some mechanisms and/or componentry may be packaged or located external, or partially external to the cushioned pad 122 or mattress 123. For example, a size of the internal unit 190 may be reduced by packaging the motor 254 outside the cushioned pad 122 or mattress 123, perhaps as a separate unit or module. The motor 254 may thus have a driveshaft, gears, linkage, or any other mechanism (not shown) that connects to the internal unit 190 to slide the pegs 210*a* and 210*b*. The internal unit 190, in other words, may be reduced in size and weight by externally packaging the motor 254. This configuration may also help to provide the infant 102 with a significantly obstacle free surface.

FIG. 29 illustrates still another alternate configuration. Here the internal unit 190 may be incorporated within the cushioned pad 122 or mattress 123. As this disclosure above explained, the cushioned pad 122 or mattress 123 may have the internal cavity 192 into which the internal unit 190 inserts (as FIG. 14 previously illustrated). Because the cushioned pad 122 or mattress 123 may sit below the upper textile product 180 (as FIGS. 1-2, 5, and 7 best illustrate), here the cushioned pad 122 or mattress 123 may incorporate the internal unit 190 and, thus, the contact mechanism 140. The internal unit 190 may have the outer enclosure 194 that houses any of the sensors 104 and perhaps the contact mechanism 140. The cushioned pad 122 or mattress 123 may thus internally contain the internal unit 190 and at least some of the sensors 104 that help infer the user's movement 114, humidity 152, and/or overall status 106.

Figure 30:
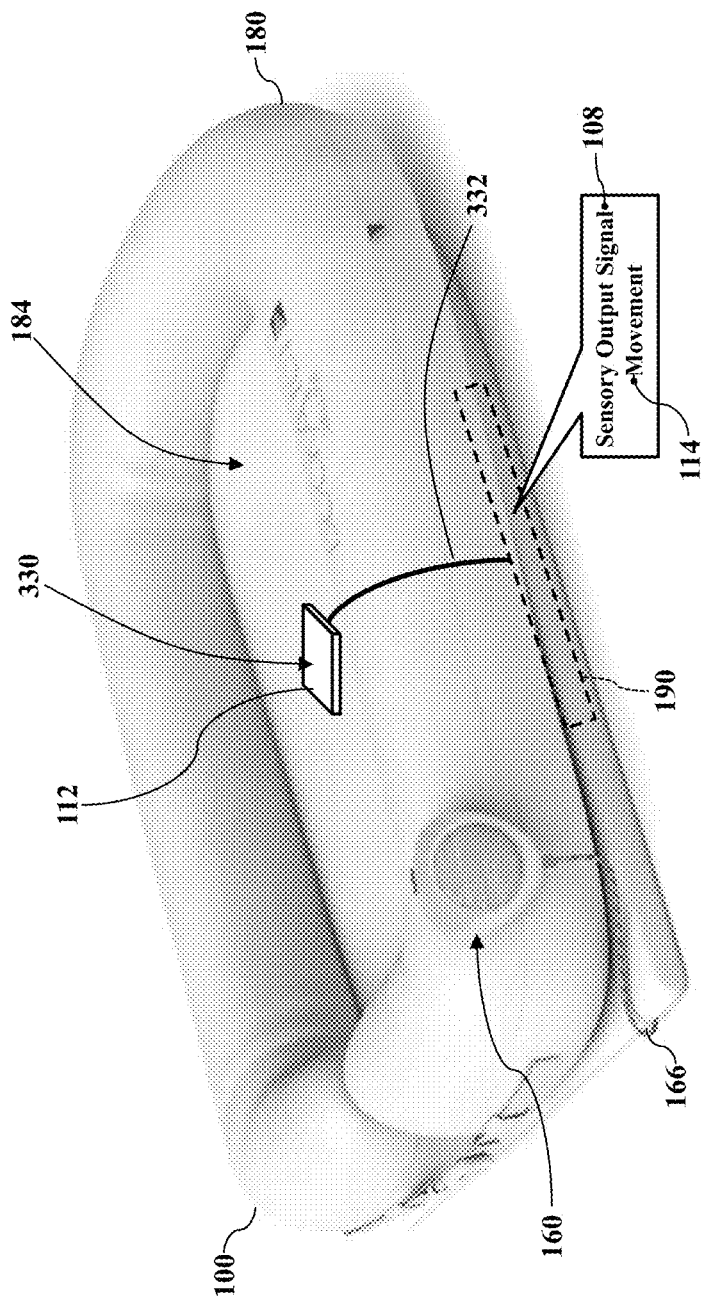

FIG. 30 illustrates an additional packaging option, according to exemplary embodiments. Here the motion sensor 112 may be externalized and placed where desired. The above paragraphs describe the motion sensor 112 being housed within the internal unit 190. The motion sensor 112, however, may be a separate, external component that is placed anywhere on, or within, the monitoring system 100. FIG. 30, for example, illustrates the motion sensor 112 as a moveable or mobile fob 330. The fob 330 may thus be a small form factor package, stick, or case that houses the motion sensor 112. The fob 330 may then wirelessly transmit its sensory output signal(s) 108 (via a network interface to the communications network 176 in FIG. 16) to the internal unit 190 or to the auxiliary unit 160 for analysis and remote reporting. The fob 330, however, may have a physical, wired connection (perhaps via cable 332) to the internal unit 190 or to the auxiliary unit 160. The fob 330 may thus be placed (such as within the interior portion 184) in close proximity to the user.

FIGS. 31-32 are more detailed illustrations of the auxiliary unit 160, according to exemplary embodiments. FIG. 31 illustrates the auxiliary unit 160 having a base 370, while FIG. 32 is an exploded view of the individual components. While the auxiliary unit 160 may have any exterior shape, this disclosure illustrates a sleek, modern, and generally ovoid outer shape. As FIG. 32 illustrates, a top 372 and a bottom 374 may mate or engage to form an outer enclosure housing internal components. A printed circuit board 376 contains electronic componentry (such as the temperature sensor 162, the microphone 170, an audio amplifier 378, the processor 220, and the memory device 224). The speaker 172 may also connect or interface with the printed circuit board 376. The network interface 174 may also connect or interface with the printed circuit board 376, and an antenna 380 transmits and propagates wireless signals. The auxiliary unit 160 may also have the USB interface 228 to the internal unit 190 (not shown for simplicity). An internal battery 382 may provide electrical power (current and voltage) to the internal components. The top 372 may have a light emitting diode 384 that connects to the printed circuit board 376. When the auxiliary unit 160 operates, the light emitting diode 384 may be supplied electrical power to provide a visual indication during operation.

FIGS. 33-35 illustrate local interpretation, according to exemplary embodiments. Here the auxiliary unit 160 receives the sensory output signals 108 and infers the user's status 106 (such as the infant's comfort 110). The auxiliary unit 160, for example, may receive the sensory output signal 108 representing the humidity 152 generated by the humidity sensor 150. The auxiliary unit 160 may further receive the sensory output signal 108 representing the temperature 164 generated by the temperature sensor 162 and the sensory output signal 108 generated by the motion sensor 112. The auxiliary unit 160 may even receive a microphone output signal 108 generated by the microphone 170. The auxiliary unit 160 may use any or all of these sensory output signal(s) 108 to infer the user's status 106 and/or comfort 110.

FIG. 34 again illustrates the electronic database 250. Here, though, the electronic database 250 is illustrated as being locally stored in the memory device 224 of the auxiliary unit 160. The auxiliary unit 160 may thus receive any sensory output signals 108 and query the electronic database 250. The auxiliary-side algorithm 222 thus instructs the auxiliary unit 160 to determine or to retrieve the corresponding predefined status 106, level of comfort 110, and/or the motor command 252. Again, while the database 250 may have any configuration, FIG. 34 simply illustrates the database 250 as the table 260 that electronically maps, relates, or associates different values and combinations of the sensory output signals 108 and motor commands 252 to the user's corresponding status 106 and/or comfort 110. Moreover, some or all of the electronic database entries may be remotely maintained at some other device or network location. Exemplary embodiments may thus perform a database lookup and identify the corresponding entries.

FIG. 35 further illustrates local interpretation. Here, though, interpretation may be performed by the internal unit 190. That is, the internal unit 190 receives any of the sensory output signals 108 and queries the electronic database 250. The internal unit 190 may thus locally store the database 250, and the internal-side algorithm 232 causes the internal unit 190 to retrieve the user's corresponding status 106, comfort 110, and/or motor command 252.

Figure 36:
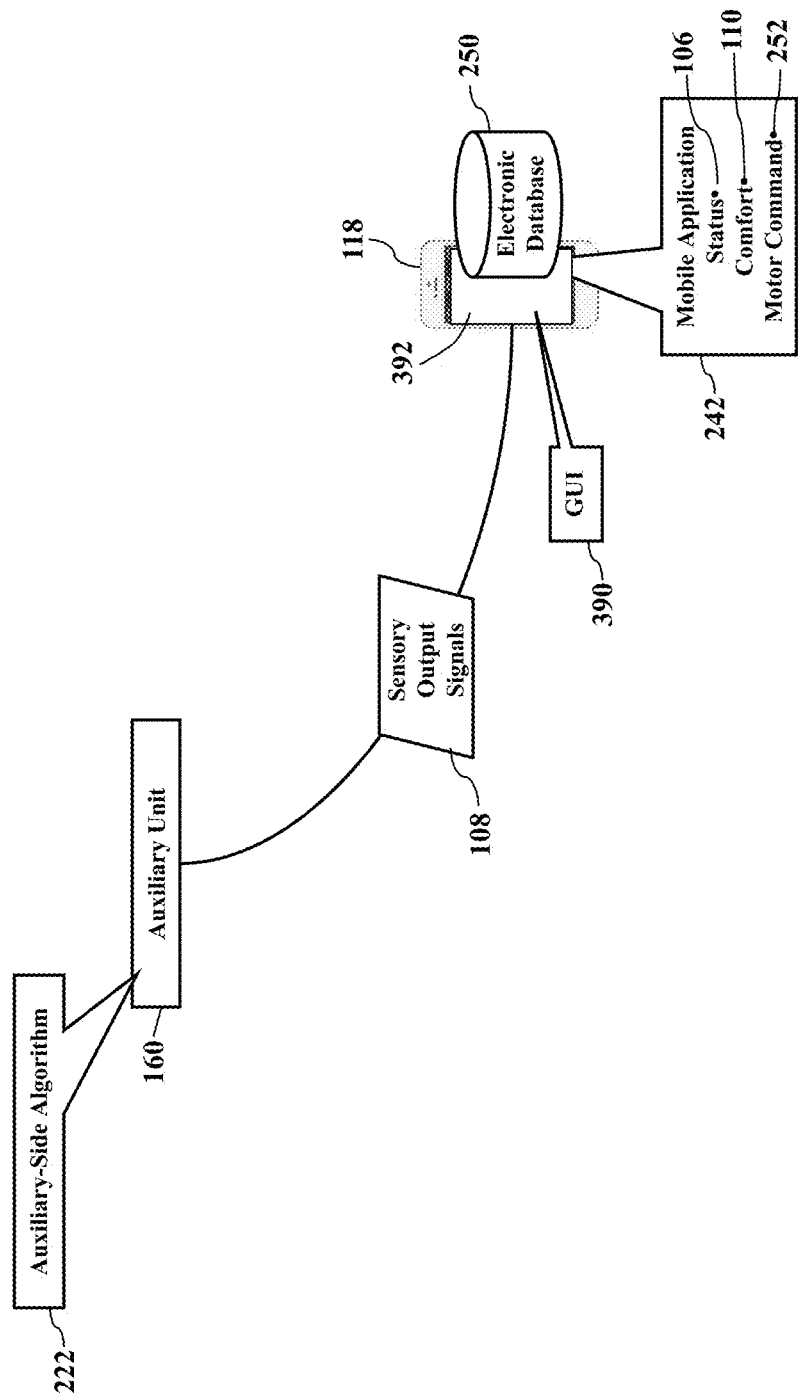

FIGS. 36-39 illustrate remote interpretation, according to exemplary embodiments. Here exemplary embodiments may forward or send the sensory output signals 108 to any remote device for a determination of the user's status 106, the comfort 110, and/or the motor command 252. FIG. 36, for example, illustrates the smartphone 118. The auxiliary unit 160 may upload the sensory output signals 108 to the smartphone 118 for analysis and interpretation. The smartphone 118 may thus locally store the electronic database 250 in the local memory device 244 (illustrated in FIG. 16). The auxiliary unit 160 may thus upload, send, or stream the sensory output signals 108 via the communications network 176 (illustrated in FIG. 16) to the network address associated with the smartphone 118. When the smartphone 118 receives the sensory output signals 108, the mobile application 242 may instruct the smartphone 118 to infer the user's status 106, the comfort 110, and/or the motor command 252 based on the sensory output signals 108. The mobile application 242 may instruct the smartphone 118 to query the database 250 and to retrieve the corresponding status 106, comfort 110, and/or motor command 252. The smartphone 118 may then generate a graphical user interface ("GUI") 390 on its display device 392. The graphical user interface 390 may thus explain or describe the status 106, the comfort 110, and/or the motor command 252 using text, images, video, and other graphical content. A parent or caregiver is thus informed of the user's comfort 110 in near-real time based on environmental and physiological data.

Figure 37:
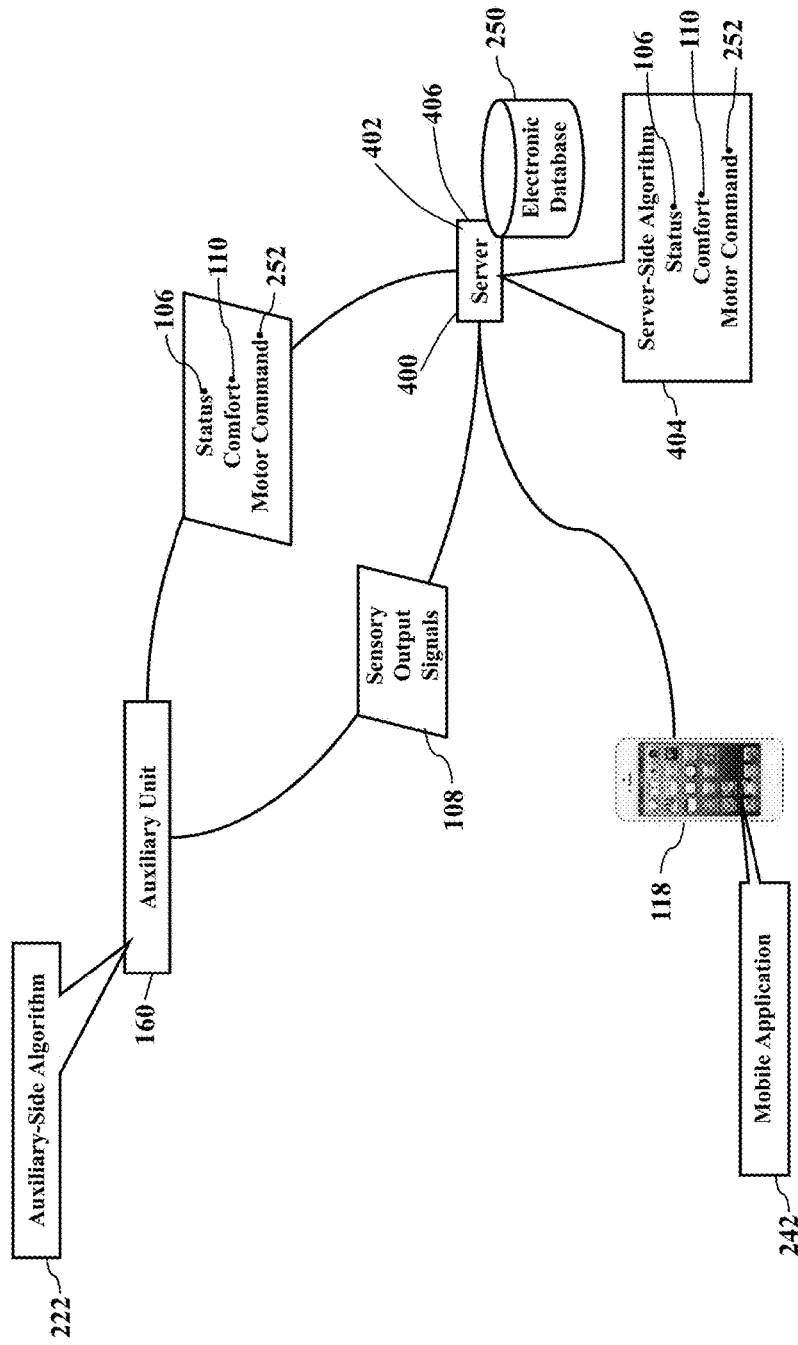

FIG. 37 illustrates a cloud-based solution. Here the auxiliary unit 160 may send the sensory output signals 108 via the communications network 176 (illustrated in FIG. 16) to a remote server 400. Suppose, for example, that the user's status 106 is determined as an online, web-based subscription service provided by a service provider. The sensory output signals 108 may be sent as a service request via a private data network, via a private cellular network, and/or via the public Internet to the network address associated with the remote server 400. When the remote server 400 receives the sensory output signals 108, the remote server 400 has a processor 402, application specific integrated circuit (ASIC), or other component that executes a server-side algorithm 404 stored in a local memory device 406. The server-side algorithm 404 may instruct the processor 402 to infer the user's status 106, based on the sensory output signals 108 sent from the auxiliary unit 160. That is, the remote server 400 may query the database 250 and retrieve the corresponding status 106, comfort 110, and/or motor command 252. The remote server 400 may then send the status 106, comfort 110, and/or motor command 252 as a service response back to the network address associated with a requesting client (such as the auxiliary unit 160). The remote server 400 may additionally or alternatively send the status 106, comfort 110, and/or motor command 252 as a message to the network address associated with the parent's smartphone 118.

Figure 38:
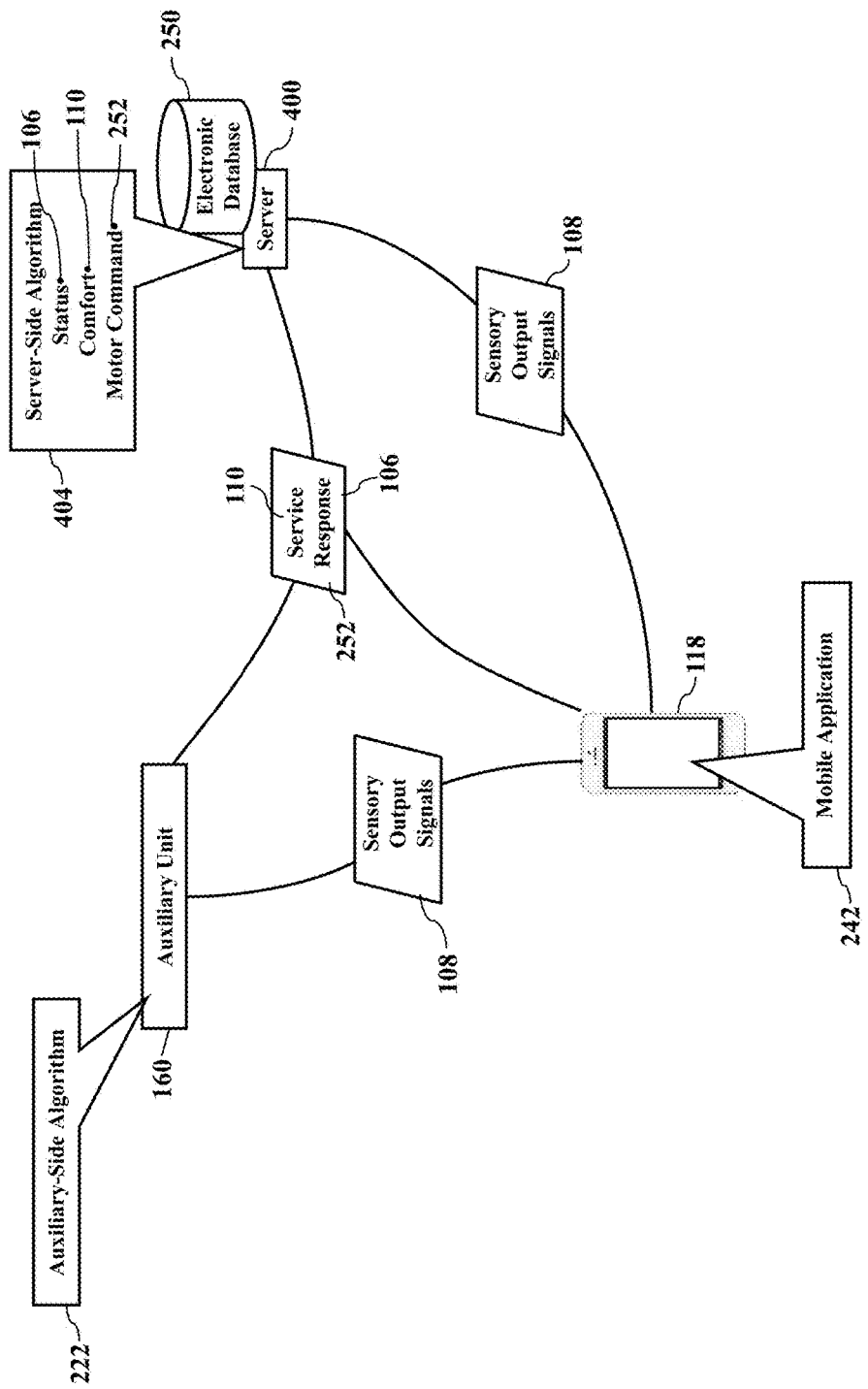

FIG. 38 also illustrates a cloud-based solution. Here, though, the auxiliary unit 160 may rely on the communications capabilities of the smartphone 118. Suppose the auxiliary unit 160 has a short range of transmission (e.g., BLUETOOTH®, ISM band, or infrared), a low battery power, or other limitation. Regardless, the auxiliary unit 160 may wirelessly send the sensory output signals 108 to the smartphone 118. When the smartphone 118 receives the sensory output signals 108, the mobile application 242 may instruct the smartphone 118 to forward or upload the sensory output signals 108 to the remote server 400 for analysis (perhaps via a WI-FI® wireless local area network and/or a wide-area cellular network). Exemplary embodiments may thus utilize the better or greater power transmissions capabilities of the smartphone 118 for remote interpretation. The remote server 400 queries the database 250 and retrieves the corresponding status 106, comfort 110, and/or motor command 252. The remote server 400 may then send the status 106, comfort 110, and/or motor command 252 as a service response back to the network address associated with the smartphone 118. The smartphone 118 may then display the user's status 106 (perhaps via the GUI 390 illustrated in FIG. 36). The smartphone 118 may additionally or alternatively wirelessly send the status 106, comfort 110, and/or motor command 252 back to the auxiliary unit 160. The remote server 400 may also send the status 106, comfort 110, and/or motor command 252 to the network address associated with the auxiliary unit 160.

Figure 39:
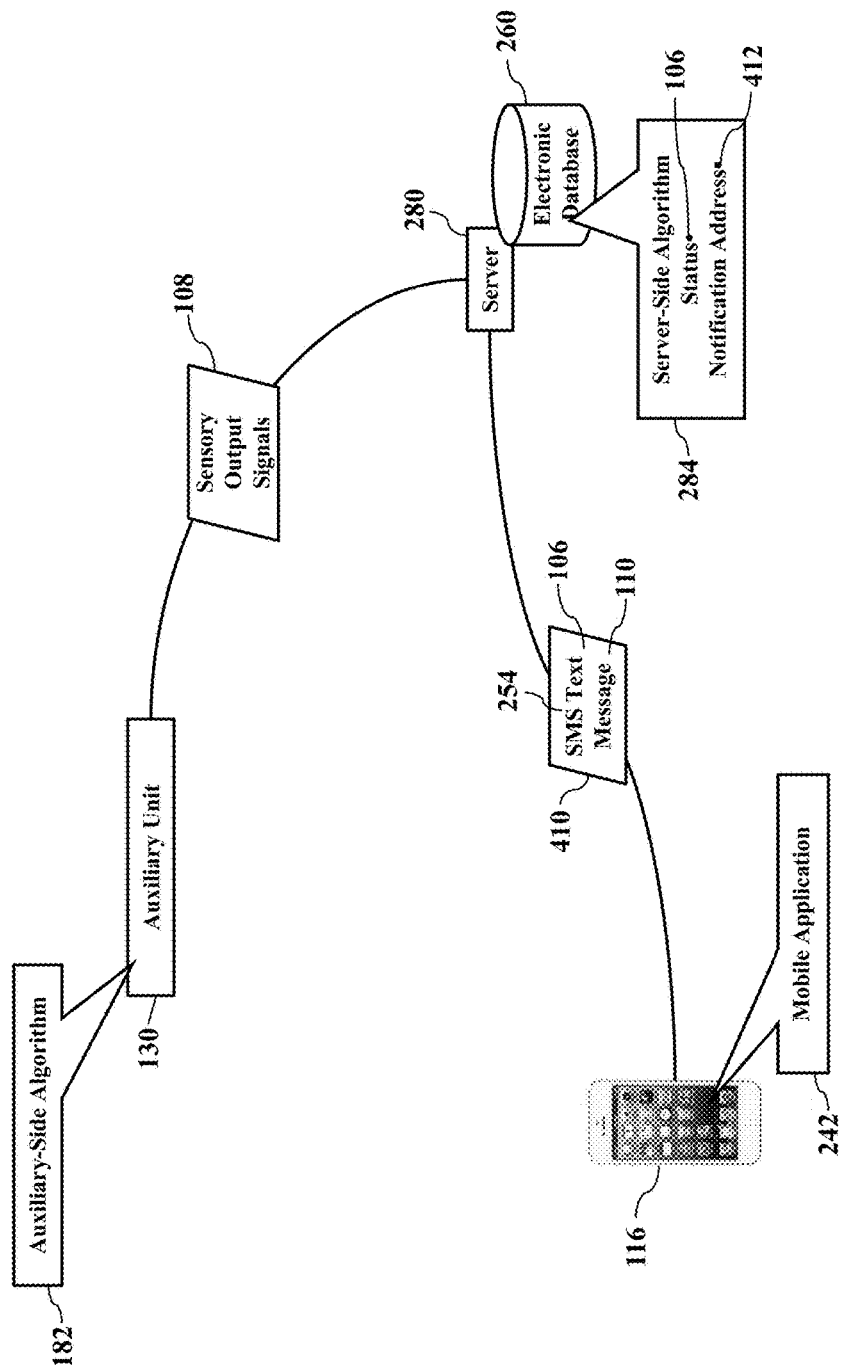

FIG. 39 further illustrates remote notification. Here exemplary embodiments may remotely notify any device or destination of the status 106, comfort 110, and/or motor command 252. Exemplary embodiments, in other words, may initiate, send, or push an electronic text message, email, webpage, or other notification to alert of the infant's discomfort, physical, and/or emotional need. As most readers are thought familiar with text messages, FIG. 39 illustrates a short messaging service ("SMS") text message 410. Suppose, for example, that the auxiliary unit 160 uploads the sensory output signals 108 to the remote server 400 for third party analysis. That is, perhaps the user subscribes to a fee-based monitoring service provided by a hospital, security service, doctor, or other service provider. The remote server 400 determines the status 106, comfort 110, and/or motor command 252 (perhaps by querying the database 250, as above explained). The remote server 400 may then retrieve one or more preprogrammed notification addresses 412, such as the cellular number associated with the smartphone 118. The remote server 400 may then initiate and/or send the status 106, comfort 110, and/or motor command 252 as the SMS text message 410 to the smartphone 118. When the smartphone 118 receives the SMS text message 410, the mobile application 242 may cause the smartphone 118 to display the information (perhaps via the GUI 390 illustrated in FIG. 36). The user (or the user's parent or caregiver) is thus remotely informed of the user's status 106.

The smartphone 118 and the auxiliary unit 160 may also remotely notify. This disclosure previously explained that the smartphone 118, or the auxiliary unit 160, may determine, or be informed of, the status 106, comfort 110, and/or motor command 252. Regardless, the smartphone 118 and the auxiliary unit 160 may also be programmed to store and to retrieve any of the notification addresses 412 and initiate the SMS text message 410 via a cellular network. The smartphone 118 and the auxiliary unit 160 may additionally or alternatively send an electronic message via WI-FI®, BLUETOOTH®, or the Internet. While exemplary embodiments may notify using any messaging standard or technology, the SMS text message 410 is thought familiar to most readers.

FIGS. 40-41 illustrate streaming audio, according to exemplary embodiments. This disclosure previously explained how the auxiliary unit 160 may include the microphone 170. The auxiliary unit 160 may thus generate analog or digital audio signals 430 representing the user's voice (such as the infant 102 illustrated in FIGS. 1-2). Exemplary embodiments may thus stream the audio signals 430 (perhaps via the communications network 176 illustrated in FIG. 16) to any destination. FIG. 40, for simplicity, again illustrates the parent's smartphone 118. The auxiliary unit 160 may send the audio signals 430 to the network address associated with the smartphone 118. The mobile application 242 may cause the smartphone 118 to audibly convert and play the audio signals 430, thus allowing the parent to remotely listen in on the infant's voice.

FIG. 41 illustrates audible responses. Here exemplary embodiments may allow a parent or other caregiver to converse with the user. Suppose, for example, the parent manually or tactilely opens the mobile application 242 and speaks into his or her smartphone 118. As the reader may understand, the smartphone 118 has a microphone and internal circuitry (not shown for simplicity) that converts speech into voice signals 432 for transmission (perhaps via the communications network 176) to the network address (e.g., Internet protocol address) associated with the auxiliary unit 160. When the auxiliary unit 160 receives the voice signals 432, the auxiliary unit 160 has processing and/or circuitry for outputting the voice signals 432 via the speaker 172. The parent may thus speak to his or her infant using the smartphone 118.

FIG. 42 illustrates musical capabilities, according to exemplary embodiments. Here the auxiliary unit 160 may play a music file 440 or receive streaming music 442. For example, suppose the auxiliary unit 160 downloads and/or locally stores the music file 440. The auxiliary unit 160 may receive a command (such as a button depression or a wireless message) that causes the auxiliary unit 160 to retrieve and to play the music file 440. The auxiliary unit 160 may thus include an audio player 444 for playing and outputting music via the speaker 172. The auxiliary unit 160 may additionally or alternatively wirelessly receive the streaming music 442 as audio data from a streaming service. Suppose, for example, that the parent's smartphone 118 sends the streaming music 442 (perhaps via the communications network 176) to the network address associated with the auxiliary unit 160. The audio player 444 may thus process the streaming music 442 for output via the speaker 172.

FIGS. 43-45 are screenshots illustrating parameter settings, according to exemplary embodiments. Here the mobile application 242 may cause any device (such as the smartphone 118 discussed herein) to display configuration options and settings for monitoring one or more users. The mobile application 242 may thus instruct the smartphone 118 to generate the graphical user interface 390 on the display device 392 (illustrated in FIG. 36). A user of the smartphone 118 makes inputs that define the monitoring activities of the user lying in the monitoring system 100 (illustrated in FIGS. 1-2). FIG. 43, for example, illustrates a settings screen in which different monitored users (such as different babies) may be selected and added. FIG. 44 illustrates another settings screen for selection of measurement parameters (such as metric or English units). FIG. 45 illustrates still another settings screen for configuring the sensors 104 (illustrated in FIGS. 1-6 and 16). Exemplary embodiments may have additional settings for establishing user accounts, passwords, and the notification addresses 412 (illustrated in FIG. 39).

Figure 47:
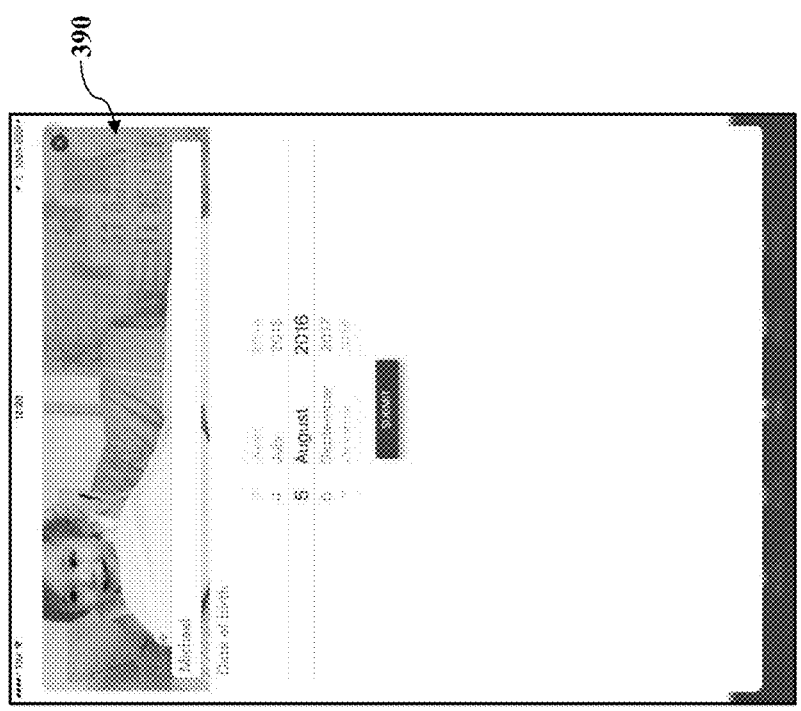
Figure 48:
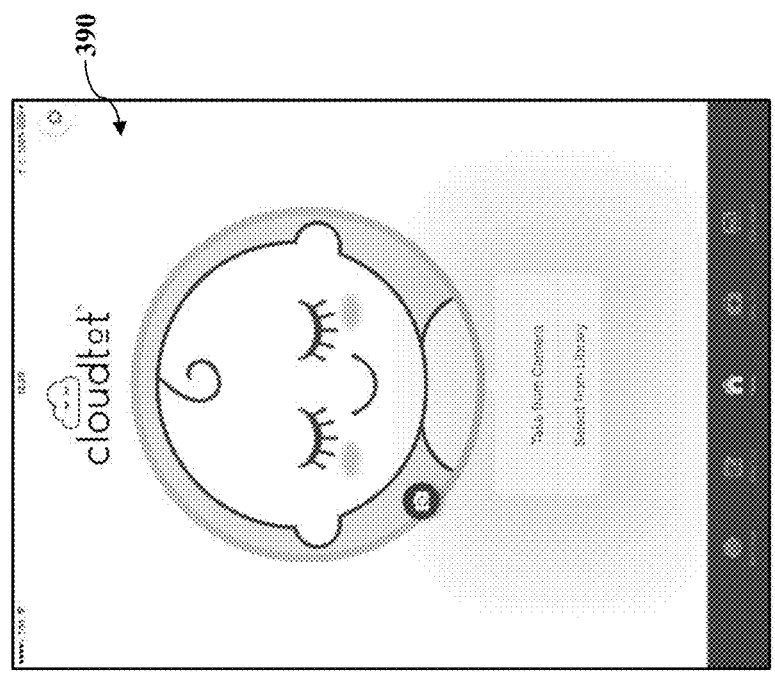
Figure 49:
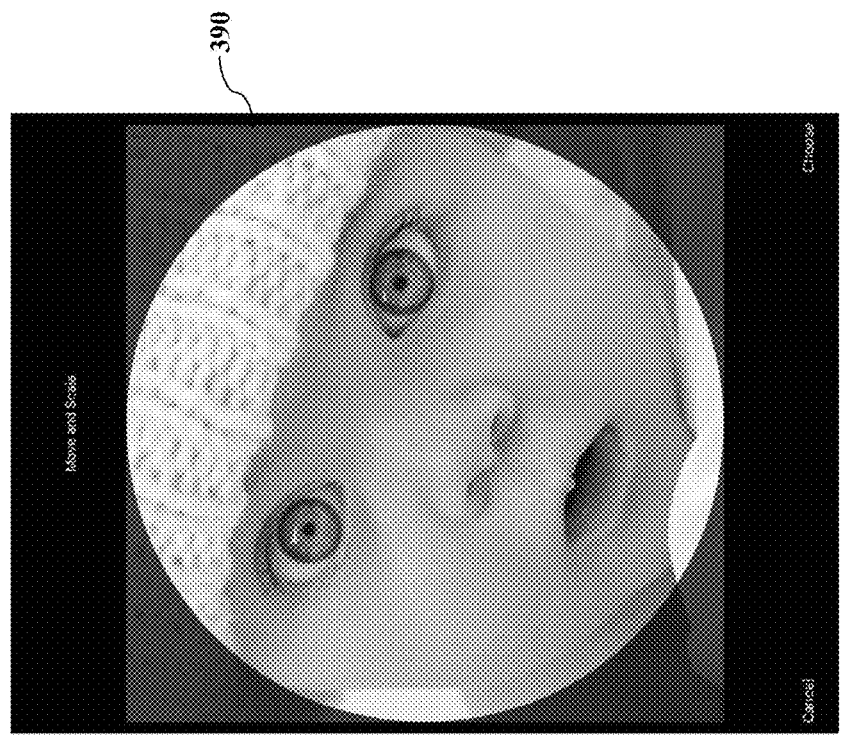
Figure 50:
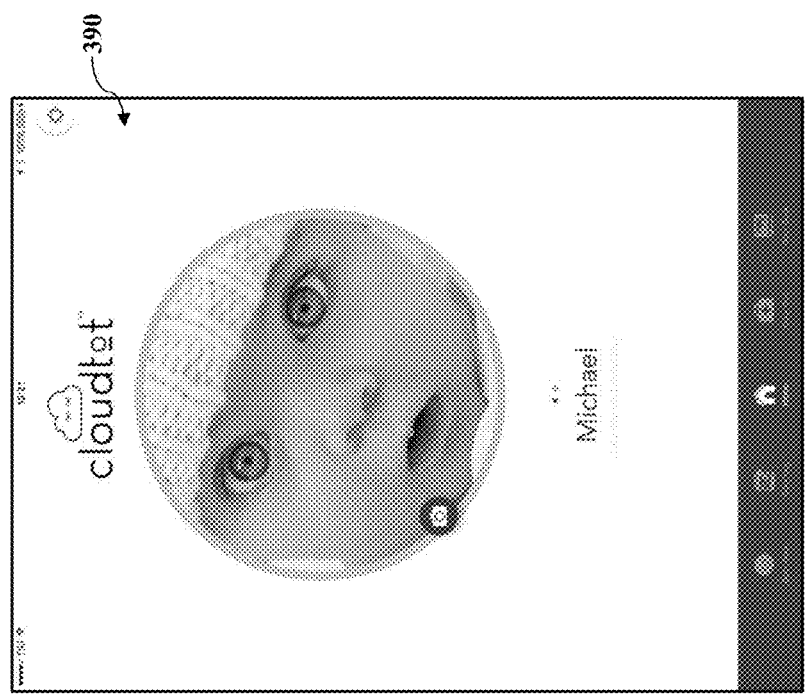

FIGS. 46-50 are screenshots for manually adding infant users, according to exemplary embodiments. This disclosure previously explained how exemplary embodiments may monitor one or more infant users (such as the infant 102 illustrated in FIGS. 1-2). Exemplary embodiments may thus include options and settings for adding a new profile that corresponds to an infant user. FIG. 47 is a screenshot for entering the infant's name and birthdate. FIG. 48 is a screenshot for selecting an image to associate with the infant's profile. FIG. 49 illustrates manipulation of the selected image (such as zoom and crop). FIG. 50 thus illustrates the final profile screen displaying the infant's name and image.

Figure 51:
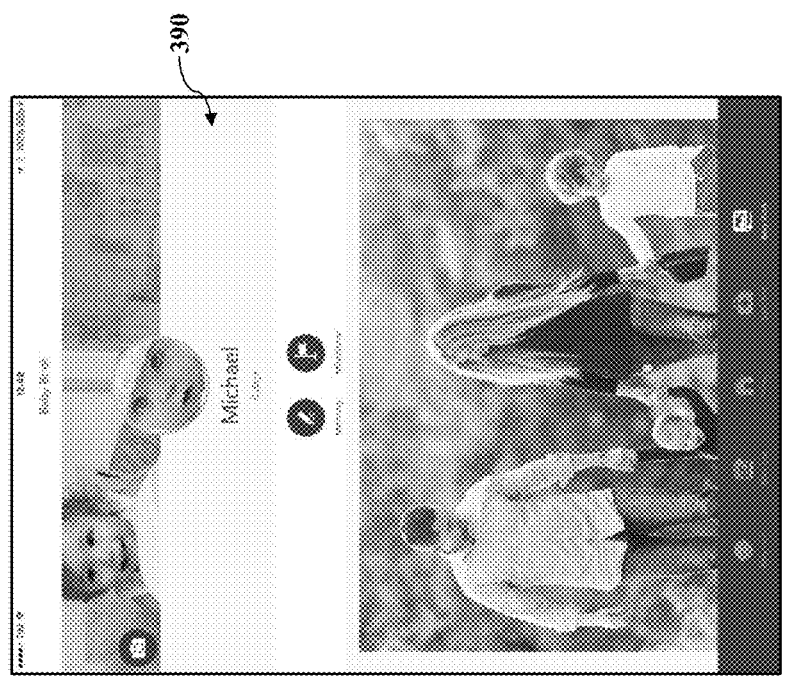
Figure 52:
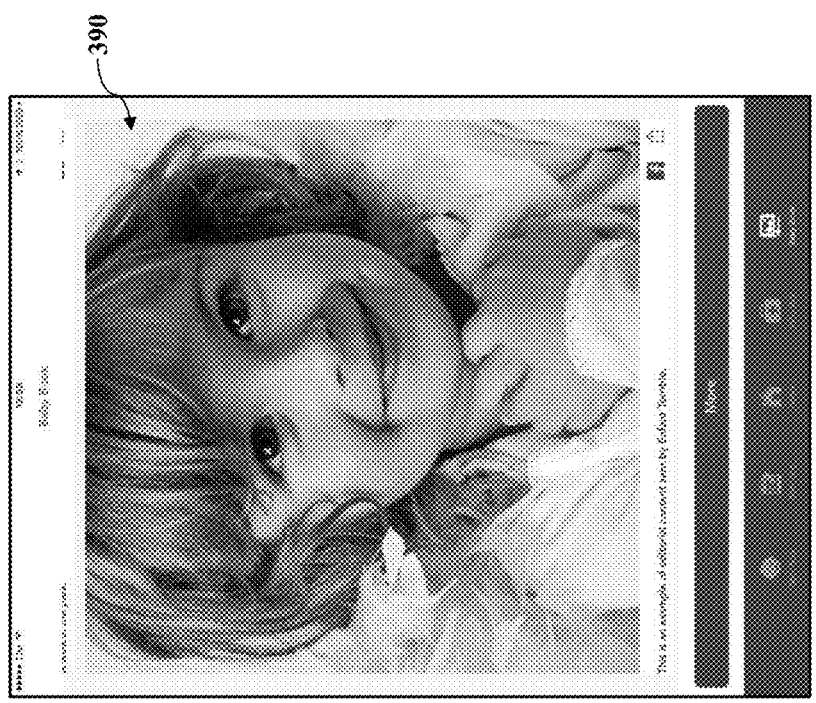
Figure 53:
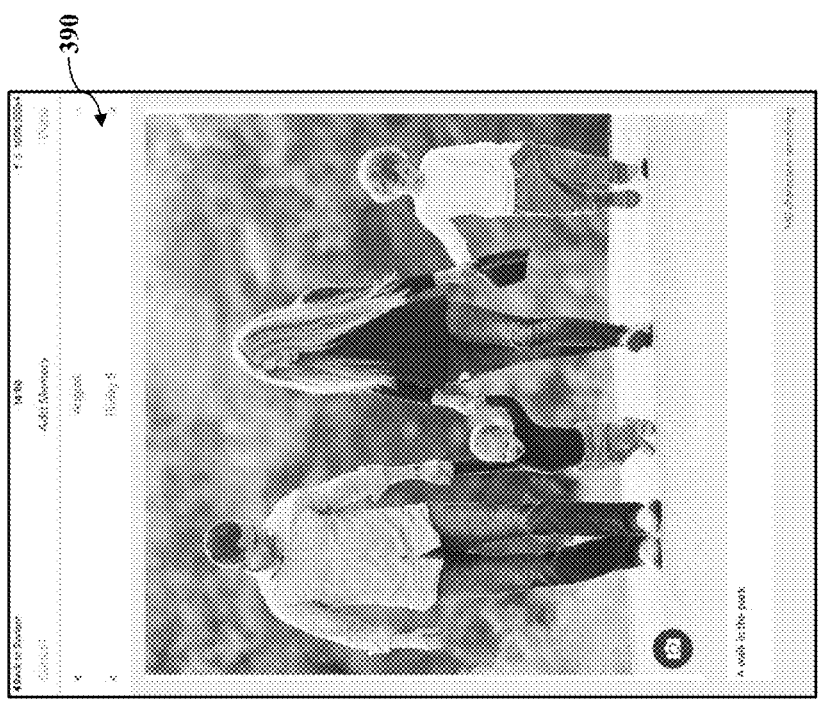
Figure 54:
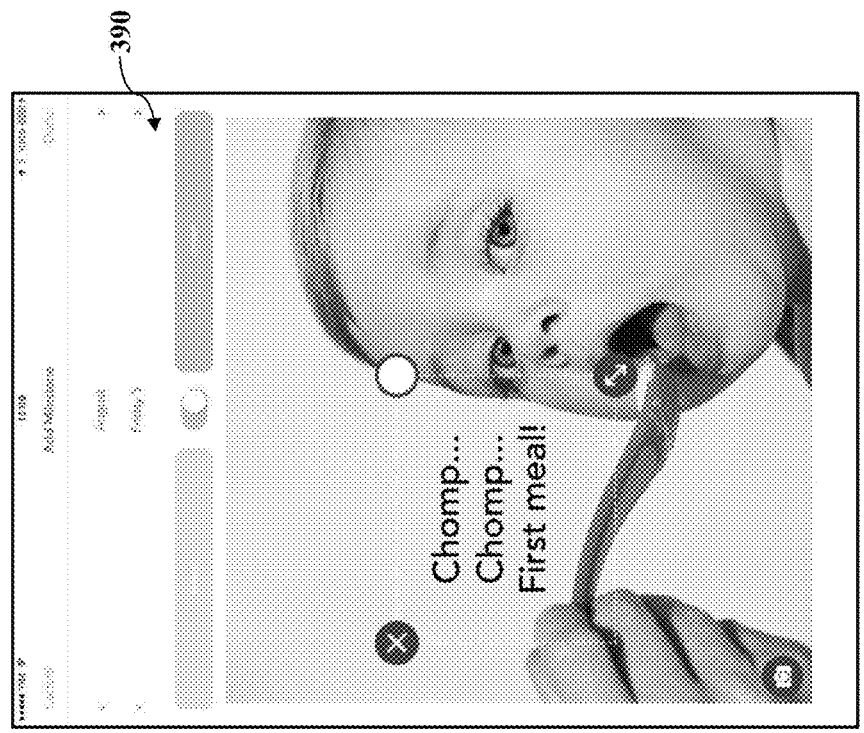

FIGS. 51-54 are screenshots for establishing a baby book, according to exemplary embodiments. As the reader likely understands, parents and family often collect photos, memorial moments, milestone moments, and artwork that document the infant's growing years. Exemplary embodiments may automatically archive these historical artifacts as electronic files in a so-called baby book. As any electronic image is added to the infant's baby book, exemplary embodiments may allow the parent to enter a textual description and/or date and time associated with any electronic image (FIGS. 51-53). Exemplary embodiments may also allow any electronic image to be captioned with text and other graphics (FIG. 54).

FIGS. 55-57 are screenshots for calendric recordings, according to exemplary embodiments. Here exemplary embodiments allow the parent or other caregiver to track appointments, medications, and other calendar events according to date and time. FIG. 55, for example, illustrates a monthly calendar view of upcoming events, while FIG. 56 illustrates a daily view. The parent may thus add, modify, and delete calendar entries and establish reminder notifications (FIG. 57).

FIG. 58 is a screenshot illustrating logging capabilities, according to exemplary embodiments. Here exemplary embodiments may store and historically track the infant's growth over time. As the infant's profile grows over time, the profile may include historical entries and data describing the infant's weight, height, and other physical measurements. FIG. 58 thus illustrates an electronic graph of these measurements according to time.

Figure 59:
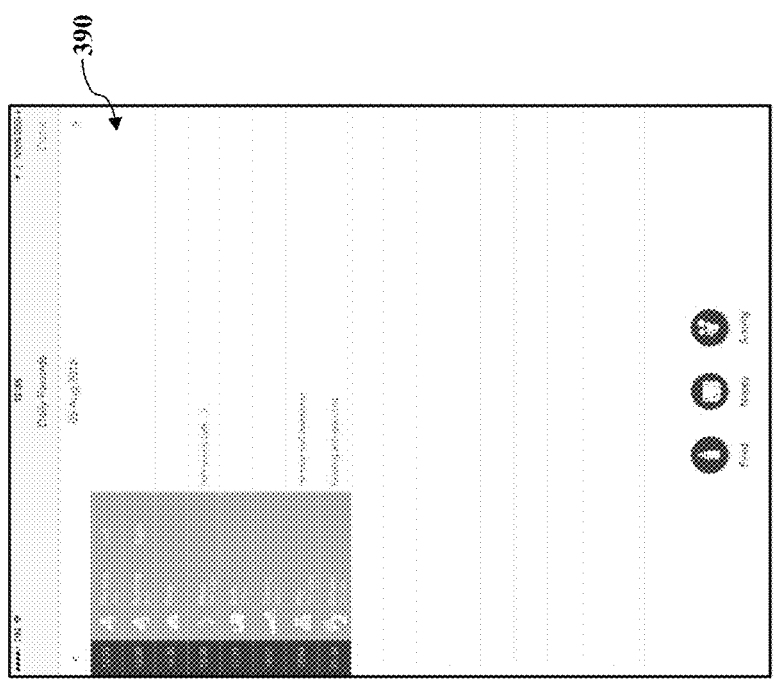
Figure 60:
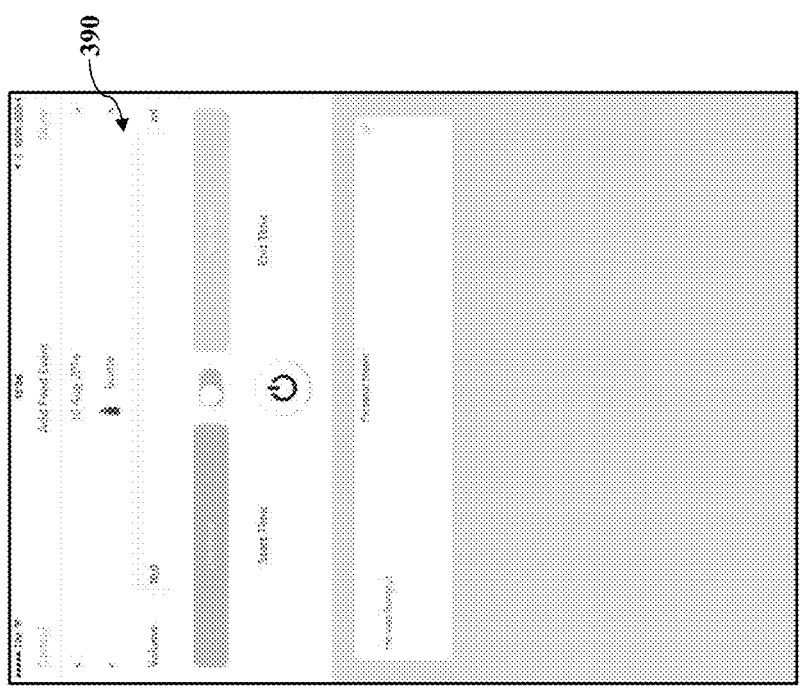
Figure 61:
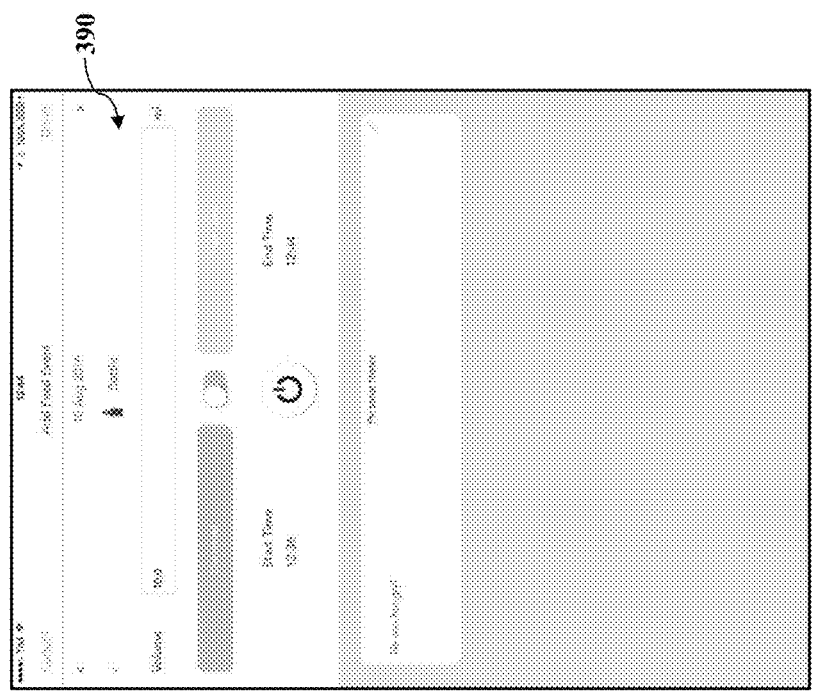
Figure 62:
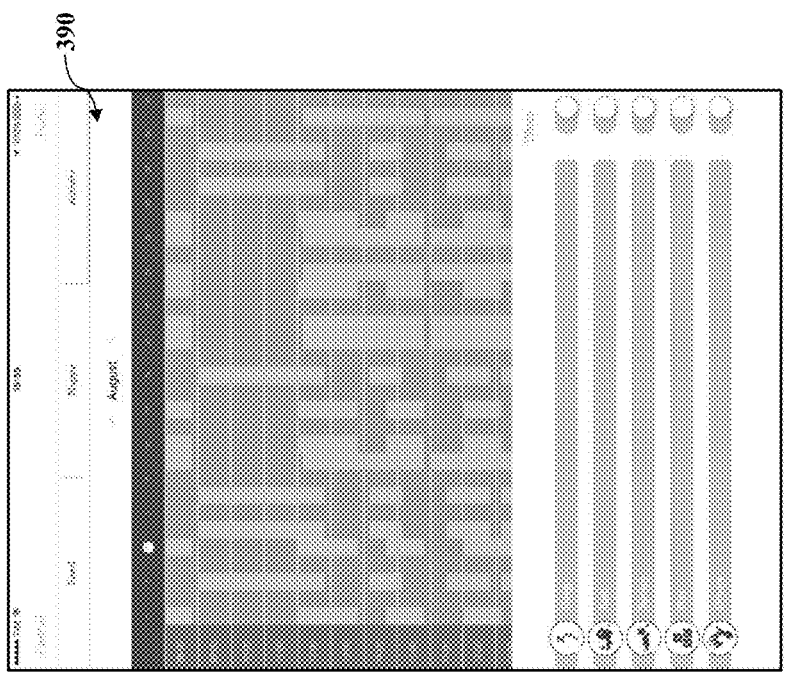
Figure 63:
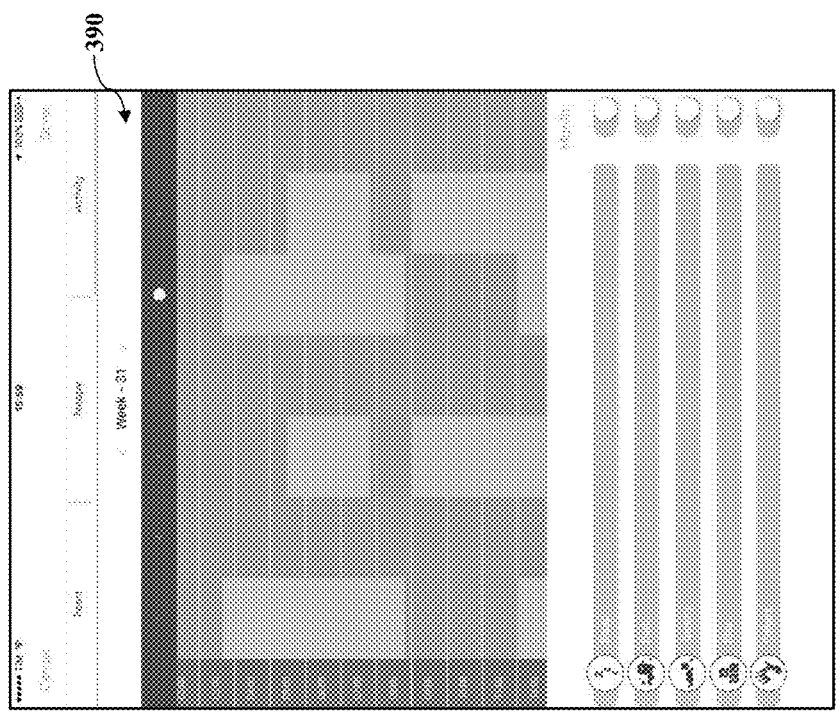
Figure 64:
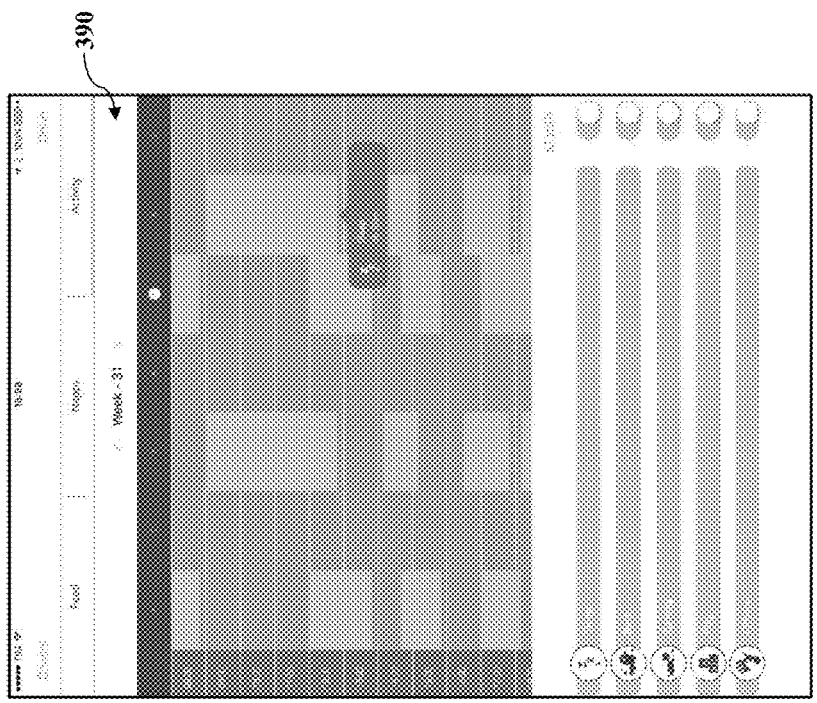

FIGS. 59-64 are screenshots illustrating electronic logs, according to exemplary embodiments. This disclosure previously explained the electronic log 314 (illustrated in FIG. 25) that stores a rich repository of the sensory output signals 108 representing the infant's status 106, comfort 110, and other data. Exemplary embodiments may thus log daily and other time-based activities. FIG. 59, for example, illustrates daily activities according to time. The parent may thus make inputs to his or her smartphone 118 to add, modify, and delete entries describing the infant's activities. FIGS. 60-61 illustrate documentary evidence of any activity. That is, the parent may use the smartphone's audio, video, and photographic capabilities to electronically document any activity with timestamping data. FIGS. 62-64 illustrate monthly and weekly logs of any activity (such as sleep time, bath time, tummy time, and play time), along with explanatory popup messages or other textual descriptors.

FIGS. 65-67 are alternative configurations of the contact mechanism 140, according to exemplary embodiments. Here the pegs 210a and 210b may extend through the cushioned pad 122 or mattress 123 to arouse the user lying in the monitoring system 100. This disclosure previously explained how the internal unit 190 may be alternatively incorporated within the cushioned pad 122 or mattress 123 (as illustrated with reference to FIGS. 14 and 29). That is, the cushioned pad 122 or mattress 123 may have the internal cavity 192 into which the internal unit 190 inserts (as FIG. 14 previously illustrated). Because the cushioned pad 122 or mattress 123 may sit below the upper textile product 180, here the cushioned pad 122 or mattress 123 may incorporate the internal unit 190 and, thus, the contact mechanism 140. The peg 210 may thus reciprocate into contact with the cushioned pad 122 or mattress 123. However, the peg 210 may optionally reciprocate within the cushioned pad 122 or mattress 123. That is, the cushioned pad 122 or mattress 123 may have an internal hollow shaft 650 in which the peg 210 slides. Exemplary embodiments may thus arrange the peg 210 for proximate contact with the infant 102 for maximum effect.

FIGS. 66-67 are partial cross-sectional views of an exemplary embodiment of the cushioned pad 122 or mattress 123. Even though the cushioned pad 122 or mattress 123 may have an inner material (such as inner material 652), which may be for example a foam filling, the peg 210 may slide up and down within the hollow shaft 650 (perhaps via the rocker arm 272, as explained with reference to FIG. 20). The hollow shaft 650 may be molded, machined, or drilled into the inner material 652. The hollow shaft 650 may have a rigid inner surface 654 defining a longitudinal axis LA-LA (illustrated as reference numeral 656). While FIG. 66 illustrates a cylindrical cross-sectional shape, the peg 210 and the hollow shaft 650 may have any cross-sectional shape. As FIG. 67 illustrates, a cylindrical sleeve 658 may be inserted, pressed, or molded into the hollow shaft 650. The peg 210 may slide within the cylindrical sleeve 658. The cylindrical sleeve 658 may thus have material properties that provide a less frictional and more durable surface. The outer diameter of the peg 210 and the inner diameter of the hollow shaft 650 and/or the cylindrical sleeve 658 may be selected to provide a desired clearance there between.

FIGS. 68-69 illustrate linear translation, according to exemplary embodiments. Here the peg 210 upwardly moves a linear distance (or stroke) 680 to impart the force 256. FIG. 68 illustrates a cross-sectional view of a portion of an example monitoring system 100 including cushioned pad 122 with an overlying mattress 123. The internal unit 190 slides into the cushioned pad 122 (as explained with reference to FIGS. 6-8). When the peg 210 is driven, the peg 210 upwardly extends from the internal unit 190 and strikes a material ceiling 681 demarcating an upper, internal region 682 of the cushioned pad 122. Because the cushioned pad 122 has an inner construction 684 (such as foam, cotton, cellulose, or other fabric or material), the peg 210 locally compresses the material ceiling 681 and the force 256 propagates through the upper, internal region 682 (and perhaps through the conductive strands 202) and into the mattress 123. The force 256 continues propagating through the inner material 652 of the mattress 123 and manifests itself on an exterior surface 686. The force 256 may also propagate through a mattress cover 688 (if any, and perhaps through the conductive strands 202 if present in cover 688). The force 256 causes the exterior surface 686 to at least locally elevate, lift, or heave, thus causing a tactile sensation at the infant 102. Exemplary embodiments may thus be configured to slide the peg 210 to impart the force 256 that propagates through whatever material thickness of the upper, internal region 682 of the cushioned pad 122 and the mattress 123. In plain words, the exterior surface 686 of the mattress 123 is disturbed with an amplitude, motion, and/or magnitude that provokes a response in the infant 102.

FIG. 69 illustrates the alternative arrangement. Here the internal unit 190 is contained within the mattress 123 to arouse the infant 102. Because the internal unit 190 may alternatively be inserted from below into the internal cavity 192 (as illustrated with reference to FIGS. 14 and 29), the peg 210 may reciprocate (through its stroke 680) into contact with a material ceiling 689 demarcating an upper, internal region 690 of the mattress 123. As the peg 210 strikes the material ceiling 689, the force 256 propagates through the inner material 652 of the upper, internal region 690 and manifests itself on the exterior surface 686 of the mattress 123 (and perhaps through the conductive strands 202, if present). The force 256 may also propagate through the mattress cover 688 (if any). The force 256 causes the exterior surface 686 to at least locally elevate, lift, or heave, thus causing a tactile sensation at the infant 102. Exemplary embodiments may thus be configured to slide the peg 210 to impart the force 256 that propagates through whatever material thickness of the upper, internal region 690 of the mattress 123. The exterior surface 686 of the mattress 123 is disturbed with an amplitude, motion, and/or magnitude that provokes a response in the infant 102. In the above example, internal unit 190 may be contained within cushioned pad 122 instead of mattress 123 with the same effect and operation as described above.

Design choices may be made. As the reader may now envision, the inner construction 684 of the cushioned pad 122 and/or the inner material 652 of the mattress 123 may affect the magnitude and propagation of the force 256. Moreover, the material thicknesses of the upper, internal region 682 of the cushioned pad 122 and/or the upper, internal region 690 of the mattress 123 may also affect the magnitude and propagation of the force 256. The rotational speed of the motor 254 and mechanical leverages (e.g., the profiles of the cams 274a and 274b, the length of the rocker arms 272a and 272b, the stroke 680, and the forces of the springs 280a and 280b) may also affect the magnitude and propagation of the force 256. Exemplary embodiments may thus have many design variables that are represented as the entries in the electronic database 250 (such as illustrated in FIG. 18). The motor command 252, in other words, may be based on many design variables that best impart the force 256 to provoke a response in the infant 102

Alternative exemplary embodiments may even contact the infant 102. As the reader may envision, the peg 210 may extend through the exterior surface 686 of the mattress 123 (or cushioned pad 122) to impart the force 256 directly onto the infant's back, stomach, or other body area. The mattress 123 (or cushioned pad 122) may thus have an outer or upper opening or aperture exposing the hollow shaft 650 (illustrated in FIGS. 66-67). The hollow shaft 650 may entirely extend through the inner material 652 of the mattress 123 (or cushioned pad 122), thus having open ends through which the peg 210 reciprocates. As the peg 210 slides up-and-down, the peg 210 passes through the aperture and extends above or beyond the exterior surface 686 of the mattress 123. As the peg 210 protrudes, the peg 210 periodically contacts the infant 102. As the mattress 123 (or cushioned pad 122) may have the mattress cover 688 (or cushioned pad 122 cover), fabric material and fit may be selected to stretch as the peg 210 lifts, thus reducing or eliminating wear and tear on sheets. The force 256 and the stroke 680 may also be chosen to ensure the nudge or poke is tactilely felt through the infant's clothing.

It should be appreciated that cushioned pad 122 and mattress 123 may be one in the same, that is monitoring system 100 may include only cushioned pad 122, and in such an embodiment cushioned pad 122 functions as mattress 123. Monitoring system 100 may alternatively include only mattress 123, and in such an embodiment mattress 123 functions as cushioned pad 122. Monitoring system 100 may alternatively include both mattress 123 and a cushioned pad 122, and in such an embodiment mattress 123 may overlay cushioned pad 122 and vice versa.

Figure 70:
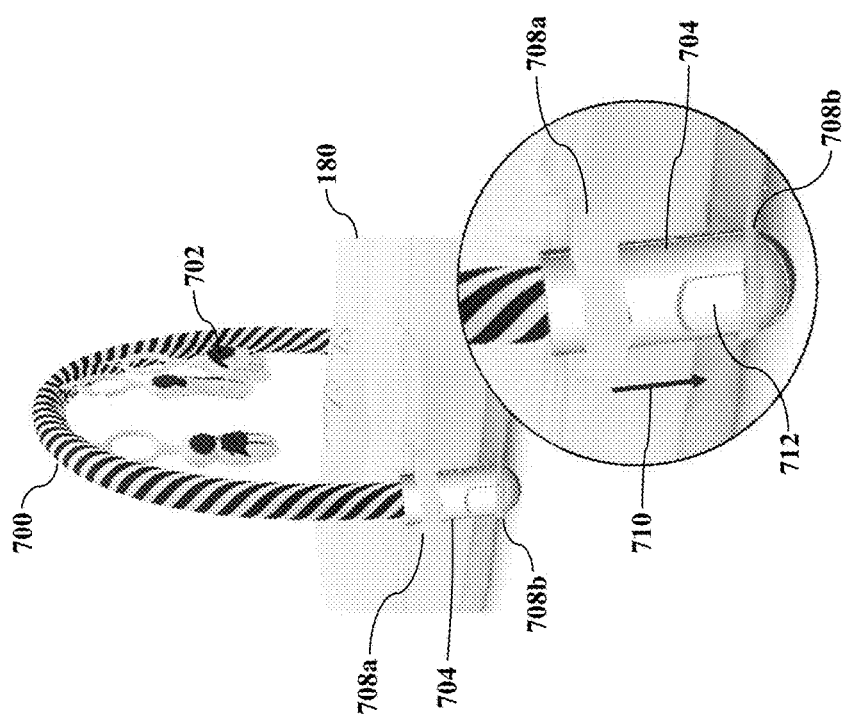
Figure 71:
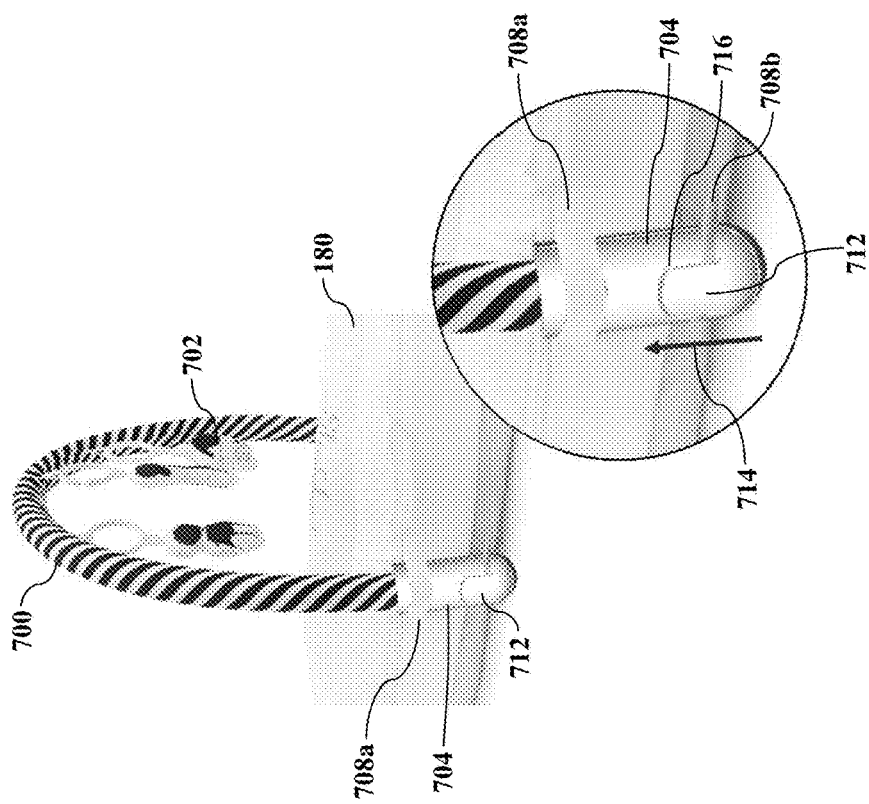
Figure 72:
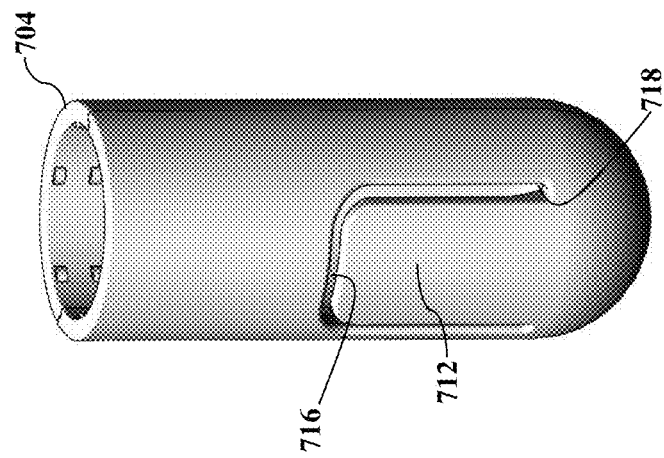
Figure 73:
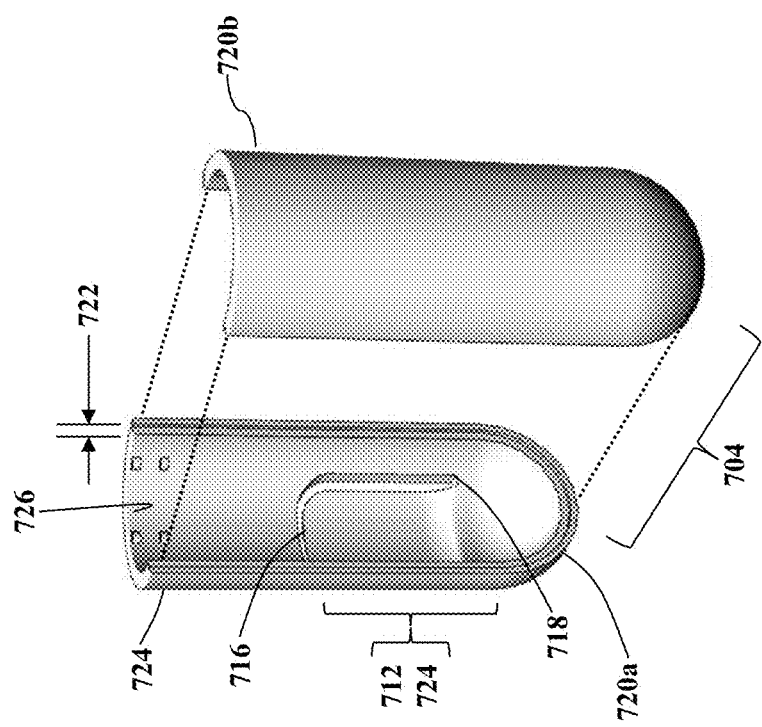

FIGS. 70-73 illustrate a suspension arch 700, according to exemplary embodiments. The suspension arch 700 may attach to the monitoring system 100 for hanging objects, such as toys and the like. Because this disclosure often describes an infant user, FIG. 70 illustrates a toy 702 dangling from the suspension arch 700. While the suspension arch 700 may have any attachment mechanism, this disclosure illustrates a male end 704 that inserts into and through side straps 708a and 708b sewn or attached to the outer shell 186 of the textile product 180. Although not shown, the suspension arch 700 may have a similar attachment mechanism at an opposite side of the textile product 180. FIG. 70, for example, illustrates an insertion (illustrated by arrow 710) of the male end 704 into and through dual side straps 708a and 708b. As the male end 704 is downwardly pushed through the lower strap 708b, the strap 708b slides over a strap slot 712. FIG. 71 thus illustrates an engagement (illustrated by arrow 714) with the strap slot 712. As male end 704 is upwardly pulled through the lower strap 708b, an edge of the lower strap 708b may catch or insert into an opening 716 of the strap slot 712. Further upward motion of the male end 704 seats the lower strap 708b at a terminus end 718 (FIG. 72) of the strap slot 712. As FIG. 73 best illustrates, the male end 704 may have engaging body halves 720a and 720b. The strap slot 712 is formed, machined, or molded into the body half 720a. The body half 720a thus has a material thickness 722 extending from an outer surface 724 to an inner surface 726. The strap slot 712 thus forms a tab 724 for catching the lower strap 708b, thus securing and maintaining the suspension arch 700 in a substantially vertical orientation. Alternatively, male end 704 may be formed as unitary body.

Figure 74:
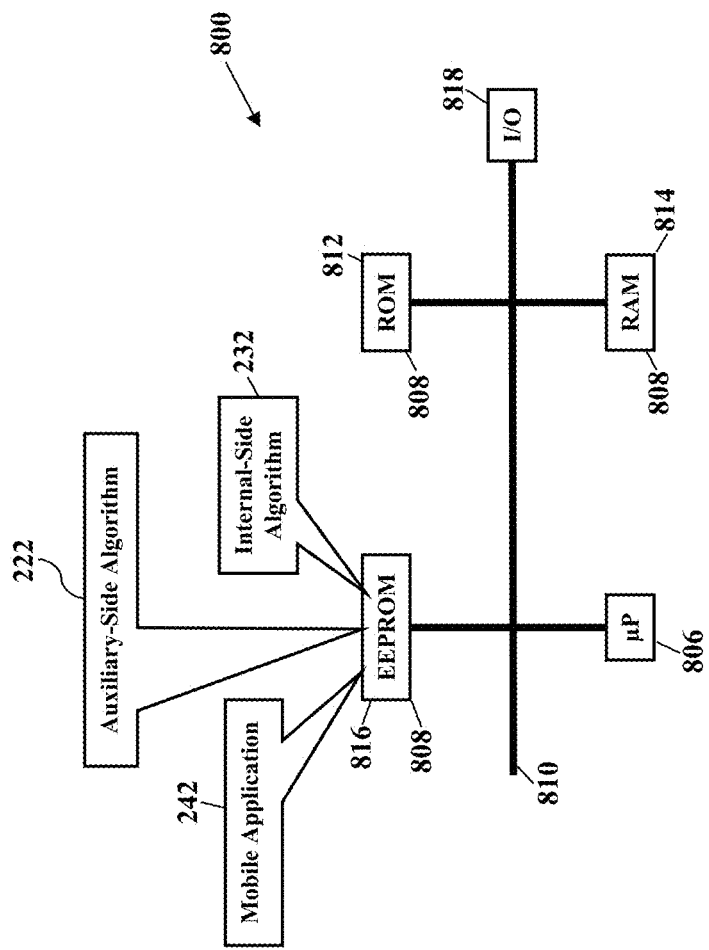
Figure 75:
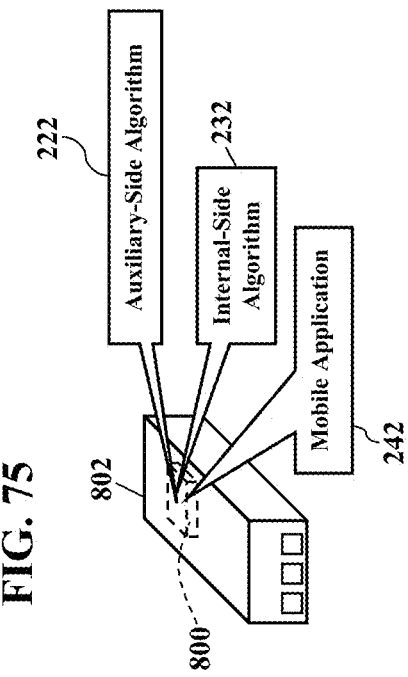
Figure 76:
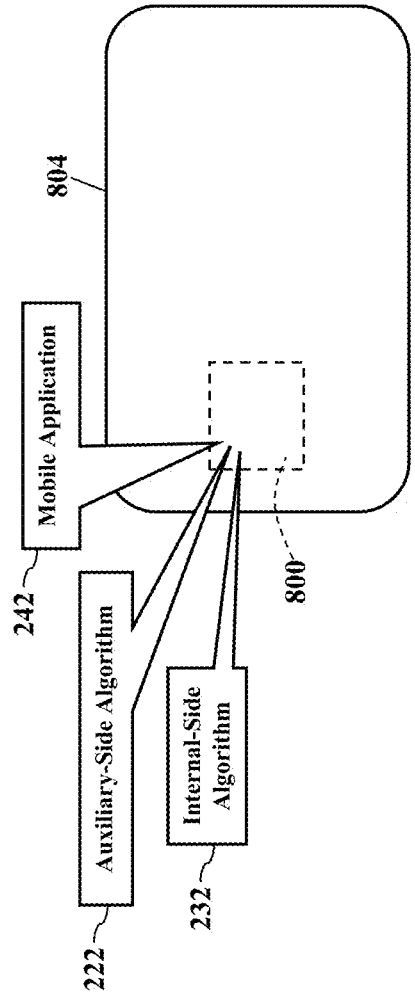

FIGS. 74-77 are schematics further illustrating operating environments for additional aspects of the exemplary embodiments. This disclosure explains how the mobile smartphone 118, the auxiliary unit 160, and/or the internal unit 190 may establish communication via the communications network 176 (as illustrated with reference to FIG. 16). Both the auxiliary unit 160 and the internal unit 190 may have wired or wireless transmission capabilities (such as the transceiver 226 illustrated in FIG. 16). While exemplary embodiments may utilize any wireless technology (such as BLUETOOTH or WI-FI), FIGS. 74-76 illustrate a cellular capability. That is, FIG. 74 is a block diagram of a Subscriber Identity Module 800, while FIGS. 75 and 76 illustrate, respectively, the Subscriber Identity Module 800 embodied in a plug 802 and in a card 804. As those of ordinary skill in the art recognize, the Subscriber Identity Module 800 stores user information (such as an International Mobile Subscriber Identity, cellular number of other identifier, Ki number, and other user information) and any portion of the auxiliary-side algorithm 222, the internal-side algorithm 232, and/or the mobile application 242. As those of ordinary skill in the art also recognize, the plug 802 and the card 804 each may physically or wirelessly interface with the mobile smartphone 118, the auxiliary unit 160, and/or the internal unit 190 (as illustrated in FIG. 16).

FIG. 74 is a block diagram of the Subscriber Identity Module 800, whether embodied as the plug 802 of FIG. 75 or as the card 804 of FIG. 76. Here the Subscriber Identity Module 800 comprises a microprocessor 806 (μP) communicating with memory modules 808 via a data bus 810. The memory modules 808 may include Read Only Memory (ROM) 812, Random Access Memory (RAM) and or flash memory 814, and Electrically Erasable-Programmable Read Only Memory (EEPROM) 816. The Subscriber Identity Module 800 stores some or all of the auxiliary-side algorithm 222, the internal-side algorithm 232, and/or the mobile application 242 in one or more of the memory modules 808. FIG. 74 shows the auxiliary-side algorithm 222, the internal-side algorithm 232, and/or the mobile application 242 residing in the Erasable-Programmable Read Only Memory 816, yet either may alternatively or additionally reside in the Read Only Memory 812 and/or the Random Access/Flash Memory 814. An Input/Output module 818 handles communication between the Subscriber Identity Module 800 and the communications device. Because Subscriber Identity Modules are well known in the art, this disclosure need not further explain the operation and the physical/memory structure of the Subscriber Identity Module 800.

Figure 77:
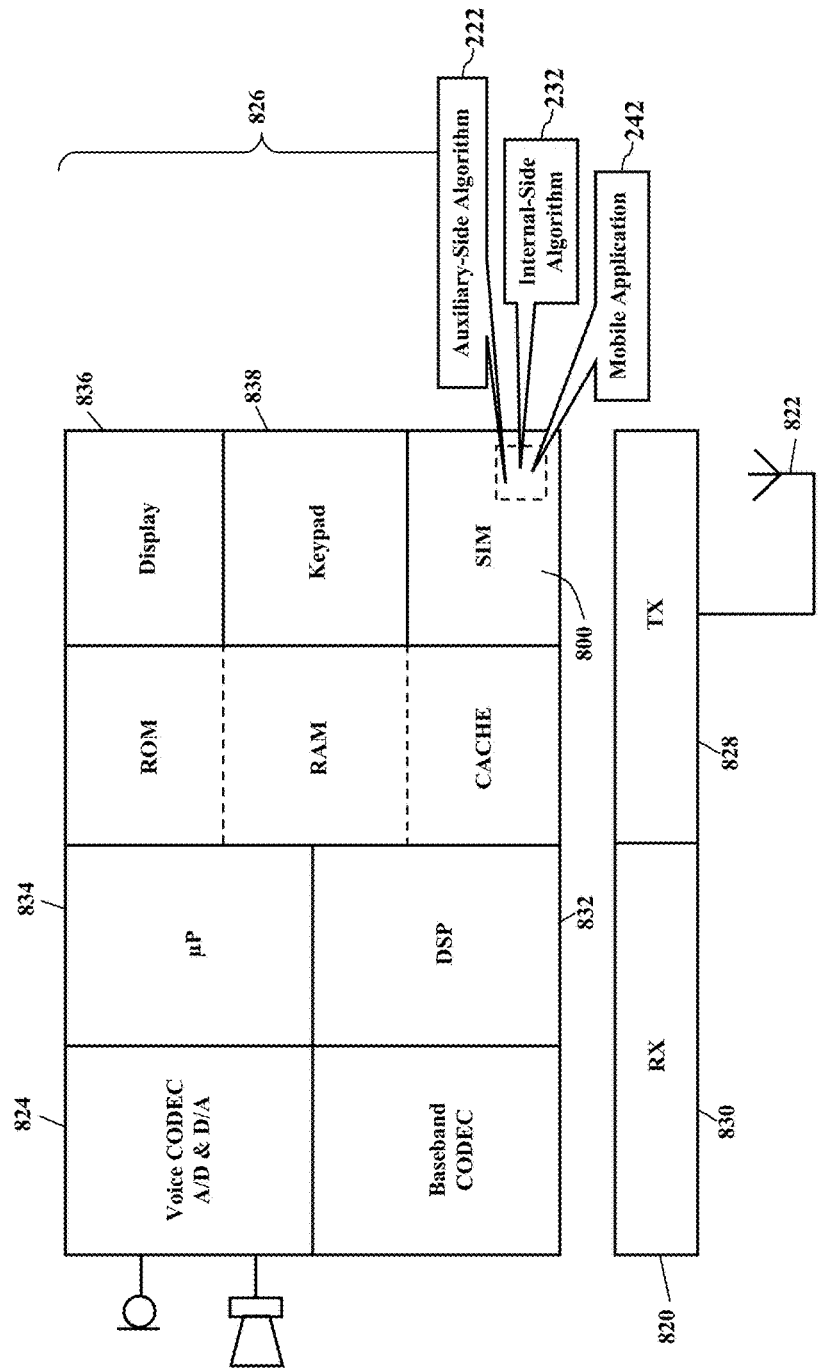

FIG. 77 is a schematic further illustrating the operating environment, according to exemplary embodiments. FIG. 77 is a block diagram illustrating some componentry of the mobile smartphone 118, the auxiliary unit 160, and/or the internal unit 190. The componentry may include one or more radio transceiver units 820, an antenna 822, a digital baseband chipset 824, and a man/machine interface (MMI) 826. The transceiver unit 820 includes transmitter circuitry 828 and receiver circuitry 830 for receiving and transmitting radio-frequency (RF) signals. The transceiver unit 820 couples to the antenna 822 for converting electrical current to and from electromagnetic waves. The digital baseband chipset 824 contains a digital signal processor (DSP) 832 and performs signal processing functions for audio (voice) signals and RF signals. The digital baseband chipset 824 may also include an on-board microprocessor 834 that interacts with the man/machine interface (MMI) 826. The man/machine interface (MMI) 826 may comprise a display device 836, a keypad 838, and the Subscriber Identity Module 800. The on-board microprocessor 834 may also interface with the auxiliary-side algorithm 222, the internal-side algorithm 232, and/or the mobile application 242.

Exemplary embodiments may be applied to any signaling standard. As those of ordinary skill in the art recognize, FIGS. 74-77 may illustrate a Global System for Mobile (GSM) communications device. That is, exemplary embodiments may utilize the Global System for Mobile (GSM) communications signaling standard. Those of ordinary skill in the art, however, also recognize that exemplary embodiments are equally applicable to any communications device utilizing the Time Division Multiple Access (TDMA) signaling standard, the Code Division Multiple Access signaling standard, the "dual-mode" GSM-ANSI Interoperability Team (GAIT) signaling standard, or any variant of the GSM/CDMA/TDMA/GAIT signaling standard. Exemplary embodiments may also be applied to other standards, such as the I.E.E.E. 802 family of standards, the Industrial, Scientific, and Medical band of the electromagnetic spectrum, BLUETOOTH®, and any other.

Exemplary embodiments may be physically embodied on or in a computer-readable storage medium. This computer-readable medium, for example, may include CD-ROM, DVD, tape, cassette, floppy disk, optical disk, memory card, memory drive, and large-capacity disks. This computer-readable medium, or media, could be distributed to end-subscribers, licensees, and assignees. A computer program product comprises processor-executable instructions for monitoring a user, as the above paragraphs explained.

While the exemplary embodiments have been described with respect to various features, aspects, and embodiments, those skilled and unskilled in the art will recognize the exemplary embodiments are not so limited. Other variations, modifications, and alternative embodiments may be made without departing from the spirit and scope of the exemplary embodiments.

The invention claimed is:
1. A system, comprising:
a hardware processor; and
a memory device, the memory device storing code, the code when executed causing the hardware processor to perform operations, the operations comprising:
receiving an output signal generated by a sensor, the sensor generating the output signal in response to a user lying on a cushioned pad;
comparing the output signal to a threshold value; and
activating a contact mechanism that imparts a force to the cushioned pad, the contact mechanism activated in response to the output signal satisfying the threshold value, the force being to provoke a movement of the user lying on the cushioned pad to alter the output signal generated by the sensor.

2. The system of claim 1, wherein the contact mechanism comprises at least one peg.

3. The system of claim 2, wherein the contact mechanism slides the at least one peg into contact with the cushioned pad to impart the force.

4. The system of claim 3, wherein the operations further comprise identifying a motor command in response to the output signal, the motor command commanding a motor to cause the at least one peg to slide into contact with the cushioned pad.

5. The system of claim 2, wherein the contact mechanism slides the at least one peg to impart the force to propagate through the cushioned pad.

6. The system of claim 5, wherein the operations further comprise receiving a motor command that commands a motor to cause the at least one peg to impart the force to propagate through the cushioned pad.

7. The system of claim 1, wherein the operations further comprise querying an electronic database for a value associated with the output signal generated by the sensor, the electronic database electronically associating motor commands to values including the value associated with the output signal generated by the sensor.

8. The system of claim 7, wherein the operations further comprise identifying a motor command of the motor commands in the electronic database that is electronically associated with the value associated with the output signal generated by the sensor.

9. The system of claim 8, wherein the operations further comprise sending the motor command to a motor to cause the force imparted to the cushioned pad.

10. The system of claim 1, wherein the operations further comprise inferring a comfort associated with the user lying on the cushioned pad, the comfort based on the output signal generated by the sensor.

11. The system of claim 1, wherein the operations further comprise inferring the user rests on the cushioned pad based on the output signal generated by the sensor.

12. The system of claim 1, wherein the operations further comprise determining an apneatic condition based on the output signal generated by the sensor, the apneatic condition indicating the user lying on the cushioned pad has suspended breathing, and wherein the contact mechanism imparts the force to promote a resumption of the breathing of the user.

13. The system of claim 1, wherein the operations further comprise determining a humidity based on the output signal generated by a humidity sensor, the humidity sensor generating the output signal in response to the user lying on the cushioned pad.

14. The system of claim 1, wherein the operations further comprise determining a humidity based on the output signal generated by a humidity sensor, the humidity sensor comprising at least one conductive strand incorporated into a textile covering the cushioned pad, the humidity sensor generating the output signal in response to the user lying on the cushioned pad above the at least one conductive strand.

15. A monitoring system, comprising:
a cushioned pad;
a motion sensor;
a contact mechanism;
a hardware processor; and
a memory device, the memory device storing code, the code when executed causing the hardware processor to perform operations, the operations comprising:
receiving an output signal generated by the motion sensor, the motion sensor generating the output signal in response to a user lying on the cushioned pad;
comparing the output signal to a threshold value;
determining a status associated with the user in response to the output signal satisfying the threshold value; and
activating the contact mechanism to impart a force through the cushioned pad in response to the status, the contact mechanism for provoking a movement of the user lying on the cushioned pad to alter the output signal generated by the motion sensor.

16. The monitoring system of claim 15, wherein the contact mechanism comprises at least one peg.

17. The monitoring system of claim 16, wherein the contact mechanism slides the at least one peg to impart the force through the cushioned pad.

18. The monitoring system of claim 17, wherein the contact mechanism reciprocates the at least one peg into contact with an upper region of the cushioned pad.

19. The monitoring system of claim 15, wherein the operations further comprise determining an apneatic condition indicating the user has suspended breathing, and wherein the contact mechanism activates to promote a resumption of the breathing of the user lying on the cushioned pad.

20. The monitoring system of claim 15, wherein the operations further comprise generating a motor command in response to the output signal generated by the motion sensor, the motor command commanding the contact mechanism to impart the force through the cushioned pad.

21. The monitoring system of claim 15, wherein the operations further comprise receiving a motor command that commands the contact mechanism to impart the force through the cushioned pad.

22. The monitoring system of claim 15, wherein the operations further comprise wirelessly sending an indication of the output signal to a mobile device.

23. The monitoring system of claim 15, wherein the operations further comprise wirelessly sending an indication of the output signal to a server.

24. The system of claim 15, wherein the operations further comprise determining a humidity based on an output a signal generated by a humidity sensor, the humidity sensor generating the signal in response to the user lying on the cushioned pad.

25. The system of claim 15, wherein the operations further comprise determining a humidity based on a signal generated by a humidity sensor, the humidity sensor comprising at least one conductive strand incorporated into a textile covering the cushioned pad, the humidity sensor generating the signal in response to the user lying on the cushioned pad above the at least one conductive strand.

26. A method, comprising:
receiving, by a server, a service request sent via the Internet from a client device, the service request requesting a cloud-based monitoring service performed on behalf of the client device, the service request specifying a value associated with an output signal generated by a motion sensor in response to a user lying on a cushioned pad;
querying, by the server, an electronic database for the value associated with the output signal generated by the motion sensor, the electronic database electronically associating motor commands to values including the value associated with the output signal generated by the motion sensor;
identifying, by the server, a motor command of the motor commands in the electronic database that is electronically associated to the value associated with the output signal generated by the motion sensor; and
sending, by the server, the motor command via the Internet to the client device, the motor command sent in response to the service request requesting the cloud-based monitoring service, the motor command causing the client device to activate a contact mechanism in response to the value associated with the output signal generated by the motion sensor, the contact mechanism activated to impart a force through the cushioned pad to provoke a movement of the user lying on the cushioned pad to alter the value associated with the output signal generated by the motion sensor.

27. The method of claim 26, further comprising retrieving a notification address associated with the client device sending the service request.

28. The method of claim 27, further comprising sending an electronic notification to the notification address associated with the client device sending the service request, the electronic notification notifying of the status.

29. The method of claim 26, further comprising initiating a short message service text message to the notification address associated with the client device sending the service request, the short message service text message notifying of the status.

30. The method of claim 26, further comprising identifying an apneatic condition that is electronically associated to the value associated with the output signal generated by the motion sensor, the apneatic condition indicating the user has suspended breathing.

31. The method of claim 30, further comprising sending an electronic notification to a notification address associated with the client device sending the service request, the electronic notification notifying of the apneatic condition indicating the user has suspended the breathing.

32. The method of claim 30, further comprising initiating a short message service text message to a notification address associated with the client device sending the service request, the short message service text message notifying of the apneatic condition indicating the user has suspended the breathing.

33. A monitoring system, comprising:
a contact mechanism having at least one peg;
a cushioned pad overlaying the contact mechanism having the peg;
a motion sensor;
a hardware processor; and
a memory device, the memory device storing code, the code when executed causing the hardware processor to perform operations, the operations comprising:
receiving an output signal generated by the motion sensor, the motion sensor generating the output signal in response to a user lying on the cushioned pad;
comparing the output signal to a threshold value;

determining a status associated with the user lying on the cushioned pad, the status determined in response to the output signal satisfying the threshold value;

activating the contact mechanism in response to the status; and reciprocating the peg to impart a force through the cushioned pad overlaying the contact mechanism;

wherein the force is for provoking a movement in the user lying on the cushioned pad to alter the output signal generated by the motion sensor.

34. The monitoring system of claim 33, wherein the operations further comprise determining an apneatic condition indicating the user has suspended breathing, and wherein the reciprocating of the peg promotes a resumption of the breathing, and wherein the resumption of the breathing changes the output signal generated by the motion sensor.

35. The monitoring system of claim 33, wherein the operations further comprise identifying a motor command in response to the output signal generated by the motion sensor, the motor command causing the activating of the contact mechanism.

36. The monitoring system of claim 33, further comprising a humidity sensor for sensing a humidity associated with the user lying on the cushioned pad.

37. The monitoring system of claim 36, wherein the humidity sensor comprises a conductive textile for the sensing of the humidity associated with the user lying on the cushioned pad.

38. The monitoring system of claim 36, wherein the humidity sensor comprises conductive strands disposed between the cushioned pad and the contact mechanism.

39. The monitoring system of claim 36, wherein the humidity sensor comprises conductive strands integrated into a covering of the cushioned pad.

40. The monitoring system of claim 36, wherein the humidity sensor comprises conductive strands disposed between an upper surface of the cushioned pad and the contact mechanism.

* * * * *